US012637692B2

(12) United States Patent
Deverman et al.

(10) Patent No.: US 12,637,692 B2
(45) Date of Patent: May 26, 2026

(54) MACHINE LEARNING ACCELERATED PROTEIN ENGINEERING THROUGH FITNESS PREDICTION

(71) Applicant: The Broad Institute, Inc., Cambridge, MA (US)

(72) Inventors: Benjamin E. Deverman, Cambridge, MA (US); Fatmaelzahraa Sobhy Abdelmouty Eid, Cambridge, MA (US); Ken Y. Chan, Cambridge, MA (US)

(73) Assignee: The Broad Institute, Inc., Cambridge, MA (US)

( * ) Notice: Subject to any disclaimer, the term of this patent is extended or adjusted under 35 U.S.C. 154(b) by 1018 days.

(21) Appl. No.: 17/244,774

(22) Filed: Apr. 29, 2021

(65) Prior Publication Data

US 2021/0403946 A1 Dec. 30, 2021

Related U.S. Application Data

(60) Provisional application No. 63/017,510, filed on Apr. 29, 2020.

(51) Int. Cl.
*C12N 15/86* (2006.01)
*C12N 15/10* (2006.01)
*G16B 35/00* (2019.01)

(52) U.S. Cl.
CPC ......... *C12N 15/86* (2013.01); *C12N 15/1037* (2013.01); *G16B 35/00* (2019.02)

(58) Field of Classification Search
CPC ..... C12N 15/86; C12N 15/1037; G16B 35/00
See application file for complete search history.

(56) References Cited

U.S. PATENT DOCUMENTS

| | | | |
|---|---|---|---|
| 5,552,157 | A | 9/1996 | Yagi et al. |
| 5,565,213 | A | 10/1996 | Nakamori et al. |
| 5,567,434 | A | 10/1996 | Szoka, Jr. |
| 5,738,868 | A | 4/1998 | Shinkarenko |
| 5,741,516 | A | 4/1998 | Webb et al. |
| 5,795,587 | A | 8/1998 | Gao et al. |
| 7,198,951 | B2 | 4/2007 | Gao et al. |
| 9,585,971 | B2 | 3/2017 | Deverman et al. |
| 2017/0166926 | A1 | 6/2017 | Deverman et al. |
| 2022/0143214 | A1 | 5/2022 | Deverman et al. |

FOREIGN PATENT DOCUMENTS

| | | |
|---|---|---|
| WO | WO 2008/103962 A2 | 8/2008 |
| WO | WO 2015/038958 A1 | 3/2015 |
| WO | WO 2017/100671 A1 | 6/2017 |
| WO | WO 2018/017754 A1 | 1/2018 |
| WO | WO 2019/211401 A1 | 11/2019 |
| WO | WO 2020/014471 A1 | 1/2020 |
| WO | WO 2020/028751 A3 | 2/2020 |
| WO | WO 2020/068990 A1 | 4/2020 |
| WO | WO-2020160337 A1 * | 8/2020 ........... A61K 48/005 |

OTHER PUBLICATIONS

Tabuchi, Ichiro et al. "Multi-Line Split DNA Synthesis: A Novel Combinatorial Method to Make High Quality Peptide Libraries." BMC biotechnology 4.1 (2004) (Year: 2004).*
International Search Report and Written Opinion for Application No. PCT/US2021/029985, mailed Aug. 13, 2021.
Albright et al., Discovery of a Neurotropic Footprint That Enables AAV Transport Across the Blood-Brain Barrier. Mol Ther. 2017; 25(5): 230-231.
Aurnhammer et al., Universal real-time PCR for the detection and quantification of adeno-associated virus serotype 2-derived inverted terminal repeat sequences. Hum Gene Ther Methods. Feb. 2012;23(1):18-28. doi: 10.1089/hgtb.2011.034.
Aurnhammer et al., Universal real-time PCR for the detection and quantification of adeno-associated virus serotype 2-derived inverted terminal repeat sequences. Hum Gene Ther Methods. Feb. 2012;23(1):18-28. Supplementary Information. 2 pages.
Bedbrook et al., Machine learning-guided channelrhodopsin engineering enables minimally invasive optogenetics. Nat Methods. Nov. 2019;16(11):1176-1184. doi: 10.1038/s41592-019-0583-8. Epub Oct. 14, 2019.
Biswas et al., Toward machine-guided design of proteins. bioRxiv. Jun. 2, 2018; 1; 1-10. DOI: 10.1101/337154.
Bogan et al., Anatomy of hot spots in protein interfaces. J Mol Biol. Jul. 3, 1998;280(1):1-9. doi: 10.1006/jmbi.1998.1843.
Börner et al., Pre-arrayed Pan-AAV Peptide Display Libraries for Rapid Single-Round Screening. Mol Ther. Apr. 8, 2020;28(4):1016-1032. doi: 10.1016/j.ymthe.2020.02.009. Epub Feb. 13, 2020.
Bryant et al., Deep diversification of an AAV capsid protein by machine learning. Nat Biotechnol. Jun. 2021;39(6):691-696. doi: 10.1038/s41587-020-00793-4. Epub Feb. 11, 2021.
Chan et al., Engineered AAVs for efficient noninvasive gene delivery to the central and peripheral nervous systems. Nat Neurosci. Aug. 2017;20(8):1172-1179. doi: 10.1038/nn.4593. Epub Jun. 26, 2017.

(Continued)

*Primary Examiner* — Soren Harward
*Assistant Examiner* — Dawn Bickham
(74) *Attorney, Agent, or Firm* — Wolf, Greenfield & Sacks, P.C.

(57) ABSTRACT

Techniques for identifying production-fit amino acid sequence libraries are disclosed. The techniques may include accessing a statistical model relating an input amino acid sequence to production fitness of a protein having the input amino acid sequence, obtaining production fitness information for production-fit variant amino acid sequences, and generating an amino acid sequence library having amino acid sequences with predicted production fitness in accordance with the production fitness information. The techniques further include using a statistical model for a protein characteristic other than production fitness to generate an amino acid sequence library having amino acid sequences that are both predicted to be production-fit and have the protein characteristic.

8 Claims, 33 Drawing Sheets

Specification includes a Sequence Listing.

(56) References Cited

OTHER PUBLICATIONS

Chao et al., Isolating and engineering human antibodies using yeast surface display. Nat Protoc. 2006;1(2):755-68. doi: 10.1038/nprot. 2006.94.

Dalkara et al., In vivo-directed evolution of a new adeno-associated virus for therapeutic outer retinal gene delivery from the vitreous. Sci Transl Med. Jun. 12, 2013;5(189):189ra76. doi: 10.1126/scitranslmed.3005708.

Danecek et al., Twelve years of SAMtools and BCFtools. Gigascience. Feb. 16, 2021;10(2):giab008. doi: 10.1093/gigascience/giab008.

Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.

Flytzanis et al., Broad gene expression throughout the mouse and marmoset brain after intravenous delivery of engineered AAV capsids. bioRxiv. 2020;1:1-21.

Hanlon et al., Selection of an Efficient AAV Vector for Robust CNS Transgene Expression. Mol Ther Methods Clin Dev. Oct. 23, 2019;15:320-332. doi: 10.1016/j.omtm.2019.10.007. eCollection Dec. 13, 2019.

Hochreiter et al., Long short-term memory. Neural Comput. Nov. 15, 1997;9(8):1735-80. doi: 10.1162/neco.1997.9.8.1735.

Huang et al., Delivering genes across the blood-brain barrier: LY6A, a novel cellular receptor for AAV-PHP.B capsids. PLoS One. Nov. 14, 2019;14(11):e0225206. doi: 10.1371/journal.pone.0225206. eCollection 2019.

Kariolis et al., Brain delivery of therapeutic proteins using an Fc fragment blood-brain barrier transport vehicle in mice and monkeys. Sci Transl Med. May 27, 2020;12(545):eaay1359. doi: 10.1126/scitranslmed.aay1359.

Körbelin et al., A brain microvasculature endothelial cell-specific viral vector with the potential to treat neurovascular and neurological diseases. EMBO Mol Med. Jun. 1, 2016;8(6):609-25. doi: 10.15252/emmm.201506078. Print Jun. 2016.

Kumar et al., Multiplexed Cre-dependent selection yields systemic AAVs for targeting distinct brain cell types. Nat Methods. May 2020;17(5):541-550. doi: 10.1038/s41592-020-0799-7. Epub Apr. 20, 2020.

Langmead et al., Fast gapped-read alignment with Bowtie 2. Nat Methods. Mar. 4, 2012;9(4):357-9. doi: 10.1038/nmeth.1923.

Li et al., The Sequence Alignment/Map format and SAMtools. Bioinformatics. Aug. 15, 2009;25(16):2078-9. doi: 10.1093/bioinformatics/btp352. Epub Jun. 8, 2009.

Lisowski et al., Selection and evaluation of clinically relevant AAV variants in a xenograft liver model. Nature. Feb. 20, 2014;506(7488):382-6. doi: 10.1038/nature12875. Epub Dec. 25, 2013.

Marques et al., Applying machine learning to predict viral assembly for adeno-associated virus capsid libraries. Mol Ther Methods Clin Dev. Dec. 3, 2020;20:276-286. doi: 10.1016/j.omtm.2020.11.017. eCollection Mar. 12, 2021.

Mason et al., Deep learning enables therapeutic antibody optimization in mammalian cells by deciphering high-dimensional protein sequence space. bioRxiv. 2019;1:1-25.

Matochko et al., Deep sequencing analysis of phage libraries using Illumina platform. Methods. Sep. 2012;58(1):47-55. doi: 10.1016/j.ymeth.2012.07.006. Epub Jul. 20, 2012.

Mattheakis et al., An in vitro polysome display system for identifying ligands from very large peptide libraries. Proc Natl Acad Sci U S A. Sep. 13, 1994;91(19):9022-6. doi: 10.1073/pnas.91.19.9022.

Mccafferty et al., Phage antibodies: filamentous phage displaying antibody variable domains. Nature. Dec. 6, 1990;348(6301):552-4. doi: 10.1038/348552a0.

Müller et al., Random peptide libraries displayed on adeno-associated virus to select for targeted gene therapy vectors. Nat Biotechnol. Sep. 2003;21(9):1040-6. doi: 10.1038/nbt856. Epub Aug. 3, 2003.

Nonnenmacher et al., Rapid evolution of blood-brain-barrier-penetrating AAV capsids by RNA-driven biopanning. Mol Ther Methods Clin Dev. Dec. 23, 2020;20:366-378. doi: 10.1016/j.omtm. 2020.12.006. eCollection Mar. 12, 2021.

Ogden et al., Comprehensive AAV capsid fitness landscape reveals a viral gene and enables machine-guided design. Science. Nov. 29, 2019;366(6469):1139-1143. doi: 10.1126/science.aaw2900.

Paulk et al., Bioengineered Viral Platform for Intramuscular Passive Vaccine Delivery to Human Skeletal Muscle. Mol Ther Methods Clin Dev. Jul. 24, 2018;10:144-155. doi: 10.1016/j.omtm.2018.06. 001. eCollection Sep. 21, 2018.

Pulicherla et al., Engineering liver-detargeted AAV9 vectors for cardiac and musculoskeletal gene transfer. Mol Ther. Jun. 2011;19(6):1070-8. doi: 10.1038/mt.2011.22. Epub Mar. 1, 2011.

Qian et al., Directed Evolution of AAV Serotype 5 for Increased Hepatocyte Transduction and Retained Low Humoral Seroreactivity. Mol Ther Methods Clin Dev. Oct. 20, 2020;20:122-132. doi: 10.1016/j.omtm.2020.10.010. eCollection Mar. 12, 2021.

Ravn et al., By-passing in vitro screening—next generation sequencing technologies applied to antibody display and in silico candidate selection. Nucleic Acids Res. Nov. 2010;38(21):e193. doi: 10.1093/nar/gkq789. Epub Sep. 15, 2010.

Riesselman et al., Accelerating Protein Design Using Autoregressive Generative Models. BioRxiv. 2019; 1: 1-7.

Rolnick et al., Deep Learning is Robust to Massive Label Noise. ArXiv. 2018; 3: 1-10.

Sinai et al., A primer on model-guided exploration of fitness landscapes for biological sequence design. ArXiv. Oct. 23, 2020; 2:1-43.

Smith, Filamentous fusion phage: novel expression vectors that display cloned antigens on the virion surface. Science. Jun. 14, 1985;228(4705):1315-7. doi: 10.1126/science.4001944.

Tervo et al., A Designer AAV Variant Permits Efficient Retrograde Access to Projection Neurons. Neuron. Oct. 19, 2016;92(2):372-382. doi: 10.1016/j.neuron.2016.09.021. Epub Oct. 6, 2016.

Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. doi: 10.1074/jbc.M116.741314. Epub Aug. 30, 2016.

Tse et al., Structure-guided evolution of antigenically distinct adeno-associated virus variants for immune evasion. Proc Natl Acad Sci U S A. Jun. 13, 2017;114(24):E4812-E4821. doi: 10.1073/pnas. 1704766114. Epub May 30, 2017.

Weinmann et al., Identification of a myotropic AAV by massively parallel in vivo evaluation of barcoded capsid variants. Nat Commun. Oct. 28, 2020;11(1):5432. doi: 10.1038/s41467-020-19230-w.

Whitehead et al., Optimization of affinity, specificity and function of designed influenza inhibitors using deep sequencing. Nat Biotechnol. May 27, 2012;30(6):543-8. doi: 10.1038/nbt.2214.

Yang et al., Machine-learning-guided directed evolution for protein engineering. Nat Methods. Aug. 2019;16(8):687-694. doi: 10.1038/s41592-019-0496-6. Epub Jul. 15, 2019.

International Preliminary Report on Patentability for Application No. PCT/US2021/029985, mailed Nov. 10, 2022.

[No Author Listed], GENBANK Submission; NCBI, Accession No. XP_001381054.1; Predicted: similar to olfactory receptor Olr218 [Monodelphis domestica]; Feb. 27, 2007.

Akache et al., The 37/67-kilodalton laminin receptor is a receptor for adeno-associated virus serotypes 8, 2, 3, and 9. J Virol. Oct. 2006;80(19):9831-6. doi: 10.1128/JVI.00878-06.

Allen et al., Global Representations of Goal-Directed Behavior in Distinct Cell Types of Mouse Neocortex. Neuron. May 17, 2017;94(4):891-907.e6. doi: 10.1016/j.neuron.2017.04.017.

Bedbrook et al., Viral Strategies for Targeting the Central and Peripheral Nervous Systems. Annu Rev Neurosci. Jul. 8, 2018;41:323-348. doi: 10.1146/annurev-neuro-080317-062048. Epub Apr. 25, 2018.

Bell et al., Identification of the galactose binding domain of the adeno-associated virus serotype 9 capsid. J Virol. Jul. 2012;86(13):7326-33. doi: 10.1128/JVI.00448-12. Epub Apr. 18, 2012.

Brass et al., Identification of host proteins required for HIV infection through a functional genomic screen. Science. Feb. 15, 2008;319(5865):921-6. doi: 10.1126/science.1152725. Epub Jan. 10, 2008.

(56)　　　　　References Cited

OTHER PUBLICATIONS

Chinni et al., CXCL12/CXCR4 transactivates HER2 in lipid rafts of prostate cancer cells and promotes growth of metastatic deposits in bone. Mol Cancer Res. Mar. 2008;6(3):446-57. doi: 10.1158/1541-7786.MCR-07-0117.

Cray et al., Regulation and selective expression of Ly-6A/E, a lymphocyte activation molecule, in the central nervous system. Brain Res Mol Brain Res. Jun. 1990;8(1):9-15. doi: 10.1016/0169-328x(90)90003-v.

Davis et al., Rational design and engineering of a modified adeno-associated virus (AAV1)-based vector system for enhanced retrograde gene delivery. Neurosurgery. Feb. 2015;76(2):216-25; discussion 225. doi: 10.1227/NEU.0000000000000589.

Dayton et al., More expansive gene transfer to the rat CNS: AAV PHP.EB vector dose-response and comparison to AAV PHP.B. Gene Ther. Aug. 2018;25(5):392-400. doi: 10.1038/s41434-018-0028-5. Epub Jul. 16, 2018.

Deutscher et al., Mechanism of galactosylation in the Golgi apparatus. A Chinese hamster ovary cell mutant deficient in translocation of UDP-galactose across Golgi vesicle membranes. J Biol Chem. Jan. 5, 1986;261(1):96-100.

Eichhoff, Nanobodies as tools for optimizing adeno-associated viruses for gene and tumor therapy. Dissertation, University of Hamburg. May 4, 2018. URL: https://ediss.sub.nnj-hamburg.de/yolltexte/2018/9158/.

Excoffon et al., Directed evolution of adeno-associated virus to an infectious respiratory virus. Proc Natl Acad Sci U S A. Mar. 10, 2009;106(10):3865-70. doi: 10.1073/pnas.0813365106. Epub Feb. 23, 2009.

Fu et al., Crossing the blood-brain-barrier with viral vectors. Curr Opin Virol. Dec. 2016;21:87-92. doi: 10.1016/j.coviro.2016.08.006. Epub Sep. 1, 2016.

Fujimura et al., A lipid raft-associated 67kDa laminin receptor mediates suppressive effect of epigallocatechin-3-O-gallate on FcepsilonRI expression. Biochem Biophys Res Commun. Oct. 21, 2005;336(2):674-81. doi: 10.1016/j.bbrc.2005.08.146.

Gao et al., Clades of Adeno-associated viruses are widely disseminated in human tissues. J Virol. Jun. 2004;78(12):6381-8. doi: 10.1128/JVI.78.12.6381-6388.2004.

Gao et al., Therapeutic Delivery of Butyrylcholinesterase by Brain-Wide Viral Gene Transfer to Mice. Molecules. Jul. 8, 2017;22(7):1145. doi: 10.3390/molecules22071145.

Gibson et al., Adeno-Associated Viral Gene Therapy Using PHP. B:NPC1 Ameliorates Disease Phenotype in Mouse Model of Niemann—Pick C 1 Disease (conference paper). American Society of Gene and Cell Therapy Annual Meeting. Washington, DC, USA. (May 10-13, 2017).

Girod et al., Genetic capsid modifications allow efficient re-targeting of adeno-associated virus type 2. Nat Med. Sep. 1999;5(9):1052-6. doi: 10.1038/12491.

Guida et al., Mouse adenovirus type 1 causes a fatal hemorrhagic encephalomyelitis in adult C57BL/6 but not BALB/c mice. J Virol. Dec. 1995;69(12):7674-81. doi: 10.1128/JVI.69.12.7674-7681. 1995.

Hillier et al., Causal evidence for retina-dependent and -independent visual motion computations in mouse cortex. Nat Neurosci. Jul. 2017;20(7):960-968. doi: 10.1038/nn.4566. Epub May 22, 2017.

Hordeaux et al., The Neurotropic Properties of AAV-PHP.B Are Limited to C57BL/6J Mice. Mol Ther. Mar. 7, 2018;26(3):664-668. doi: 10.1016/j.ymthe.2018.01.018. Epub Feb. 2, 2018.

Huang et al., Parvovirus glycan interactions. Curr Opin Virol. Aug. 2014;7:108-18. doi: 10.1016/j.coviro.2014.05.007. Epub Jul. 19, 2014.

Jackson et al., Better Targeting, Better Efficiency for Wide-Scale Neuronal Transduction with the Synapsin Promoter and AAV-PHP. B. Front Mol Neurosci. Nov. 4, 2016;9:116. doi: 10.3389/fnmol. 2016.00116. eCollection 2016.

Jarvinen et al., Systemically Administered, Target Organ-Specific Therapies for Regenerative Medicine. Int J Mol Sci. Sep. 30, 2015;16(10):23556-71. doi: 10.3390/ijms161023556.

Keane et al., Mouse genomic variation and its effect on phenotypes and gene regulation. Nature. Sep. 14, 2011;477(7364):289-94. doi: 10.1038/nature10413.

Kikkert et al., Binding of Tomato Spotted Wilt Virus to a 94-kDa Thrips Protein. Phytopathology. Jan. 1998;88(1):63-9. doi: 10.1094/PHYTO.1998.88.1.63.

Kotterman et al., Engineered AAV vectors for improved central nervous system gene delivery. Neurogenesis. Dec. 3, 2015;2(1):e1122700. doi: 10.1080/23262133.2015.1122700. eCollection 2015.

Krishnan et al., RNA interference screen for human genes associated with West Nile virus infection. Nature. Sep. 11, 2008;455(7210):242-5. doi: 10.1038/nature07207.

Li et al., Single amino acid modification of adeno-associated virus capsid changes transduction and humoral immune profiles. J Virol. Aug. 2012;86(15):7752-9. doi: 10.1128/JVI.00675-12. Epub May 16, 2012.

Liu et al., Identification of chicken lymphocyte antigen 6 complex, locus E (LY6E, alias SCA2) as a putative Marek's disease resistance gene via a virus-host protein interaction screen. Cytogenet Genome Res. 2003;102(1-4):304-8. doi: 10.1159/000075767.

Loeuillet et al., In vitro whole-genome analysis identifies a susceptibility locus for HIV-1. PLoS Biol. Feb. 2008;6(2):e32. doi: 10.1371/journal.pbio.0060032.

Loughner et al., Organization, evolution and functions of the human and mouse Ly6/uPAR family genes. Hum Genomics 10, 10, doi:10. 1186/s40246-016-0074-2.

Malek et al., Role of Ly-6 in lymphocyte activation. II. Induction of T cell activation by monoclonal anti-Ly-6 antibodies. J Exp Med. Sep. 1, 1986;164(3):709-22. doi: 10.1084/jem.164.3.709.

Mar et al., LY6E mediates an evolutionarily conserved enhancement of virus infection by targeting a late entry step. Nat Commun. Sep. 6, 2018;9(1):3603. doi: 10.1038/s41467-018-06000-y.

Matsuzaki et al., Intravenous administration of the adeno-associated virus-PHP.B capsid fails to upregulate transduction efficiency in the marmoset brain. Neurosci Lett. Feb. 5, 2018;665:182-188. doi: 10.1016/j.neulet.2017.11.049. Epub Nov. 24, 2017.

Mayor et al., Sorting GPI-anchored proteins. Nat Rev Mol Cell Biol. Feb. 2004;5(2):110-20. doi: 10.1038/nrm1309.

Mendell et al., Single-Dose Gene-Replacement Therapy for Spinal Muscular Atrophy. N Engl J Med. Nov. 2, 2017;377(18):1713-1722. doi: 10.1056/NEJMoa1706198.

Morabito et al., AAV-PHP.B-Mediated Global-Scale Expression in the Mouse Nervous System Enables GBA1 Gene Therapy for Wide Protection from Synucleinopathy. Mol Ther. Dec. 6, 2017;25(12):2727-2742. doi: 10.1016/j.ymthe.2017.08.004. Epub Aug. 10, 2017.

Münch et al., Off-target-free gene delivery by affinity-purified receptor-targeted viral vectors. Nat Commun. Feb. 10, 2015;6:6246. doi: 10.1038/ncomms7246.

Nathwani et al., Advances in Gene Therapy for Hemophilia. Hum Gene Ther. Nov. 2017;28(11):1004-1012. doi: 10.1089/hum.2017. 167.

Nonnenmacher et al., Adeno-Associated Virus 2 Infection Requires Endocytosis through the CLIC/GEEC Pathway. Cell Host Microbe. Dec. 15, 2011; 10(6): 563-76.

Ojala et al., In Vivo Selection of a Computationally Designed Schema AAV Library Yields a Novel Variant for Infection of Adult Neural Stem Cells in the SVZ. Mol Ther. Jan. 3, 2018;26(1):304-319. doi: 10.1016/j.ymthe.2017.09.006. Epub Sep. 8, 2017.

Ortega et al., Role of Ly-6 in lymphocyte activation. I. Characterization of a monoclonal antibody to a nonpolymorphic Ly-6 specificity. J Immunol. Nov. 15, 1986;137(10):3240-6.

Pierleoni et al., PredGPI: a GPI-anchor predictor. BMC Bioinformatics. Sep. 23, 2008;9:392. doi: 10.1186/1471-2105-9-392.

Pillay et al., AAV serotypes have distinctive interactions with domains of the cellular receptor AAVR. J Virol. Aug. 24, 2017;91(18):e00391-17. doi: 10.1128/JVI.00391-17. Print Sep. 15, 2017.

Pillay et al., An essential receptor for adeno-associated virus infection. Nature. Feb. 4, 2016;530(7588):108-12. doi: 10.1038/nature16465. Epub Jan. 27, 2016.

(56)　　　　　　References Cited

OTHER PUBLICATIONS

Ran et al., In vivo genome editing using *Staphylococcus aureus* Cas9. Nature. Apr. 9, 2015;520(7546):186-91. doi: 10.1038/nature14299. Epub Apr. 1, 2015.

Ravina et al., Intraputaminal AADC gene therapy for advanced Parkinson's disease: interim results of a phase lb Trial [abstract]. Human Gene Therapy. Dec. 1, 2017; 28(12): A6. Accessed at: https://doi.org/10.1089/hum.2017.29055.abstracts.

Sago et al., High-throughput in vivo screen of functional mRNA delivery identifies nanoparticles for endothelial cell gene editing. Proc Natl Acad Sci U S A. Oct. 16, 2018;115(42):E9944-E9952. doi: 10.1073/pnas.1811276115. Epub Oct. 1, 2018.

Sago et al., Nanoparticles That Deliver RNA to Bone Marrow Identified by in Vivo Directed Evolution. J Am Chem Soc. Dec. 12, 2018;140(49):17095-17105. doi: 10.1021/jacs.8b08976. Epub Nov. 16, 2018.

Sah, Safety and Increased Transduction Efficiency in the Adult Nonhuman Primate Central Nervous System with Intravenous Delivery of Two Novel Adeno-Associated Virus Capsids [abstract 0661]. American Society of Gene and Cell Therapy Annual Meeting. Chicago, IL, USA. Molecular Therapy. (May 16-19, 2018).

Saha et al., GPI-anchored protein organization and dynamics at the cell surface. J Lipid Res. Feb. 2016;57(2):159-75. doi: 10.1194/jlr.R062885. Epub Sep. 22, 2015.

Shen et al., Terminal N-Linked Galactose Is the Primary Receptor for Adeno-associated Virus 9. J Biol Chem. Apr. 15, 2011;286(15):13532-40. doi: 10.1074/jbc.M110.210922. Epub Feb. 17, 2011.

Simon et al., Epithelial cell adhesion molecule-targeted drug delivery for cancer therapy. Expert Opin Drug Deliv. Apr. 2013;10(4):451-68. doi: 10.1517/17425247.2013.759938. Epub Jan. 14, 2013.

Spindler et al., The major locus for mouse adenovirus susceptibility maps to genes of the hematopoietic cell surface-expressed LY6 family. J Immunol. Mar. 15, 2010;184(6):3055-62. doi: 10.4049/jimmunol.0903363. Epub Feb. 17, 2010.

Summerford et al., AAVR: A Multi-Serotype Receptor for AAV. Mol Ther. Apr. 2016;24(4):663-6. doi: 10.1038/mt.2016.49.

Van De Rijn et al., Mouse hematopoietic stem-cell antigen Sca-1 is a member of the Ly-6 antigen family. Proc Natl Acad Sci U S A. Jun. 1989;86(12):4634-8. doi: 10.1073/pnas.86.12.4634.

Yalcin et al., Sequence-based characterization of structural variation in the mouse genome. Nature. Sep. 14, 2011;477(7364):326-9. doi: 10.1038/nature10432.

Zelikowsky et al., The Neuropeptide Tac2 Controls a Distributed Brain State Induced by Chronic Social Isolation Stress. Cell. May 17, 2018;173(5):1265-1279.e19. doi: 10.1016/j.cell.2018.03.037.

Zhang et al., An RN A-sequencing transcriptome and splicing database of glia, neurons, and vascular cells of the cerebral cortex. J Neurosci. Sep. 3, 2014;34(36):11929-47. doi: 10.1523/JNEUROSCI.1860-14.2014.

Zhang et al., Protein structure and sequence re-analysis of 2019-nCoV genome does not indicate snakes as its intermediate host or the unique similarity between its spike protein insertions and HIV-1. bioRxiv. Feb. 8, 2020;2020.02.04.933135. doi: 10.1101/2020.02.04.933135. Preprint.

Zurzolo et al., Glycosylphosphatidylinositol-anchored proteins: Membrane organization and transport. Biochim Biophys Acta. Apr. 2016;1858(4):632-9. doi: 10.1016/j.bbamem.2015.12.018. Epub Dec. 17, 2015.

No Author Listed, Invitrogen TRIzol Reagent Product Page. Thermo Fisher Scientific. Accessed at: https://www.thermofisher.com/order/catalog/product/15596026. Last accessed: Aug. 1, 2025.

* cited by examiner

100

Training Data
102

Production Fitness
Information
104

Amino Acid Sequence
Library
102

Production Fitness
Statistical Model(s)
110

Production-Fit Amino
Acid Sequences
112

Variant Amino Acid
Sequences
108

500

Begin

Obtain Amino Acid Sequence
Library Having Production-Fit
Variant Amino Acid Sequences
510

Screen Amino Acid Sequence
Library for Other Protein
Characteristic(s)
520

Select Subset of Amino Acid
Sequences From Amino Acid
Sequence Library Using
Screening Results
530

End

Hammerhead composition

After calibration

SEQUENCE LISTING

```
<160> NUMBER OF SEQ ID NOS: 26

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Thr Leu Ala Val Pro Phe Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Ser Val Ser Lys Pro Phe Leu
1               5

<210> SEQ ID NO 3
<211> LENGTH: 14
<212> TYPE: DNA
<213> ORGANISM: Artificial Sequence
<220> FEATURE:
<223> OTHER INFORMATION: Synthetic

<400> SEQUENCE: 3 tttttctac aggt                                                      14

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4 ggaacccta gtgatggagt t                                             21

<210> SEQ ID NO 5
<211> LENGTH: 16
<212> TYPE: DNA
<213> ORGANISM: Artificial Sequence
<220> FEATURE:
<223> OTHER INFORMATION: Synthetic

<400> SEQUENCE: 5
cggcctcagt gagcga                                                   16

<210> SEQ ID NO 6
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (9)..(10)
<223> OTHER INFORMATION: linked by ZEN

<400> SEQUENCE: 6
cactccctct ctgcgcgctc g                                             21
```

<210> SEQ ID NO 7
<211> LENGTH: 68
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(36)
<223> OTHER INFORMATION: n is a, c, g, or t

<400> SEQUENCE: 7
ctttccctac acgacgctct tccgatctnn nnnnnnccaa cgaagaagaa attaaaacta      60
ctaacccg                                                              68

<210> SEQ ID NO 8
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(35)
<223> OTHER INFORMATION: n is a, c, g, or t

<400> SEQUENCE: 8
ctttccctac acgacgctct tccgatctnn nnnnnccaac gaagaagaaa ttaaaactac      60
taacccg                                                               67

<210> SEQ ID NO 9
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(34)
<223> OTHER INFORMATION: n is a, c, g, or t

<400> SEQUENCE: 9
ctttccctac acgacgctct tccgatctnn nnnnccaacg aagaagaaat taaaactact      60
aacccg                                                                66

<210> SEQ ID NO 10
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(33)
<223> OTHER INFORMATION: n is a, c, g, or t

<400> SEQUENCE: 10
ctttccctac acgacgctct tccgatctnn nnnccaacga agaagaaatt aaaactacta      60
acccg                                                                 65

<210> SEQ ID NO 11
<211> LENGTH: 64
<212> TYPE: DNA
<213> ORGANISM: Artificial Sequence
<220> FEATURE:

<223> OTHER INFORMATION: Synthetic
<220> FEATURE:
<221> NAME/KEY: misc_feature
<222> LOCATION: (29)..(32)
<223> OTHER INFORMATION: n is a, c, g, or t

<400> SEQUENCE: 11
ctttccctac acgacgctct tccgatctnn nnccaacgaa gaagaaatta aaactactaa     60
cccg                                                                  64

<210> SEQ ID NO 12
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(31)
<223> OTHER INFORMATION: n is a, c, g, or t

<400> SEQUENCE: 12
ctttccctac acgacgctct tccgatctnn nccaacgaag aagaaattaa aactactaac     60
ccg                                                                   63

<210> SEQ ID NO 13
<211> LENGTH: 62
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(30)
<223> OTHER INFORMATION: n is a, c, g, or t

<400> SEQUENCE: 13
ctttccctac acgacgctct tccgatctnn ccaacgaaga agaaattaaa actactaacc     60
cg                                                                    62

<210> SEQ ID NO 14
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: n is a, c, g, or t

<400> SEQUENCE: 14
ctttccctac acgacgctct tccgatctnc caacgaagaa gaaattaaaa ctactaaccc     60
g                                                                     61

<210> SEQ ID NO 15
<211> LENGTH: 53
<212> TYPE: DNA
<213> ORGANISM: Artificial Sequence
<220> FEATURE:
<223> OTHER INFORMATION: Synthetic

<400> SEQUENCE: 15
ggagttcaga cgtgtgctct tccgatctca tctctgtcct gccaaaccat acc           53

-continued

```
<210> SEQ ID NO 16
<211> LENGTH: 54
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(29)
<223> OTHER INFORMATION: n is a, c, g, or t

<400> SEQUENCE: 16
ggagttcaga cgtgtgctct tccgatctnc atctctgtcc tgccaaacca tacc          54

<210> SEQ ID NO 17
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(30)
<223> OTHER INFORMATION: n is a, c, g, or t

<400> SEQUENCE: 17
ggagttcaga cgtgtgctct tccgatctnn catctctgtc ctgccaaacc atacc          55

<210> SEQ ID NO 18
<211> LENGTH: 56
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(31)
<223> OTHER INFORMATION: n is a, c, g, or t

<400> SEQUENCE: 18
ggagttcaga cgtgtgctct tccgatctnn ncatctctgt cctgccaaac catacc          56

<210> SEQ ID NO 19
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(32)
<223> OTHER INFORMATION: n is a, c, g, or t

<400> SEQUENCE: 19
ggagttcaga cgtgtgctct tccgatctnn nncatctctg tcctgccaaa ccatacc          57

<210> SEQ ID NO 20
<211> LENGTH: 58
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(33)
<223> OTHER INFORMATION: n is a, c, g, or t

<400> SEQUENCE: 20
ggagttcaga cgtgtgctct tccgatctnn nnncatctct gtcctgccaa accatacc          58
```

```
<210> SEQ ID NO 21
<211> LENGTH: 59
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(34)
<223> OTHER INFORMATION: n is a, c, g, or t

<400> SEQUENCE: 21
ggagttcaga cgtgtgctct tccgatctnn nnnncatctc tgtcctgcca aaccatacc         59

<210> SEQ ID NO 22
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(35)
<223> OTHER INFORMATION: n is a, c, g, or t

<400> SEQUENCE: 22
ggagttcaga cgtgtgctct tccgatctnn nnnnncatct ctgtcctgcc aaaccatacc        60

<210> SEQ ID NO 23
<211> LENGTH: 149
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (84)..(104)
<223> OTHER INFORMATION: n is a, c, g, or t

<400> SEQUENCE: 23
ccaacgaaga agaaattaaa actactaacc cggtagcaac ggagtcctat ggacaagtgg        60
ccacaaacca ccagagtgcc caannnnnnn nnnnnnnnnn nnnngcacag gcgcagaccg       120
gttgggttca aaaccaagga atacttccg                                        149

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
cggactcaga ctatcagctc cc                                                22

<210> SEQ ID NO 25
<211> LENGTH: 26
<212> TYPE: DNA
<213> ORGANISM: Artificial Sequence
<220> FEATURE:
<223> OTHER INFORMATION: Synthetic

<400> SEQUENCE: 25
gtattccttg gttttgaacc caaccg                                            26

<210> SEQ ID NO 26
<211> LENGTH: 83
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t

<400> SEQUENCE: 26
gtattccttg gtttttgaacc caaccggtct gcgcctgtgc mnnmnnmnnm nnmnnmnnmn        60
nttgggcact ctggtggttt gtg                                                83
```

MACHINE LEARNING ACCELERATED PROTEIN ENGINEERING THROUGH FITNESS PREDICTION

CROSS REFERENCE TO RELATED APPLICATIONS

This application claims the benefit under 35 U.S.C. § 119 (e) of U.S. Provisional Application No. 63/017,510, filed Apr. 29, 2020, entitled "MACHINE LEARNING ACCELERATED AAV CAPSID ENGINEERING THROUGH FITNESS PREDICTION," the entire disclosure of which is hereby incorporated by reference.

FEDERALLY SPONSORED RESEARCH

This invention was made with government support under Grant No. NS111689, awarded by National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Apr. 28, 2021, is named B119570106US01-SEQ-EXG, and is 7.57 kilobytes in size.

FIELD

Aspects of the technology described herein relate to machine learning techniques for engineering protein variants.

BACKGROUND

Creating engineered proteins with multiple characteristics of interest is challenging because of the vast sequence space, rarity of enhanced variants, and potential incompatibility between desired traits. Introducing novel characteristics into proteins, as opposed to enhancing existing characteristics, is particularly challenging, but is necessary for the development of proteins of significant medical and industrial interest such as antibodies and nanobodies, protein-based inhibitors, and gene therapy viral vectors. The resulting protein must not only retain high production or expression fitness, stability, and low immunogenicity, but also gain the ability to bind to a molecular target or perform a novel function.

SUMMARY

Some embodiments are directed to a method for generating a production-fit amino acid sequence library comprising using at least one computer hardware processor to perform: accessing at least one statistical model relating an input amino acid sequence to production fitness of a protein having the input amino acid sequence; obtaining production fitness information for production-fit variant amino acid sequences; and generating, using the at least one statistical model and the production fitness information, an amino acid sequence library having amino acid sequences with predicted production fitness in accordance with the production fitness information.

In some embodiments, the production fitness information corresponds to a mode of a distribution of production fitness data used to train the at least one statistical model. In some embodiments, the at least one statistical model was trained using measured production fitness values having a multimodal distribution with modes, and the production fitness information corresponds to a mode of the multimodal distribution with highest value. In some embodiments, the amino acid sequences of the amino acid sequence library have predicted production fitness values within a distribution centered at the mode of the multimodal distribution with highest value.

In some embodiments, the production fitness information corresponds to a Gaussian distribution centered at a mode of a distribution for production fitness data used to train the at least one statistical model. In some embodiments, the production fitness information corresponds to a high production fitness component of a distribution of production fitness values for amino acid sequences. In some embodiments, the amino acid sequence library has a range of production fitness values within the high production fitness component. In some embodiments, the amino acid sequence library has a distribution of production fitness values with a mean value equal to approximately a mean value of the high production fitness component. In some embodiments, each of the amino acid sequences of the amino acid sequence library has a value for production fitness above a threshold value.

In some embodiments, generating the amino acid sequence library further comprises: generating an initial set of amino acid sequence variants; using amino acid sequences in the initial set as input to the at least one statistical model to obtain values for production fitness; and selecting, based on the values for production fitness and the production fitness information, one or more of the amino acid sequences in the initial set to include in the amino acid sequence library. In some embodiments, the initial set of amino acid sequence variants comprises at least 1,000,000 amino acid sequences. In some embodiments, the amino acid sequence library includes at least 10,000 amino acid sequences.

In some embodiments, the at least one statistical model comprises at least one regression model. In some embodiments, the at least one statistical model comprises at least one neural network. In some embodiments, the at least one statistical model has a recurrent neural network architecture. In some embodiments, the at least one statistical model has a long short-term memory (LSTM) architecture.

In some embodiments, each of the amino acid sequences comprises between 4-20 amino acids. In some embodiments, each of the amino acid sequences comprises 7 amino acids. In some embodiments, each of the amino acid sequences comprises a number of amino acids and at least 60% of the amino acid sequences of the amino acid sequence library have a Hamming distance equal to the number of amino acids.

In some embodiments, the sequences are targeting peptides that are inserted into an adeno-associated virus (AAV) capsid. In some embodiments, the AAV capsid is an AAV9 capsid. In some embodiments, the targeting peptide confers cell binding and/or transduction activity to the AAV capsid.

In some embodiments, the method further comprises manufacturing, using an amino acid sequence of the amino acid sequence library, a protein having the amino acid sequence. In some embodiments, the method further comprises manufacturing, using an amino acid sequence of the amino acid sequence library, an adeno-associated virus (AAV) capsid having the amino acid sequence.

In some embodiments, the method further comprises administering a therapy using an amino acid sequence of the amino acid sequence library. In some embodiments, the method further comprises administering an adeno-associated virus (AAV) therapy, wherein an AAV capsid of the AAV therapy has an amino acid sequence of the amino acid sequence library.

In some embodiments, the method further comprises accessing at least one second statistical model relating an input amino acid sequence to at least one characteristic of a protein other than protein production fitness having the input amino acid sequence; and selecting, using the amino acid sequence library and the at least one second statistical model, a subset of amino acid sequences from the amino acid sequence library. In some embodiments, the at least one second statistical model was trained using at least some of the amino acid sequences of the amino acid sequence library. In some embodiments, the method further comprises training the at least one second statistical model using at least some of the amino acid sequences of the amino acid sequence library as training data.

In some embodiments, the method further comprises accessing at least one statistical model relating an input amino acid sequence to at least one characteristic of a protein other than protein production fitness having the input amino acid sequence; and determining, using the amino acid sequence library and the at least one statistical model, production-fit amino acid sequences having the at least one protein characteristic.

Some embodiments are directed to a system comprising at least one hardware processor; and at least one non-transitory computer-readable storage medium storing processor-executable instructions that, when executed by the at least one hardware processor, cause the at least one hardware processor to perform: accessing at least one statistical model relating an input amino acid sequence to production fitness of a protein having the input amino acid sequence; obtaining production fitness information for production-fit variant amino acid sequences, wherein the production fitness information corresponds to a mode of a distribution for production fitness data used to train the at least one statistical model; and generating, using the at least one statistical model and the production fitness information, an amino acid sequence library having amino acid sequences with predicted production fitness in accordance with the production fitness information.

Some embodiments are directed to at least one non-transitory computer-readable storage medium storing processor-executable instructions that, when executed by at least one hardware processor, cause the at least one hardware processor to perform accessing at least one statistical model relating an input amino acid sequence to production fitness of a protein having the input amino acid sequence; obtaining production fitness information for production-fit variant amino acid sequences, wherein the production fitness information corresponds to a mode of a distribution for production fitness data used to train the at least one statistical model; and generating, using the at least one statistical model and the production fitness information, an amino acid sequence library having amino acid sequences with predicted production fitness in accordance with the production fitness information.

Some embodiments are directed to a method for identifying production-fit amino acid sequences with one or more other protein characteristics comprising using at least one computer hardware processor to perform: obtaining an amino acid sequence library having production-fit variant amino acid sequences; accessing at least one statistical model relating an input amino acid sequence to at least one protein characteristics other than protein production fitness of a protein having the input amino acid sequence; and determining, using the amino acid sequence library and the at least one statistical model, production-fit amino acid sequences having the at least one protein characteristic.

In some embodiments, the method further comprises screening at least some of the amino acid sequences of the amino acid sequence library for the at least one protein characteristic; and training the at least one statistical model based on results from the screening and at least some of the amino acid sequences of the amino acid sequence library. In some embodiments, the method further comprises selecting, using at least one second statistical model relating an input amino acid sequence to production fitness of a protein having the input amino acid sequence, a first set of amino acid sequences from among a plurality of randomly generated amino acid sequences; and selecting, using the at least one statistical model, a second set of amino acid sequences from among the first set of amino acid sequences. In some embodiments, selecting the first set of amino acid sequences further comprises: determining production fitness values for the plurality of randomly generated amino acid sequences using the at least one second statistical model; and selecting the first set of amino acid sequences based on the production fitness values. In some embodiments, selecting the second set of amino acid sequences further comprises: determining values for the at least one protein characteristic using the at least one statistical model and the first set of amino acid sequences; and selecting the second set of amino acid sequences based on the values for the at least one protein characteristic.

In some embodiments, determining the production-fit amino acid sequences having the at least one protein characteristic further comprises selecting, using the amino acid sequence library and the at least one statistical model, amino acid sequences from the amino acid sequence library.

In some embodiments, the at least one statistical model includes a first statistical model for a first protein characteristic and a second statistical model for a second protein characteristic, and determining the production-fit amino acid sequences having the at least one protein characteristic further comprises: using one or more amino acid sequences of the amino acid sequence library as input to the first statistical model to obtain one or more predicted values for the first protein characteristic; using one or more amino acid sequences of the amino acid sequence library as input to the second statistical model to obtain one or more predicted values for the second protein characteristic; and selecting the subset of amino acid sequences based on the one or more predicted values for the first protein characteristic and the one or more predicted values for the second protein characteristic.

In some embodiments, the at least one protein characteristic includes at least one selected from a group consisting of: binding affinity to a target cell type, binding specificity to a target cell type, cell-type specific repulsion, biodistribution to one or more organs or tissues, and transduction of a target cell type. In some embodiments, the at least one protein characteristic includes binding affinity to at least one cell type selected from a group consisting of: liver cell, kidney cell, spleen cell, brain cell, spinal cord cell, heart cell, blood cell, and lung cell. In some embodiments, the at least one protein characteristic includes binding specificity to at least one cell type selected from a group consisting of: liver cell, kidney cell, spleen cell, brain cell, spinal cord cell, heart cell, blood cell, and lung cell. In some embodiments, the at least one protein characteristic includes cell type-specific repulsion of at least one cell type selected from a group consisting of: liver cell, kidney cell, spleen cell, brain cell, spinal cord cell, heart cell, blood cell, and lung cell. In some embodiments, the at least one protein characteristic includes transduction of at least one cell type selected from a group consisting of: liver cell, kidney cell, spleen cell, brain cell, spinal cord cell, heart cell, blood cell, and lung cell.

In some embodiments, each of the amino acid sequences the production-fit amino acid sequences having the at least one protein characteristic comprises between 4-20 amino acids. In some embodiments, each of the amino acid sequences of the production-fit amino acid sequences having the at least one protein characteristic comprises 7 amino acids.

In some embodiments, each of the amino acid sequences of the production-fit amino acid sequences is a targeting peptide inserted into an AAV capsid. In some embodiments, the AAV capsid is an AAV9 capsid. In some embodiments, the targeting peptide confers cell binding and/or transduction activity to the AAV capsid.

In some embodiments, the method further comprises manufacturing, using an amino acid sequence in the subset of amino acid sequences, a protein having the amino acid sequence. In some embodiments, the method further comprises manufacturing, using an amino acid sequence of the production-fit amino acid sequences having the at least one protein characteristic, an adeno-associated virus (AAV) capsid having the amino acid sequence.

In some embodiments, the method further comprises administering a therapy using an amino acid sequence of the production-fit amino acid sequences having the at least one protein characteristic. In some embodiments, the method further comprises administering an adeno-associated virus (AAV) therapy, wherein an AAV capsid of the AAV therapy has an amino acid sequence in the subset of amino acid sequences.

In some embodiments, the at least one statistical model comprises at least one regression model. In some embodiments, the at least one statistical model comprises at least one neural network. In some embodiments, the at least one statistical model has a recurrent neural network architecture. In some embodiments, the at least one statistical model has a long short-term memory (LSTM) architecture.

Some embodiments are directed to a system comprising at least one hardware processor; and at least one non-transitory computer-readable storage medium storing processor-executable instructions that, when executed by the at least one hardware processor, cause the at least one hardware processor to perform: obtaining an amino acid sequence library having production-fit variant amino acid sequences; accessing at least one statistical model relating an input amino acid sequence to at least one protein characteristics other than protein production fitness of a protein having the input amino acid sequence; and determining, using the amino acid sequence library and the at least one statistical model, production-fit amino acid sequences having the at least one protein characteristic.

Some embodiments are directed to at least one non-transitory computer-readable storage medium storing processor-executable instructions that, when executed by at least one hardware processor, cause the at least one hardware processor to perform: obtaining an amino acid sequence library having production-fit variant amino acid sequences; accessing at least one statistical model relating an input amino acid sequence to at least one protein characteristics other than protein production fitness of a protein having the input amino acid sequence; and determining, using the amino acid sequence library and the at least one statistical model, production-fit amino acid sequences having the at least one protein characteristic.

Some embodiments are directed to a method for training at least one statistical model to predict protein production fitness, the method comprising using at least one computer hardware processor to perform: generating amino acid sequences by using a uniform probability distribution over different types of amino acids to randomly generate amino acid sequence variants of an initial amino acid sequence; obtaining production fitness information for the amino acid sequences; and training the at least one statistical model using the amino acid sequences and the production fitness information as training data, wherein the at least one statistical model relates an input amino acid sequence to production fitness of a protein having the input amino acid sequence.

In some embodiments, different types of amino acids occur in the amino acid sequences at approximately same proportions for at least some residue positions. In some embodiments, distributions of amino acid type across the amino acid sequences for at least some residue positions is substantially uniform. In some embodiments, each of at least some residue positions of the amino acid sequences have a substantially uniform distribution of amino acid type across the amino acid sequences.

In some embodiments, obtaining the production fitness information further comprises: screening the one or more protein variants for production fitness; and generating the production fitness information using results from screening the one or more protein variants for production fitness. In some embodiments, the production fitness information includes production fitness measurements obtained for the amino acid sequences.

In some embodiments, the production fitness information includes production fitness values having a multimodal distribution. In some embodiments, the multimodal distribution includes a low production fitness component corresponding to amino acid sequences having low relative production fitness and a high production fitness component corresponding to amino acid sequences having high relative production fitness. In some embodiments, amino acid sequences associated with the high production fitness component have aspartic acid (D) occurring at a higher frequency than amino acid sequences associated with the low production fitness component. In some embodiments, amino acid sequences associated with the high production fitness component have glutamic acid (E) occurring at a higher frequency than amino acid sequences associated with the low production fitness component. In some embodiments, amino acid sequences associated with the high production fitness component have cysteine (C) occurring at a lower frequency than amino acid sequences associated with the low production fitness component. In some embodiments, amino acid sequences associated with the high production fitness component have tryptophan (W) occurring at a lower frequency than amino acid sequences associated with the low production fitness component.

In some embodiments, the at least one statistical model comprises at least one regression model. In some embodiments, the at least one statistical model comprises at least one neural network. In some embodiments, the at least one statistical model has a recurrent neural network architecture. In some embodiments, the at least one statistical model has a long short-term memory (LSTM) architecture.

In some embodiments, the training data includes at least 1,000 amino acid sequences. In some embodiments, the training data includes between 1,000 and 20,000 amino acid sequences. In some embodiments, the training data includes at least one nucleotide sequence encoding each of at least some of the amino acid sequences. In some embodiments, the method further comprises storing the trained at least one statistical model on at least one computer-readable storage medium.

In some embodiments, each of the amino acid sequences comprises between 4-20 amino acids. In some embodiments, each of the amino acid sequences comprises 7 amino acids.

In some embodiments, the initial amino acid sequence is a targeting peptide inserted into an adeno-associated virus (AAV) capsid. In some embodiments, the AAV capsid is an AAV9 capsid. In some embodiments, the targeting peptide confers cell binding and/or transduction activity to the AAV capsid.

Some embodiments are directed to a system for training at least one statistical model to predict protein production fitness, the system comprising at least one hardware processor; and at least one non-transitory computer-readable storage medium storing processor-executable instructions that, when executed by the at least one hardware processor, cause the at least one hardware processor to perform: generating amino acid sequences by using a uniform probability distribution over different types of amino acids to randomly generate amino acid sequence variants of an initial amino acid sequence; obtaining production fitness information for the amino acid sequences; and training the at least one statistical model using the amino acid sequences and the production fitness information as training data, wherein the at least one statistical model relates an input amino acid sequence to production fitness of a protein having the input amino acid sequence.

Some embodiments are directed to at least one non-transitory computer-readable storage medium storing processor-executable instructions that, when executed by at least one hardware processor, cause the at least one hardware processor to perform a method for training at least one statistical model to predict protein production fitness, the method comprising: generating amino acid sequences by using a uniform probability distribution over different types of amino acids to randomly generate amino acid sequence variants of an initial amino acid sequence; obtaining production fitness information for the amino acid sequences; and training the at least one statistical model using the amino acid sequences and the production fitness information as training data, wherein the at least one statistical model relates an input amino acid sequence to production fitness of a protein having the input amino acid sequence.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used in the present disclosure is for the purpose of description and should not be regarded as limiting. The use of "including," "comprising," or "having," "containing," "involving," and variations of thereof in the present disclosure, is meant to encompass the items listed thereafter and equivalents thereof as well as additional items.

BRIEF DESCRIPTION OF DRAWINGS

Various aspects and embodiments will be described with reference to the following figures. The figures are not necessarily drawn to scale.

FIG. 6A is a schematic showing ML framework for fitness prediction, Fit4Fxn library generation, MultiFxn library generation, and functional validation. FIG. 6B provides a Venn diagram of the training and validation libraries. Two synthetic oligo pool libraries were designed to evenly sample the amino acid sequence space, one for training and one for validation. The library sizes of unique nucleotide (NT) sequences are listed with the number of unique, non-overlapping 7-mer amino acid sequences (AA). Each library contained 20K of overlapping sequences (10K amino acid variants) and 1K of stop codon containing sequences (unique to each library). FIG. 6C is a schematic depicting the multi-step process of generating Fit4Fxn libraries: unbiased high quality training data is generated through multiple levels of replications that are then properly aggregated. Fitness is measured as log fold change of the abundance of packaged virus relative to its starting amount in the plasmid library. An ML fitness predictor is trained and tested on subsets of this data to be able to predict production fitness for new sequence variants. The trained model is then used to score production fitness of a large corpus of randomly generated variants across the sequence space. The fitness scores are mapped to the production fitness landscape and variants that map to the high production fitness distribution are subsampled to constitute a Fit4Fxn library (of arbitrary size), which is optimized for prediction fitness. FIG. 6D depicts generation of MultiFxn libraries. Fit4Fxn is screened across functions of interest and a ML fitness predictor is built for each function. Similar to production fitness sampling in FIG. 6B, each predictor is used to prioritize variants of high (or low) fitness for its function from a huge pool of random variant sequences, the variants at the intersection of those desired functional fitness are put into a library, MultiFxn, and screened across the desired functions to validate their multi-function optimization.

FIG. 7A provides a graph showing replication quality between the technical and biological replicates.

VxRy: Virus preparation x by Researcher Y, rz: technical replicate z, ca: codon replicate a. FIG. 7B provides a graph showing replication quality between virus preparations when the three technical replicates of each virus were aggregated (averaged after normalizing for sequencing depth). Vx: Virus preparation x. FIG. 7C provides a graph showing replication quality between researchers when two virus preparations by the same researcher were aggregated. Ry: Researcher Y. FIG. 7D provides a graph showing replication quality between codon replicates when the four virus preparations by the two researchers were combined, but still the codon replicates were kept separate. FIG. 7E provides a graph showing upper level replication quality for the 10K control set shared between the training and validation libraries to show replicability of fitness between library pools when large number of replicates were aggregated to cancel out noise.

FIG. 8A provides a graph showing that correlation between production fitness score of codon replicates (r=0.89) indicates that learning can happen at the amino acid level not nucleotide level. FIG. 8B provides a graph showing production fitness landscape of the training library. A Gaussian mixture model of the fitness distribution is fitted over this distribution, with low-fit to the left and high-fit to the right. FIG. 8C provides a graph showing the amino acid distribution by position for the variants in the low and high fit distributions of the training library, the entire training library (Training All), and in the 70K most abundant sequences in an NNK library. FIG. 8D provides a graph showing that replication quality of the control set (10K) shared between the training and validation libraries shows that fitness scores are replicable (relative to a uniformly sampled fitness landscape). FIGS. 8E-8F provides graphs showing production fitness predictor performance: measured versus predicted fitness score when the fitness predictor is trained on a subset of the training library and tested on another subset of the same library (FIG. 8E) and when tested on the independent validation library (FIG. 8F). FIG. 8G provides a graph showing that predictor performance across different training sizes indicates minimal training variants (~1K) are needed to obtain reasonable prediction accuracy. The validation performance was assessed on a subset of the training library not overlapping with the training or the testing subsets. The dual performance plot also shows that the fitness predictor final training at 24K examples does not cause model overfitting and thus the model generalizes well as demonstrated in the study. FIG. 8H provides a graph showing the prediction quality as measured by the correlation between measured and predicted fitness scores when using different levels of data aggregation for the training. Single sample data (1) was not aggregated. The model was trained using single measurement data. Single virus (3) was aggregated by within experiment replicates. Two viruses (6) aggregated replicates and researchers. Two codon replicates aggregated all data at the nucleotide level. Left bars were trained and tested on the data aggregated as described. Right bars show the prediction quality when trained with the data aggregated as described, but then tested on the full aggregated data.

FIG. 11A provides a graph showing the scored fitness of the members of the simulated Fit4fxn library (sampled from the validation library variant pool as the sequence space) versus the predicted fitness. FIG. 11B provides a graph showing distribution of the measured fitness scores for the simulated Fit4Fxn library variants projected against the fitness landscape of the selection pool.

FIG. 12A and FIG. 12D show the control set (3K) in training and Hammerhead libraries before (FIG. 12A) and after (FIG. 12D) calibration. FIG. 12B and FIG. 12E show the distribution of the fitness scores in Hammerhead library projected against the fitness landscape (from the training library) before (FIG. 12B) and after (FIG. 12E) calibration. There was agreement between the predicted and measured fitness scores for Hammerhead before (FIG. 12C, MSE=3.0585) and after (FIG. 12F, MSE=2.8175) calibration.

FIG. 13A provides graphs showing performance measured as the correlation between measured and predicted variant fitnesses for the functions studied, including human and mouse cell binding and transduction assays. The test sets are held-out subsets of the Hammerhead library. FIG. 13B provides a graph showing replication quality of functional assays screened by Hammerhead versus an NNK library measured as the average replication (correlation r) across pairs of three replicates. FIG. 13C provides a graph showing prediction quality for machine learning models trained to predict functional fitness when trained on Hammerhead data and NNK data.

FIG. 14A provides a graph showing replication quality between pairs of animals for the biodistribution to a variety of organs. The BrainSpinal is the aggregation of the data from brain and spinal cord for each animal. FIG. 14B provides a graph showing correlation analysis across organs. FIG. 14C provides graphs showing measured versus predicted correlation plots for each organ.

FIG. 15A provides a graph showing summary stats for replication quality across the three assays (liver biodistribution, HepG2 binding, HepG2 transduction). FIGS. 15B-15D provide graphs showing predicted versus measured enrichment for mouse liver biodistribution (FIG. 15B), human HepG2 binding (FIG. 15C), and human HepG2 transduction (FIG. 15D). FIG. 15E provides a histogram of measured variants in validation experiments (N=1,491) selected, at a precision of 0.83, for all of the following: high production fitness, high liver biodistribution, high HepG2 binding, high HepG2 transduction.

FIG. 16 shows a validation of multifunction optimized variant selection using the Fit4Fxn-MultiFxn paradigm using a heatmap representing the 'precision' of multifxn selection. Precision is defined as the number of true positives (taken as variants predicted and measured to have the optimized functions in the Hammerhead 150K held out subset) over the number of variants in the same set of 150K that were predicted to be optimized for the functions. Each function can be optimized for low fitness (Low) or high fitness (High). White intersections represent zero predicted elements.

DETAILED DESCRIPTION

Figure 1A:
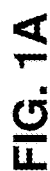
FIG. 1A is a diagram of an illustrative process for training and using production fitness statistical model to generate a production-fit amino acid sequence library, using the technology described herein.

Aspects of the disclosure relate to a novel machine learning approach that combines deep learning and synthetic libraries to predict protein variants with enhanced traits. This approach allows for identifying protein variants having multiple protein characteristics. In particular, these machine learning models can be used to predict the fitness of variants across multiple traits relevant to accelerating the development of next generation vehicles for gene therapy. As discussed further herein, this approach may be implemented to identify modified AAV capsids with multiple protein characteristics of interest for use in gene therapy. It should be appreciated that these models are similarly applicable to other contexts in which multi-feature optimization of protein variants is useful, such as identification of epitopes, antibodies, nanobodies, and protein-based inhibitors.

The inventors have recognized that various challenges can arise during engineering proteins where there are multiple protein characteristics of interest, particularly because of the high number of possible combinations of amino acid sequences, the possible rarity in identifying variants enhanced for one or more protein characteristics, and potential incompatibility between desired traits. For example, in AAV capsid engineering, variants that are selected for increased gene delivery to a cell type of interest may suffer from low production yields, a lack of target cell specificity, or poor translation across species. This can lead to the unfruitful expenditure of time and resources pursuing capsid candidates that ultimately do not translate to the clinic. Introducing novel characteristics into proteins, rather than enhancing existing characteristics, is particularly challenging but is also necessary for the development of proteins of significant medical and industrial interest.

In addition, the inventors have recognized certain challenges may arise in identifying protein variants that exhibit production fitness. Accordingly, some aspects of the present disclosure relate to machine learning models that allow for identifying amino acid sequences having a high production fitness. As used herein "production fitness" of a sequence refers to the ability of the sequence to be expressed as a functional protein.

One of ordinary skill in the art would be able to determine appropriate assays for assessing production fitness of a sequence. A sequence's production fitness may depend on the core properties of the protein produced by the sequence, including whether the sequence produces a protein that folds in a particular manner.

In the context of AAV capsids, production fitness of a sequence may relate to its ability to encode a capsid protein that folds and assembles into a viral capsid particle that can protect the AAV genome. In this context, a non-limiting example of an assay that may be used to assess a sequence's production fitness is an assay that measures the amount of a capsid sequence, or sequence operationally linked to a capsid sequence, that is protected from a nuclease by the AAV capsid encoded by the sequence. In the context of an antibody or nanobody or portion thereof, production fitness may relate to the amount of protein produced by a sequence and may be determined using assays known in the art.

It should be appreciated that other measurable protein properties may be used to assess protein production fitness.

Conventional approaches to engineer novel proteins typically rely on the diversification of short linear sequences or structural epitopes. Libraries containing hundreds of thousands or even hundreds of millions of variants of the protein are then subjected to rounds of selective pressure to isolate the rare variants with a desired enhanced or novel property. High-throughput techniques, e.g., phage-display, yeast-display, ribosome-display, or viral capsid library screens are combined with next-generation sequencing (NGS) to quantitatively track variant distributions.

Similarly, a common approach to isolating adeno-associated virus (AAV) capsids with enhanced function is to funnel a random library of 7-mer peptide-modified capsids (estimated 1.28 billion theoretical variants) through multiple rounds of selective pressure to identify a small number of rare, top performing candidates. After isolating rare candidate variants that are highly fit in the context of the selected trait(s), the variants can be diversified once again to screen for additional traits such as high production yield (Chan et al. 2017; Kariolis et al. 2020). However, success is not guaranteed because characteristics of interest may not be compatible with each other and the protein sequence space is too vast to effectively sample by chance for ultra-rare variants that are optimized across multiple traits. Therefore, it remains difficult to identify variants that exhibit two or more traits important for clinical or industrial translation.

To address some of the aforementioned problems with conventional techniques for engineering protein variants, the inventors have developed improved protein engineering techniques using computational techniques. The improved techniques allow for generating variant amino acid sequences that are production-fit. These computational techniques allow for the identification of amino acid sequences that are production-fit and, in some instances, have one or more other protein characteristics of interest. This in silico approach provides a search tool for identifying novel amino acid sequence variants without synthesizing and screening individual sequences. In particular, these computational techniques can be used to predict multiple protein characteristics for different amino acid sequence variants. These amino acid sequence variants can be further assessed as part of the development of next generation therapies.

Some existing amino acid sequence libraries (e.g., NNK libraries) may have amino acid sequences considered to be production-fit, but have limited diversity of amino acid type across the sequence library. Some of these libraries may have biases for particular types of amino acids across the amino acid sequences in the library and for particular residue positions. The inventors have recognized that using these amino acid sequence libraries as training data for statistical models to predict production fitness may generate biases in the trained statistical models and, thus impact a model's ability to accurately predict whether an input amino acid sequence is production-fit or not. As a result, these biases introduced by the training data may result in mis-identification of amino acid sequences as being production-fit, and thus potentially discarding production-fit amino acid sequences because the model indicates otherwise.

The inventors have further recognized that using amino acid sequences that are randomly generated using a uniform probability as training data for statistical models that predict protein production fitness improves performance of the ability of these models to accurately predict amino acid sequences as being production-fit. In particular, using these statistical models trained in this manner allows for the identification of novel and unique amino acid sequences that may not otherwise be identified using statistical models trained using conventional amino acid sequence libraries alone. This allows for using these statistical models to generate production-fit amino acid sequence libraries that differ from conventional amino acid sequence libraries. In some instances, production-fit amino acid sequences generated using the statistical models described herein may have greater diversity in amino acid type and across residue positions than conventional amino acid sequence libraries.

In some instances, the training data used according to the techniques described herein may include amino acid sequences having low production fitness as well as amino acid sequences having high production fitness. Using amino acid sequences that vary across the production fitness landscape as training data for a statistical model results in training the model both on amino acid sequences considered to not only be true positives, but also true negatives. In the context of using a regression model for predicting protein production fitness, estimating the relationship between amino acid sequences and production fitness values may benefit both from amino acid sequences with low production fitness values as well as those with high production fitness values. In this sense, the inventors have recognized that training a regression model in this way may improve the overall ability of the model to more accurately identify amino acid sequences that are production-fit. As discussed further herein, training the model in this way allows for improved accuracy and performance of the model.

In addition to improving the accuracy in predicting production fitness for amino acid sequences, another benefit of using training data that includes amino acid sequences with both low production fitness and high production fitness is that less training data may be needed to achieve accurate performance for a statistical model to predict protein production fitness. When obtaining production fitness measurements for an amino acid sequence, multiple measurements may be obtained and aggregated. Typically, the aggregate value for production fitness is used as training data. However, the inventors have recognized that a statistical model trained on single measurements per amino acid sequence may have a similar level of performance as a statistical model trained on the aggregate values for the amino acid sequences. In this way, fewer production fitness measurements may be needed to achieve an accurately trained model, reducing the time and costs associated with generating the training data for the statistical models described herein.

The statistical models used to predict production fitness for amino acid sequences described herein may be used for identifying production-fit amino acid sequence libraries. These libraries may then be used to identify amino acid sequences that are both production-fit and have one or more other desired protein characteristics (e.g., binding affinity, binding specificity). In some instances, the production-fit amino acid sequences may be further screened for one or more other protein characteristics. In other instances, a statistical model that predicts a protein characteristic other than production fitness may be used in determining whether an amino acid sequence has that protein characteristic. Here, the statistical model may effectively act as computational screening of the amino acid sequences to identify a subset of amino acid sequences that are both production-fit and have one or more desired protein characteristics. Such computational techniques further reduce time and cost associated with synthesizing amino acid sequences and screening the amino acid sequences for these characteristics. These computational techniques may also enable the prediction of rare sequences that may be missed due to sparse sampling. Furthermore, by predicting these sequences, it makes it possible for a researcher to generate libraries that deeply explore the sequence space occupied by variants that are both production-fit and that have one or more desired protein characteristics, and then screen these sequences for variants with the most desirable properties.

Some embodiments described herein address all of the above-described issues that the inventors have recognized with identifying production-fit amino acid sequences, including amino acid sequences having one or more protein characteristics other than production fitness. However, not every embodiment described herein addresses every one of these issues, and some embodiments may not address any of them. As such, it should be appreciated that embodiments of the technology described herein are not limited to addressing all or any of the above-discussed issues with identifying production-fit amino acid sequences.

Aspects of the present application relate to training one or more statistical models to predict protein production fitness. Some embodiments involve generating amino acid sequences by using a uniform probability distribution over different types of amino acids to randomly generate amino acid sequence variants of an initial amino acid sequence. Production fitness information for the amino acid sequences may be obtained, such as by using a screening assay to assess production fitness of the amino acid sequences. Training the one or more statistical models may involve using the amino acid sequences and the production fitness information as training data. A trained statistical model may relate an input amino acid sequence to production fitness of a protein having the input amino acid sequence. In some embodiments, the one or more statistical models may include a regression model. In such embodiments, the one or more statistical models may receive as an input an amino acid sequence and output a value for production fitness. The value for production fitness may indicate how likely the amino acid sequence is to produce a protein. The architecture of the one or more statistical models may include a recurrent neural network. In some embodiments, the one or more statistical models may have a long short-term memory (LSTM) architecture.

The amino acid sequences used as training data for the one or more statistical models that predict production fitness may have a more uniform distribution of amino acid type, particularly in comparison to other conventional amino acid sequence libraries (e.g., NNK library). The amino acid sequences used as training data may correspond to common residue positions in a protein. In some embodiments, the amino acid sequences may each include between 4-20 amino acids. For example, the amino acid sequences may each correspond to a 7-residue protein sequence. In some embodiments, different types of amino acids occur in the training data at approximately same proportions for at least some residue positions. In some embodiments, distributions of amino acid type across the amino acid sequences for one or more residue positions may be substantially uniform. In some embodiments, each of one or more residue positions of the amino acid sequences may have a substantially uniform distribution of amino acid type across the amino acid sequences.

The production fitness information may include production fitness measurements obtained for the amino acid sequences used for training data. In some embodiments, the production fitness information used for training the one or more statistical models that predict production fitness may be obtained by producing variants of the protein having the amino acid sequences, screening the protein variants for production fitness, and generating the production fitness information using results from the screening.

According to some aspects of the technology described herein, features of the production fitness information used in training the one or more statistical models may be used in identifying production-fit amino acid sequences. In some embodiments, the production fitness information includes production fitness values having a multimodal distribution. The multimodal distribution may include a low production fitness component corresponding to amino acid sequences having low relative production fitness and a high production fitness component corresponding to amino acid sequences having high relative production fitness. The inventors have recognized that certain types of amino acids may occur more frequently in the high production fitness component of the multimodal distribution in comparison to the low production fitness component. In some embodiments, amino acid sequences associated with the high production fitness component may have aspartic acid (D) and glutamic acid (E) occurring at a higher frequency than amino acid sequences associated with the low production fitness component. In some embodiments, amino acid sequences associated with the high production fitness component may have cysteine (C) and tryptophan (W) occurring at a lower frequency than amino acid sequences associated with the low production fitness component.

Some embodiments involve generating a production-fit amino acid sequence library using one or more statistical models and production fitness information. The one or more statistical models may relate an input amino acid sequence to production fitness of a protein having the input amino acid sequence. The production fitness information may be for production-fit variant amino acid sequences for a portion or all of a protein. The production-fit amino acid sequence library generated may include amino acid sequences with predicted production fitness in accordance with the production fitness information.

In some embodiments, the production fitness information may correspond to a mode of a distribution of production fitness data used to train the one or more statistical models. In such embodiments, the one or more statistical model was trained using measured production fitness values having a multimodal distribution with different modes, and the production fitness information corresponds to a mode of the multimodal distribution with highest value. The amino acid sequences in the amino acid sequence library may have predicted production fitness values with a distribution centered at the mode of the multimodal distribution with highest value. In some embodiments, the production fitness information corresponds to a Gaussian distribution centered at the mode of the distribution for production fitness data used to train the one or more statistical models.

In some embodiments, generating the amino acid sequence library further comprises generating an initial set of amino acid sequence variants, using amino acid sequences in the initial set as input to the one or more statistical models to obtain values for production fitness, and selecting one or more of the amino acid sequences in the initial set to include in the amino acid sequence library based on the values for production fitness and the production fitness information.

According to some embodiments, the production fitness information corresponds to a high production fitness component of a distribution of production fitness values for amino acid sequences. Selecting amino acid sequences to include in the amino acid sequence library may include identifying amino acid sequences that have a value for production fitness within the high production fitness component. In some embodiments, amino acid sequences in the amino acid sequence library have a range of production fitness values with the high production fitness component. In some embodiments, the amino acid sequence library has a distribution of production fitness values with a mean value equal to approximately a mean value of the high production fitness component. In some embodiments, amino acid sequences of the amino acid sequence library each has a value for production fitness above a threshold value. For example, the threshold value may correspond to at or above a production fitness value for a protein (e.g., wildtype protein). Selecting amino acid sequences to include in the amino acid sequence library may include identifying amino acid sequences that have a value for production fitness above the threshold value.

Some embodiments involve using a production-fit amino acid sequence library to identify production-fit amino acid sequences having one or more other protein characteristics other than production fitness. One or more statistical models relating an input amino acid sequence to one or more protein characteristics other than production fitness may be used to determine production-fit amino acid sequences having the one or more protein characteristics. Examples of protein characteristics include binding affinity to a target cell type, binding specificity to a target cell type, cell-type specific repulsion, biodistribution to one or more organs or tissues, and transduction of a target cell type.

In some embodiments, some or all of the amino acid sequences in the production-fit amino acid sequence library may be used to generate training data for a statistical model that predicts another protein characteristic. In such embodiments, amino acid sequences in the production-fit amino acid sequence library may be screened for another protein characteristic and results obtained from the screening are used to train the statistical model. Amino acid sequences may then be analyzed using the statistical model. In some embodiments, randomly generated amino acid sequences may be analyzed using both a statistical model that predicts production fitness and a statistical model that predicts a protein characteristic other than production fitness. In such embodiments, a first set of amino acid sequences may be selected from among the randomly generated amino acid sequences using the statistical model that predicts production fitness and a second set of amino acid sequences may be selected from the first set using the statistical model that predicts a protein characteristic other than production fitness. In this way, the second set of amino acid sequences may be identified as being both production-fit and having the protein characteristic.

In some embodiments, amino acid sequences in a production-fit amino acid sequence library may be used as input for a statistical model that predicts a protein characteristic other than production fitness to identify a subset of amino acid sequences from among the production-fit amino acid sequence library as having the protein characteristic. In this manner, the subset of amino acid sequences may be identified as being both production-fit, by belonging the production-fit library, and having the protein characteristic.

According to some embodiments, multiple statistical models that predict protein characteristics other than production fitness may be implemented according to the techniques described herein. Such models may be used to identify amino acid sequences as having multiple protein characteristics other than production fitness. For example, a first statistical model may be used for identifying amino acid sequences as having affinity for a target cell type and a second statistical model may be used for identifying a subset of those amino acid sequences as having specificity for the target cell type.

It should be appreciated that the various aspects and embodiments described herein be used individually, all together, or in any combination of two or more, as the technology described herein is not limited in this respect.

FIG. 1A is a diagram of an illustrative processing pipeline 100 for identifying production-fit amino acid sequences, which may include training a production fitness model and using the production fitness model to identify production-fit amino acid sequences, in accordance with some embodiments of the technology described herein. Processing pipeline 100 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 100 may be performed by a desktop computer, a laptop computer, and/or a mobile computing device. In some embodiments, processing pipeline may be performed within one or more computing devices that are part of a cloud computing environment.

Figure 8A:
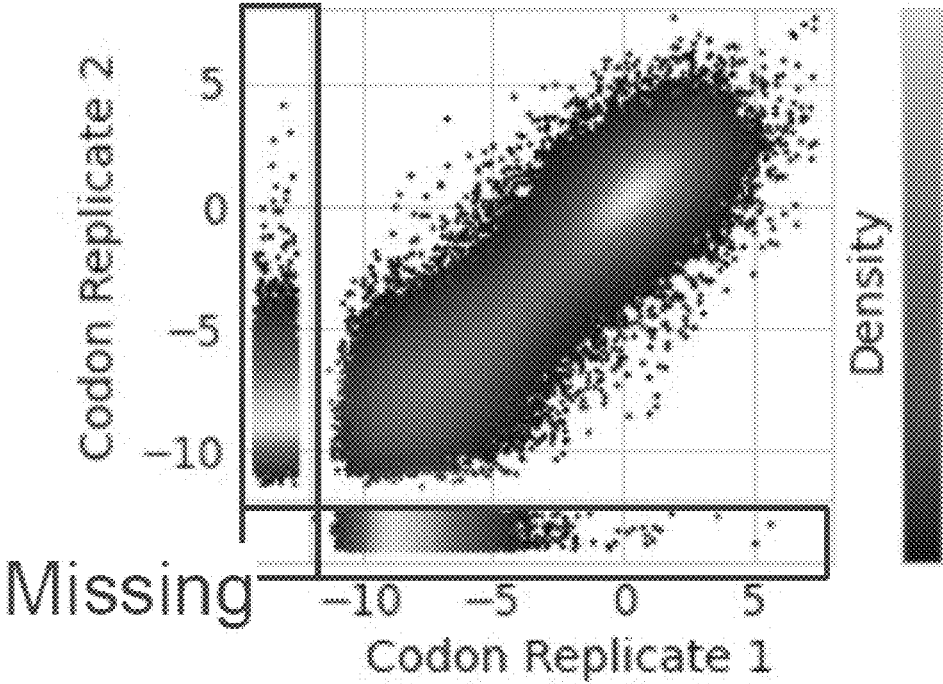
FIGS. 8A-8H provide graphs showing mapping and learning the AAV 7-mer fitness landscape.
Figure 8B:
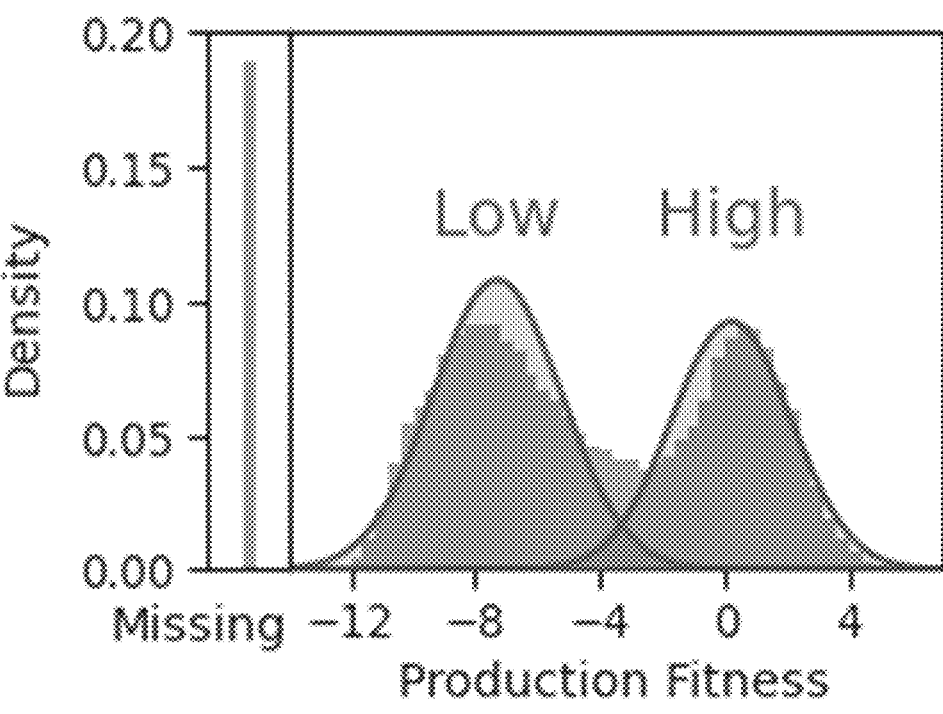
Figure 8C:
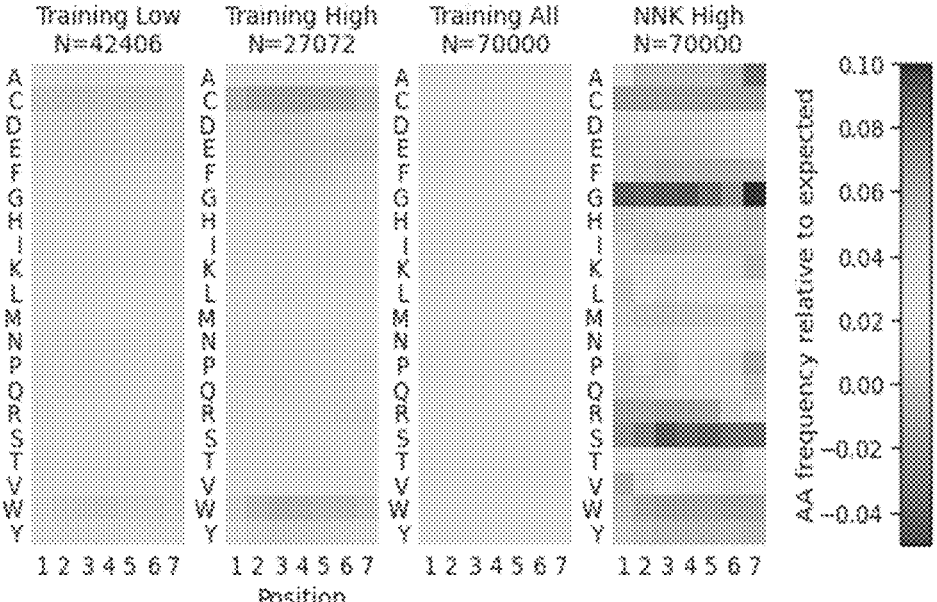

As shown in FIG. 1A, training data 102 may be used to train production fitness statistical model(s) 110. In particular, training data 102 may include production fitness information 106 for amino acid sequences 104. Amino acid sequences 104 may be variants of an initial amino acid sequences randomly generated using a uniform probability distribution over different types of amino acids. Amino acid sequences 104 may have a more uniform distribution of amino acid type, particularly in comparison to other conventional amino acid sequence libraries (e.g., NNK library). For example, FIG. 8C shows graphs illustrating the amino acid distribution by position for variants in low and high production fitness components ("Training Low" and "Training High") of an exemplary training library, the entire training library ("Training All"), and amino acid sequences in an NNK library ("NNK High"). As shown in FIG. 8C, the entire training library ("Training All") has a uniform distribution of amino acid type (shown on the left axis) for all seven positions while the NNK library is more uneven with some amino acid types occurring at higher or lower relative frequencies.

Amino acid sequences 104 may each correspond to common residue positions in a protein. In some embodiments, the amino acid sequences may each include between 4-20 amino acids. For example, the amino acid sequences may each correspond to a 7-residue protein sequence, such as discussed above in connection with FIG. 8C. In some embodiments, different types of amino acids occur in the training data at approximately same proportions for at least some residue positions. The term "approximately" in this context may be used to mean different types of amino acids occurring in the training data within +1% of equal proportions in some embodiments, within +2% of equal proportions in some embodiments, within +5% of equal proportions in some embodiments, and yet within +10% of equal proportions in some embodiments. In some embodiments, distributions of amino acid type across the amino acid sequences for one or more residue positions may be substantially uniform. In some embodiments, each of one or more residue positions of the amino acid sequences may have a substantially uniform distribution of amino acid type across the amino acid sequences. The term "substantially uniform" may be used to mean a distribution of amino acid type within +1% of a uniform distribution in some embodiments, within +2% of a uniform distribution in some embodiments, within +5% of a uniform distribution in some embodiments, and yet within +10% of a uniform distribution in some embodiments.

Production fitness information 106 may include production fitness measurements obtained for amino acid sequences 104. In some embodiments, production fitness information 106 may be obtained by producing variants of a protein each having one of amino acid sequences 104, screening the protein variants for production fitness, and generating production fitness information 106 using results from the screening.

In some embodiments, production fitness information 106 may include particular features of production fitness values for amino acid sequences 104. In some embodiments, production fitness information 106 may include production fitness values having a multimodal distribution. In particular, the multimodal distribution may include a low production fitness component corresponding to amino acid sequences having low relative production fitness and a high production fitness component corresponding to amino acid sequences having high relative production fitness. For example, FIG. 8B illustrates a distribution of production fitness values for the amino acid sequences in the exemplary training library discussed in connection with FIG. 8C. As shown in FIG. 8B, the distribution is a multimodal distribution, and in particular it is a bimodal distribution. The bimodal distribution may be modeled by a Gaussian mixture model with one Gaussian distribution corresponding to a "low production fitness component," which is the mode on the left, and a "high production fitness component," which is the mode on the right. The amino acid sequences corresponding to the high production fitness component and the low production fitness component have certain types of amino acids occurring at different frequencies. As shown in FIG. 8C, the high production fitness component ("Training High") has aspartic acid (D) and glutamic acid (E) occurring at a higher frequency than the low production fitness component ("Training Low"). In addition, the high production fitness component has (C) and tryptophan (W) occurring at a lower frequency than the low production fitness component.

Production fitness statistical model(s) 110 may include a regression model. In such embodiments, training production fitness statistical model(s) 110 may involve estimating relationships between amino acid sequences 104 and production fitness information 106. In particular, training the regression model may involve determining one or more values for one or more parameters to estimate the relationships between amino acid sequences 104 and production fitness information 106. Production fitness statistical model(s) 110 may include one or more neural networks. In some embodiments, the architecture of the production fitness statistical model(s) 110 may include a recurrent neural network. In some embodiments, the production fitness statistical model(s) 110 may involve using a machine learning algorithm that implements a long short-term memory (LSTM) architecture. An example of a machine learning algorithm that implements a LSTM architecture is described in S. Hochreiter and J. Schmidhuber; Long Short-Term Memory, Neural Computation 9 (8): 1735-1780, 1997. Further examples of production fitness statistical model(s) 110 are discussed in Examples 2 and 6 in the "Examples" Section.

Once trained, production fitness statistical model(s) 110 may be used to predict production fitness for amino acid sequences. Production fitness statistical model(s) 110 may relate an input amino acid sequence to production fitness of a protein having the input amino acid sequence. In embodiments where production fitness statistical model(s) 110 include a regression model, statistical model(s) 110 may receive as an input an amino acid sequence and output a value of production fitness for the amino acid sequence. The value for production fitness may indicate how likely the amino acid sequence is to be expressed as a functional protein.

In some embodiments, training may involve using a suitable number of amino acid sequences 104 and corresponding production fitness information 106 to achieve a desired accuracy in predicting production fitness for amino acid sequences. Training data 102 includes at least 1,000, at least 2,000, at least 5,000, or at least 10,000 amino acid sequences. In some embodiments, training data 102 includes less than 20,000, less than 50,000, less than 100,000, or less than 150,000 amino acid sequences. In some embodiments, training data 102 includes between 1,000 and 5,000, between 1,000 and 10,000, between 1,000 and 20,000, between 1,000 and 50,000, or between 1,000 and 150,000 amino acid sequences.

Figure 10A:
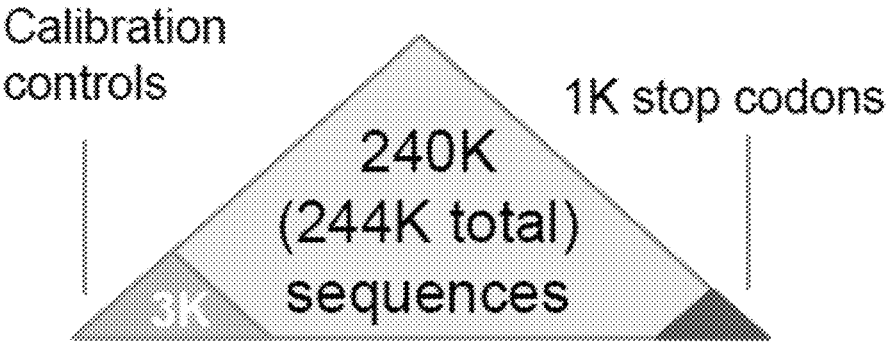
FIG. 10A provides a schematic showing the composition of the Hammerhead Fit4Fxn library.
Figure 10B:
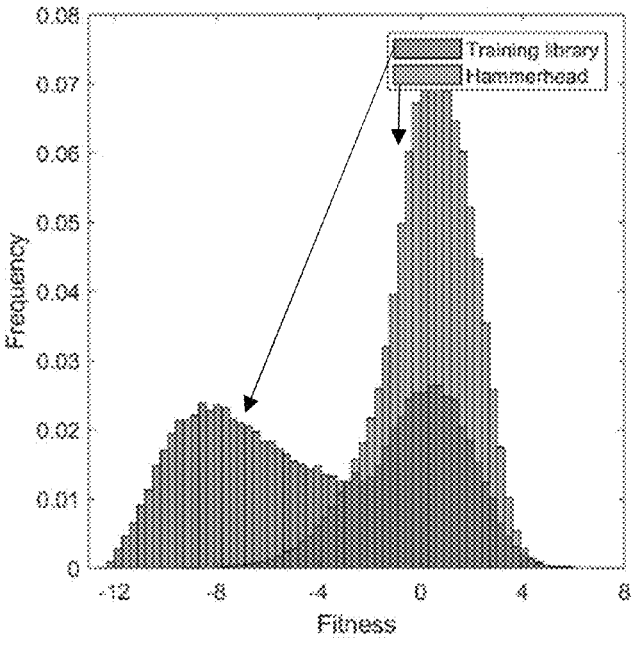
FIG. 10B provides a graph showing distribution of the measured fitness scores (after calibration) for the synthesized Hammerhead library variants projected against the fitness landscape (from the uniformly sampled training library).
Figure 10C:
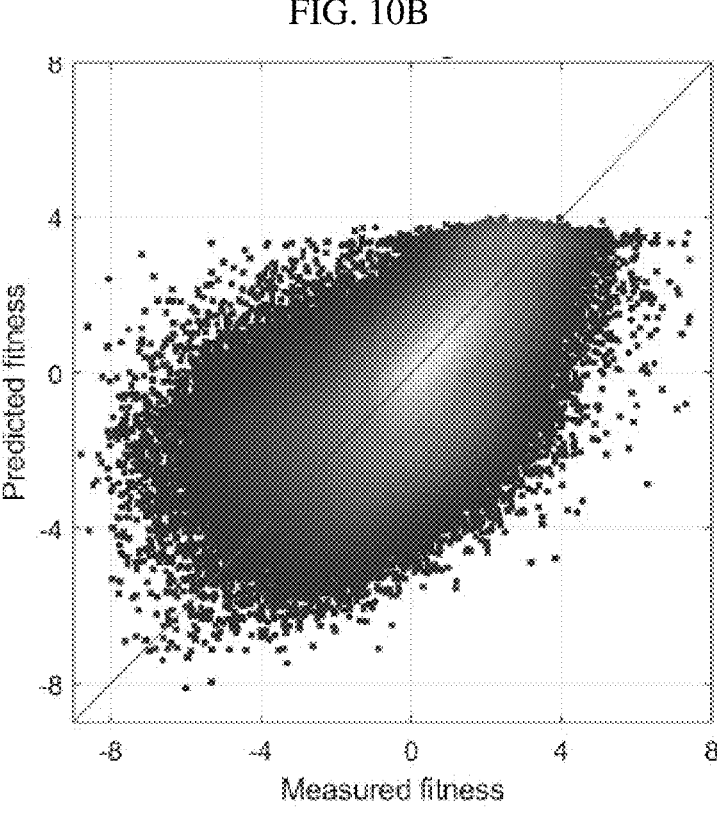
FIG. 10C provides a graph showing the calibrated measured fitness versus corresponding predicted values (before synthesis) of the members of the Fit4Fxn library Hammerhead.

FIG. 10C shows a plot of predicted production fitness values obtained for amino acid sequences using a production fitness statistical model according to the techniques described herein and measured production fitness values for the amino acid sequences.

Production fitness statistical model(s) 110 may be trained for a particular protein or region of a protein. In some embodiments, training data 102 includes amino acid sequences 104 that are variants of a targeting peptide inserted into an adeno-associated virus (AAV) capsid. The targeting peptide may confer cell binding and/or transduction activity to the AAV capsid. Further examples of AAV capsids and portions of AAV capsids are discussed in the "Adeno-associated virus (AAV) vectors" Section.

Production fitness statistical model(s) 110 may be used to generate production-fit amino acid sequence sequences 112. Variant amino acid sequences 108 may be input to production fitness statistical model(s) 110 to obtain production fitness information for variant amino acid sequences 108. One or more variant amino acid sequences 108 may be selected to be included in production-fit amino acid sequences 112 based on the production fitness information for variant amino acid sequences. In some embodiments, selecting a variant amino acid sequence 108 to include in production-fit amino acid sequences 112 may be based on a production fitness value obtained for the variant amino acid sequence 108 using production fitness statistical model(s) 110. Variant amino acid sequences 108 may include at least 1,000 at least 50,000, at least 100,000, or at least 1,000,000 amino acid sequences.

Production fitness information 106 used as training data 102 may be used in selecting a variant amino acid sequence 108 to include in production-fit amino acid sequences 112. In embodiments where production fitness information 106 corresponds to a mode of a distribution of production fitness data used to train production fitness statistical model(s) 110, a variant amino acid sequence 108 may be selected in accordance with the mode. For example, if production fitness statistical model(s) 110 predict a variant amino acid sequence 108 as having a production fitness with the mode, then the variant amino acid sequence is included in production-fit amino acid sequences 112. Production-fit amino acid sequences 112 may have at least 10,000, at least 20,000, or at least 50,000 amino acid sequences.

Amino acid sequences of production-fit amino acid sequences 112 may have predicted production fitness values within a distribution centered as a mode of production fitness information 106 with highest value. In some embodiments, production fitness information 106 may correspond to a Gaussian distribution centered at a mode of a distribution for production fitness data used to train production fitness statistical model(s) 110. The amino acid sequences included in production-fit amino acid sequences 112 have predicted production fitness values may be considered within a "high fitness component" of production fitness information 106. Production-fit amino acid sequences 112 may have a range of production fitness values within the high production fitness component. In some embodiments, production-fit amino acid sequences 112 has a distribution of production fitness values with a mean value equal to approximately a mean value of the high production fitness component.

As an example, FIG. 10B is a graph showing distribution of production fitness values for amino acid sequences used as training data ("Training library") and amino acid sequences belonging to a production-fit amino acid sequence library ("Hammerhead library"). The graph shows how the amino acid sequences in the production-fit amino acid sequence library have production fitness values within the high fitness component of the distribution of production fitness for the amino acid sequences used as training data.

In some embodiments, amino acid sequences of production-fit amino acid sequences 112 may have a value for production fitness above a threshold value. In particular, variant amino acid sequences 108 may be input to production fitness statistical model(s) 110 to obtain production fitness values and selecting variant amino acid sequences 108 to include in production-fit amino acid sequences 112 may include comparing the production fitness values to a threshold value and including variant amino acid sequences 108 having production fitness values above the threshold value. The threshold value for production fitness may vary depending on the protein. In some embodiments, the threshold value may be the same as, greater than, or less than a production fitness value for the protein (e.g., a wildtype protein). In embodiments where the threshold value is greater than the production fitness value for the protein, the threshold value may correspond to a percentage amount greater than the protein's production fitness. For example, the threshold value may be 10% greater, 20% greater, 30% greater, or 40% greater than the production fitness value for the protein. In embodiments where the threshold value is less than the production fitness value for the protein, the threshold value may correspond to a percentage amount less than the protein's production fitness. For example, the threshold value may be 10% less, 20% less, 30% less, or 40% less than the production fitness value for the protein. In some embodiments the threshold value may be set by a user.

Figure 10D:
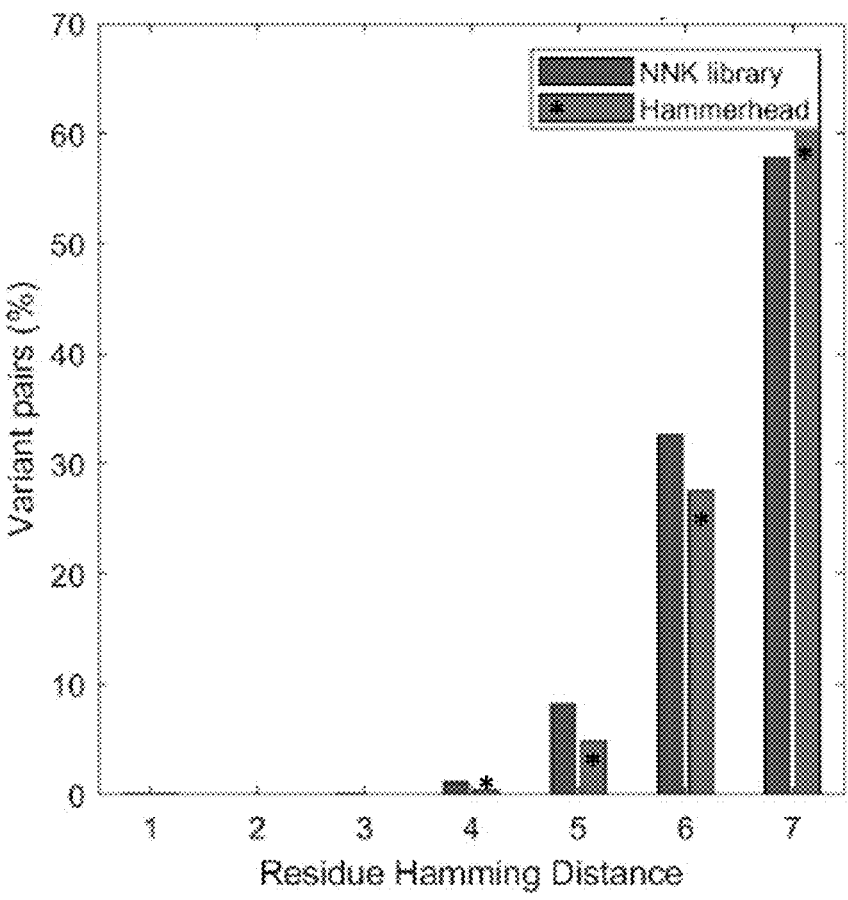
FIG. 10D provides a graph showing distribution of Hamming distances (number of residues that differ at each position) between variant pairs in NNK (left bars) vs the Hammerhead library (right bars) at the amino acid level.

Production-fit amino acid sequences 112 may include amino acid sequences that each have between 4-20 amino acids. In some embodiments, each of the amino acid sequences includes 7 amino acids. In some embodiments, each of the amino acid sequences include a number of amino acids and at least 60% of the amino acid sequences in production-fit amino acid sequences 112 have a Hamming distance equal the number of amino acids. The Hamming distance is a metric for comparing strings of symbols and determining a number of positions in which the symbols are different for the strings of symbols. FIG. 10D is a plot of percentage of variant pairs for an exemplary production-fit amino acid sequence library ("Hammerhead") having amino acid sequences each with 7 amino acids. FIG. 10D shows how over 60% of the amino acid sequences in the production-fit amino acid sequence library have a Hamming distance of 7, meaning that these amino acid sequences differ at all 7 residue positions. This is in comparison to the top 240,000 most abundant variants of the NNK library where less than 60% of the sequences have a Hamming distance of 7.

Figure 10E:
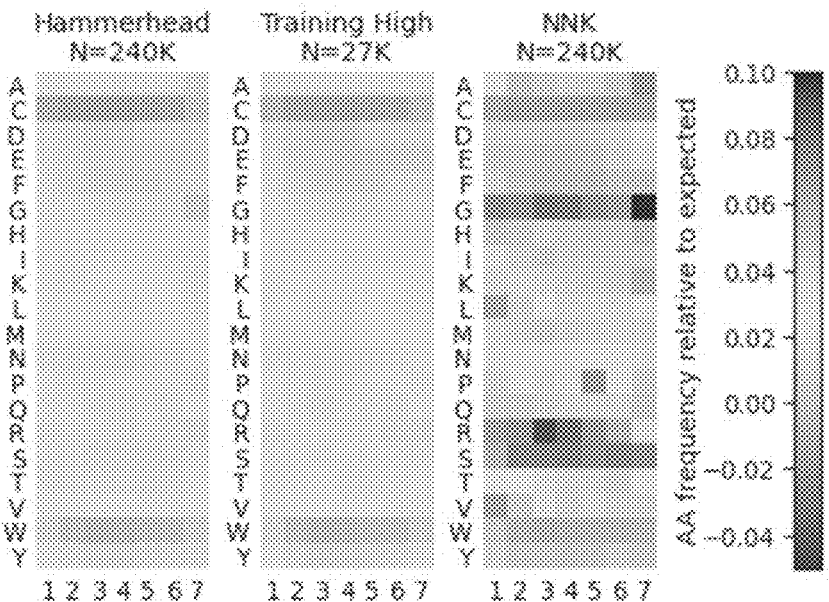
FIG. 10E provides a graph showing the amino acid distribution by position for the variants in the Hammerhead Fit4Fxn library, high fit distribution of the training library, and 240K most abundant sequences in an NNK library.

Production-fit amino acid sequences 112 may have a distribution of amino acid type across residue positions that is similar to a high production fitness component of production fitness information 106. For example, FIG. 10E shows plots of amino acid type distribution for an exemplary production-fit amino acid sequence library ("Hammerhead") and a high production fitness component ("Training High"). As shown in FIG. 10E both the exemplary production-fit amino acid sequence library and the high production fitness component have similar distributions of amino acid type, particularly in contrast to the NNK library.

One or more proteins having an amino acid sequence of production-fit amino acid sequences 112 may be manufactured using suitable techniques, including techniques that involve synthesizing nucleic acid molecules and proteins. In some embodiments, manufacturing a protein having an amino acid sequence of production-fit amino acid sequences 112 may involve inserting a first polynucleotide encoding an amino acid sequence of production-fit amino acid sequences 112 into a second polynucleotide encoding a protein. In such embodiments, a portion of the second polynucleotide may be deleted. In some embodiments, manufacturing a protein having an amino acid sequence of production-fit amino acid sequences 112 may involve substituting a first polynucleotide encoding a protein with a second polynucleotide encoding the amino acid sequence. In such embodiments, a portion of the first polynucleotide may be deleted.

Some embodiments involve manufacturing an adeno-associated virus (AAV) capsid having an amino acid sequence of production-fit amino acid sequences 112. In some embodiments, manufacturing the AAV capsid involves inserting a first polynucleotide encoding a targeting peptide into a second polynucleotide encoding the AAV capsid. In such embodiments, a portion of the second polynucleotide may be deleted. In some embodiments, manufacturing the AAV capsid involves substituting a first polynucleotide encoding the AAV capsid with a second polynucleotide encoding the targeting peptide. In such embodiments, a portion of the first polynucleotide may be deleted.

Some embodiments may involve administering a therapy using an amino acid sequence of production-fit amino acid sequences 112. In embodiments where the protein is an AAV capsid, administering may involve administering an AAV therapy where the AAV capsid of the AAV therapy includes a targeting peptide of production-fit amino acid sequences 112.

Figure 1B:
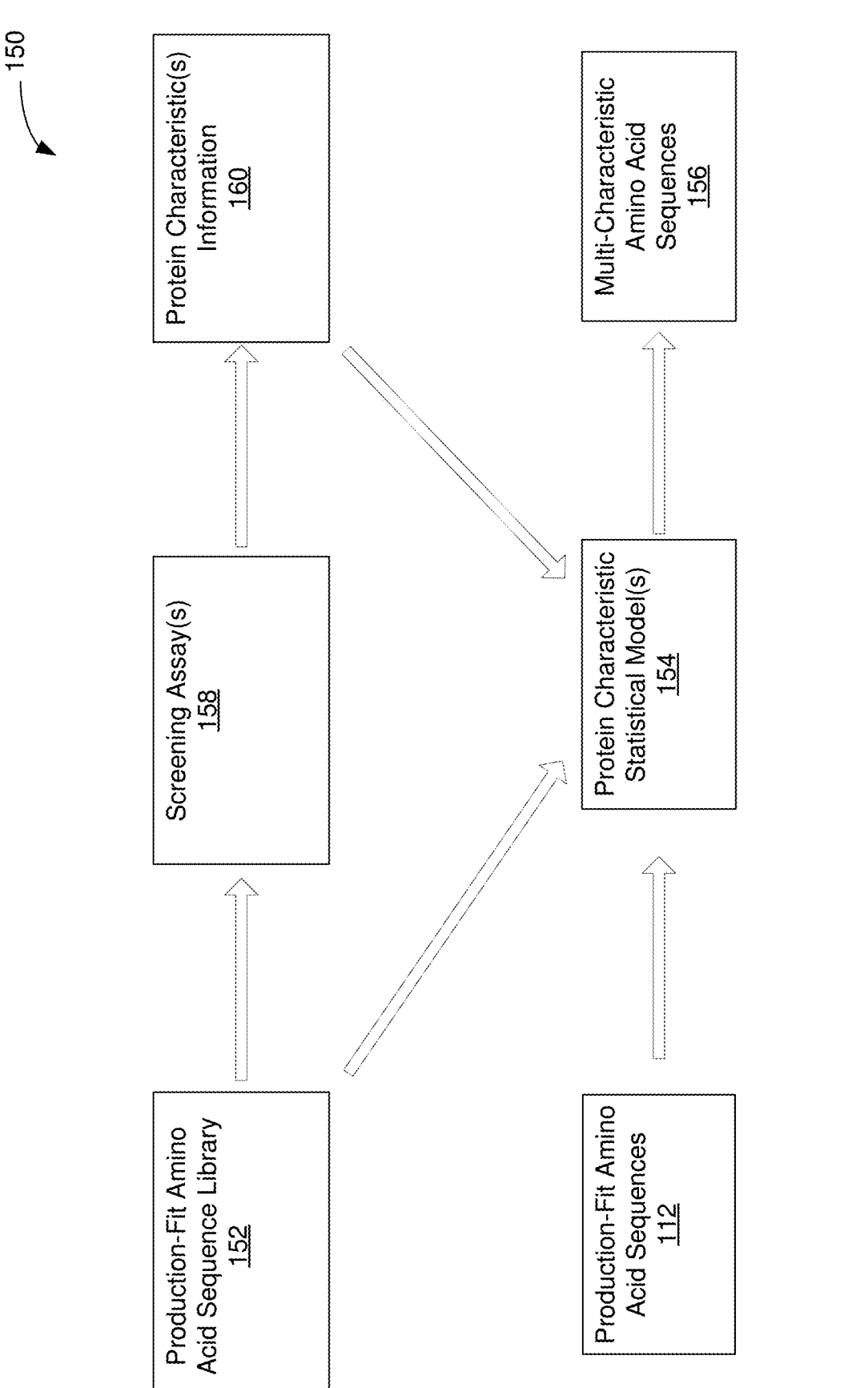
FIG. 1B is a diagram of an illustrative process for identifying production-fit amino acid sequences with one or more protein characteristics other than production fitness, using the technology described herein.

FIG. 1B is a diagram of an illustrative processing pipeline 150 for identifying production-fit amino acid sequences having one or more other protein characteristics, which may include using a production-fit amino acid sequence and one or more protein characteristic statistical model(s), in accordance with some embodiments of the technology described herein. Processing pipeline 150 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, processing pipeline 150 may be performed by a desktop computer, a laptop computer, and/or a mobile computing device. In some embodiments, processing pipeline may be performed within one or more computing devices that are part of a cloud computing environment.

As shown in FIG. 1B, production-fit amino acid sequences 112 and protein characteristic statistical model(s) 154 may be used to identify multi-characteristic amino acid sequences 156. Protein characteristic statistical model(s) 154 relate an input amino acid sequence to one or more protein characteristic other than protein production fitness for a protein having the input amino acid sequence. Multi-characteristic amino acid sequences 156 includes amino acid sequences that are both production-fit and have one or more other protein characteristics.

Examples of protein characteristics that protein characteristic statistical model(s) 154 may be used to predict for amino acid sequences include binding affinity to a target cell type, binding specificity to a target cell type, cell-type specific repulsion, biodistribution to one or more organs or tissues, and transduction of a target cell type. Examples of target cell types include liver cell, kidney cell, spleen cell, brain cell, spinal cord cell, heart cell, blood cell, and lung cell. Further examples of protein characteristics may be found in the "Targeting Peptides" Section, Example 4 in the "Examples" Section, and Example 5 in the "Examples" Section.

Protein characteristic statistical model(s) 154 may include one or more regression models. In such embodiments, training protein characteristic statistical model(s) 154 may involve estimating relationships between amino acid sequences and one or more protein characteristics. In particular, training the regression model may involve determining one or more values for one or more parameters to estimate the relationships between amino acid sequences and the one or more protein characteristics.

Training data used to train protein characteristic statistical model(s) 154 may include production-fit amino acid sequence library 152 and protein characteristic(s) information 160. Production-fit amino acid sequence library 152 may include amino acid sequences identified as having a high production fitness. In some embodiments, production-fit amino acid sequence library 152 may include amino acid sequences identified using production fitness statistical model(s) 110.

Protein characteristic(s) information 160 may be obtained by performing screening assay(s) 158 for production-fit amino acid sequence library 152. The particular screening assay used may depend on the protein characteristic of interest. Protein characteristic(s) information 160 may include results from the screening, including measured values obtained for sequences in the production-fit amino acid sequence library 152. Training protein characteristic statistical model(s) 154 may involve using protein characteristic(s) information 160 and production-fit amino acid sequences 112. In particular, training a protein characteristic statistical model may involve using values of a particular protein characteristic for sequences in production-fit amino acid sequence library 152 to estimate one or more values for one or more parameters of the protein characteristic statistical model. To generate different statistical models for different protein characteristics, different screening assay(s) may be used for production-fit amino acid sequence library 152. Once trained, protein characteristic statistical model(s) 154 may then be used for identifying the one or more protein characteristics for an input amino acid sequence.

Examples of protein characteristics that may be included in protein characteristic(s) information 160 used to train protein characteristic statistical model(s) 154 include binding affinity to a target cell type, binding specificity to a target cell type, cell-type specific repulsion, biodistribution to one or more organs or tissues, and transduction of a target cell type. Examples of target cell types include liver cell, kidney cell, spleen cell, brain cell, spinal cord cell, heart cell, blood cell, and lung cell. Further examples of protein characteristics may be found in the "Targeting Peptides" Section, Example 4 in the "Examples" Section, and Example 5 in the "Examples" Section.

In some embodiments, screening assay(s) may include, e.g., phage-, yeast-, peptide-, and/or ribosome-display approaches. Further examples of screening assay(s) may be found in Example 4 in the "Examples" Section, and Example 5 in the "Examples" Section.

In some embodiments, protein characteristic statistical model(s) 154 includes one or more neural networks. In such embodiments, protein characteristic statistical model(s) 154 may have a recurrent neural network architecture. In some embodiments, protein characteristic statistical model(s) 154 may involve using a machine learning algorithm that implements a long short-term memory (LSTM) architecture. An example of a machine learning algorithm that implements a LSTM architecture is described in S. Hochreiter and J. Schmidhuber; Long Short-Term Memory, Neural Computation 9 (8): 1735-1780, 1997. Further examples of protein characteristic statistical model(s) 154 are discussed in Example 6 in the "Examples" Section.

Using protein characteristic statistical model(s) 154, a set of amino acid sequences may be selected from among production-fit amino acid sequences 112 to include in multi-characteristic amino acid sequences 156. In some embodiments, protein characteristic statistical model(s) 154 may be used for determining values of one or more protein characteristics for production-fit amino acid sequences 112, and the set of amino acid sequences to include in multi-characteristic amino acid sequences 156 may be based on the values of the one or more protein characteristics.

In some embodiments, amino acid sequences of production-fit amino acid sequences 112 may be used as input to the trained protein characteristic statistical model(s) 154. In such embodiments, values for one or more protein characteristics may be identified for amino acid sequences of production-fit amino acid sequences 112 and the values for the one or more protein characteristics may be used to select a subset of amino acid sequences from production-fit amino acid sequence library 112 to include in multi-characteristic amino acid sequences 156.

Some embodiments may involve having multiple protein characteristic statistical models 154, each for different protein characteristics, and selecting a subset of amino acid sequences based on values for those different protein characteristics to include in multi-characteristic amino acid sequences 156. For example, protein characteristic statistical models 154 may include a first statistical model for a first protein characteristic and a second statistical model for a second characteristic. Determining amino acid sequences to include in multi-characteristic amino acid sequences 156 may include using amino acid sequences as input to the first statistical model to obtain predicted values for the first protein characteristic and using amino acid sequences as input to the second statistical model to obtain predicted values for the second protein characteristic. Selecting a subset of amino acid sequences to include in multi-characteristic amino acid sequences 156 may be based on the predicted values for the first protein characteristic and the predicted values for the second protein characteristic. For example, selecting the subset of amino acid sequences may involve selecting amino acid sequences having predicted values for the first protein characteristic that is above a first threshold value and predicted values for the second protein characteristic that is about a second threshold value. In this way, multi-characteristic amino acid sequences 156 includes amino acid sequences that have both the first protein characteristic and the second protein characteristic.

Protein characteristic statistical model(s) 154 may be trained for a particular protein or region of a protein. The amino acid sequences input to protein characteristic statistical model(s) 154 may be variants of the protein or region of the protein. As such, multi-characteristic amino acid sequences 156 may include variants of the protein or region of the protein having one or more protein characteristics that are production-fit. In some embodiments, each of the amino acid sequences in multi-characteristic amino acid sequences 156 has between 4-20 amino acids. In some embodiments, each of the amino acid sequences in multi-characteristic amino acid sequences 156 has 7 amino acids.

In some embodiments, the protein is an adeno-associated virus (AAV) capsid and amino acid sequences of multi-characteristic amino acid sequences 156 includes amino acid sequence variants corresponding to a targeting peptide inserted into the AAV capsid. The targeting peptide may confer cell binding and/pr transduction activity to the AAV capsid. Further examples of AAV capsids and portions of AAV capsids are discussed in the "Adeno-associated virus (AAV) vectors" Section.

Some embodiments involve manufacturing an adeno-associated virus (AAV) capsid having an amino acid sequence of multi-characteristic amino acid sequences 156. In some embodiments, manufacturing the AAV capsid involves inserting a first polynucleotide encoding a targeting peptide into a second polynucleotide encoding the AAV capsid. In such embodiments, a portion of the second polynucleotide may be deleted. In some embodiments, manufacturing the AAV capsid involves substituting a first polynucleotide encoding the AAV capsid with a second polynucleotide encoding a targeting peptide. In such embodiments, a portion of the first polynucleotide may be deleted.

Some embodiments may involve administering a therapy using an amino acid sequence of multi-characteristic amino acid sequences 156. In embodiments where the protein is an AAV capsid, administering may involve administering an AAV therapy where the AAV capsid of the AAV therapy includes a targeting peptide of multi-characteristic amino acid sequences 156.

The above processes illustrated in FIG. 1A and FIG. 1B to generate production-fit amino acid sequences 112 and multi-characteristic amino acid sequences 156 may be referred to herein as "Fit4Fxn"). These computational techniques may systematically and cost-effectively identify modified proteins that possess multiple protein characteristics of interest. The approach described herein conceptually upends traditional approaches by first learning multiple functional landscapes across a vast sequence space, in order to then predict a range of rare protein variants that are likely to be highly fit across multiple traits for downstream validation. Using the approach of the present disclosure, highly generalizable machine learning (ML) models can be effectively trained using moderately sized synthetic libraries that selectively and evenly sample from a production fit sequence space.

The Examples Section provides illustrative examples of how these computational techniques are used to identify modified peptide sequences. In particular, these computational techniques are used to screen 7-mer peptide-modified AAV9 capsids for enhanced functionality, enabling multi-feature optimization of AAV capsid variants. The present disclosure describes multiple sequence-to-function maps for 7-mer peptide-modified AAV9 capsids, generated by assaying a Fit4Fxn library across a variety of in vitro and in vivo functional assays relevant to gene therapy. The resulting quantitative and reproducible data were used to create ML models across multiple measures of capsid production fitness and function. This approach enabled an in silico search of the untested 7-mer sequence space for ultra-rare variants with multiple characteristics of interest. For example, the theoretical 7-mer peptide-modified capsid sequence space was searched for variants that were predicted to be enriched (or de-enriched) across 10 in vitro and in vivo functional assays. As discussed further herein, appropriately sized, minimally biased training libraries have the capacity to produce trained ML models that are highly generalizable. These models can be used to predict the fitness of variants across multiple characteristics, which may be used to accelerate the development of next generation therapies.

The Fit4Fxn approach may include several steps. First, synthetic libraries may be used to uniformly sample each of the 20 amino acids at each position to train and validate a ML model that accurately predicts production fitness. As discussed herein and shown in the Examples, the ML framework design and learning process can be generalizable as demonstrated by equivalent fitness prediction accuracy in held out subsets of the training library and an independent validation library. In addition, it was observed that AAV capsid production fitness can be learned with less than 20K variants, suggesting that future implementations of this approach can utilize smaller libraries of amino acid variants with more nucleotide replicates to generate training and validation data, thereby substantially reducing the expended time, cost, and labor necessary to learn other fitness landscapes. Thus, this library strategy and model design can still be accurate although fewer experimental replicates may be used for model training.

In addition, models used to predict production fitness may be used to generate a library composed exclusively of variants that evenly sample the production fit sequence space. By sampling only from the high fit distribution, Fit4Fxn libraries may eliminate about 60% of the amino acid 7-mer sequence space, which may otherwise increase the impact of fitness bias and waste resources on difficult to manufacture variants. Furthermore, the resulting highly diverse and production fit Fit4Fxn library may be screened across functional assays to generate highly reproducible data that can be used to learn how the entire theoretical production fit sequence space maps to specific functions.

Figure 8D:
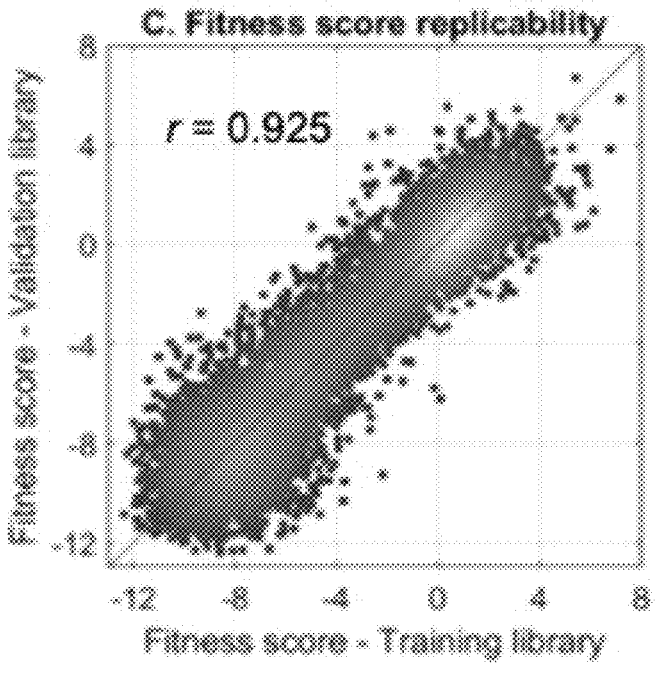
Figure 8E:
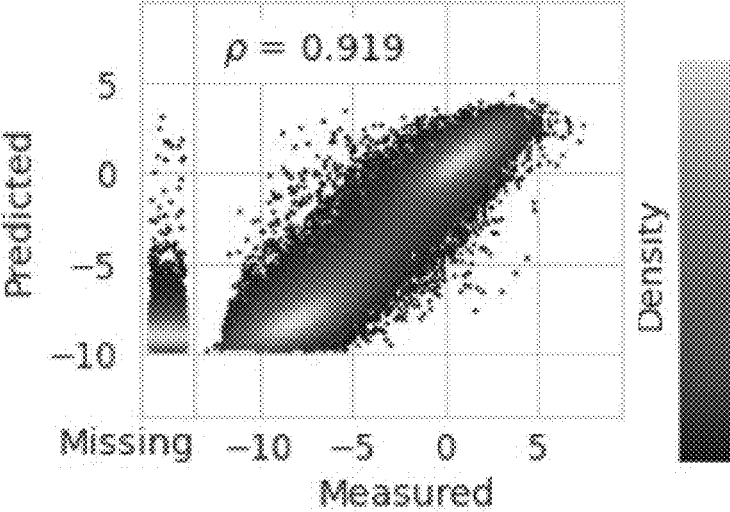

One advantage of Fit4Fxn libraries is that they may enable learning from true negatives, which is important for the unbiased training of ML models. This is in contrast with conventional NNN/NNK libraries, which are challenging to comprehensively sequence or quantitatively screen and are more highly biased (FIG. 8E). As an example, for a given library format (e.g., AAV9 7-mer insertion between residues 588-589), each functional ML model may only need to be trained once in order to learn the sequence-to-function map for an entire theoretical sequence space. In this way, ML models can be trained using Fit4Fxn libraries with different total diversities to accommodate functional screen requirements (e.g., more robust and quantitative assays could leverage higher diversity libraries). Additionally, these ML models can be combined to in silico search the entire production fit sequence space for variants that are optimized for multiple desired traits, including enhanced binding and transduction of target cells, low off-target binding, high production fitness, and almost any other trait that can be screened for with a high-throughput assay capable of generating reproducible data.

In addition, by selectively exploring the production fit sequence space, Fit4Fxn libraries described herein make efficient use of a restricted diversity library and are a useful stand-alone resource, independent of ML endeavors. As described in the Examples, applying the moderately sized (240K) Hammerhead library across several functional screening assays generated data that was more reproducible across replicates than data generated with random NNN/NNK 7-mer libraries. Indeed, within a single round of in vivo biodistribution screening, numerous variants were identified that were highly, and in some cases selectively, enriched in specific organs. This included several sequences that shared sequence motifs with previously described BBB-crossing variants AAV-PHP.B (TLAVPFK) (SEQ ID NO: 1) and AAV-PHP.B2 (SVSKPFL) (SEQ ID NO: 2) enriched across all brain and spinal cord replicates, suggesting that Fit4Fxn libraries described herein can be used to rapidly nominate candidates with reliable phenotypes (i.e., reproducible enrichment reduces the risk of false positives) for individual testing. The strength of the Fit4Fxn approach stems at least in part from the controlled library size, defined membership, and reduced fitness bias, not only the increased fitness relative to variants in a conventional library. Notably, Fit4Fxn libraries can also be custom designed to contain specific reference variants or to sample a more restrictive, even more high production fit subset of the sequence space.

The production fitness predictor described and validated herein can be used by researchers screening variants (e.g., AAV9 variants with 7-mer insertions (588-589 VP1 residues)) to score the production fitness of any sequence in silico. Researchers can use the model to score or rank individual variants of interest for production fitness, which may avoid spending resources and time on functional variants that cannot be easily manufactured. The fitness model also enables researchers without ML expertise to generate custom Fit4Fxn libraries with pre-specified sizes and production fitness distributions for downstream functional screening.

The Fit4Fxn approach offers multiple advantages to previously-developed machine learning-based strategies for multi-function optimization, which were limited in scope and/or generalizability (e.g., Bedbrook et al. 2019; Mason et al. 2019). For example, Mason et al. used ML models to predict antibodies with high expression fitness and maintained antigen specificity, but used in silico tools instead of trained regression models to optimize over additional functions, such as using online MHC Class II peptide binding predictors to predict immunogenicity of their generated antibodies (Mason et al. 2019).

Other studies have utilized ML classifiers to predict AAV production fitness as a means to generate diverse sets of fit variants, and have used these models to identify residues that are more or less permissive to mutations (Bryant et al. 2021; Marques et al. 2021). However, these models were not used to synthesize libraries that enabled better functional screens, nor were they used to identify single- or multi-function-optimized variants. Riesselman et al. also addressed the problem of generating a 'fit' library of nanobodies for subsequent screens by training an autoregressive generative model on the sequence of 1.2M functional nanobodies (Riesselman et al. 2019). While this approach is useful for generating a library of fit variants in a massive space, it does not give control over the fitness scale (i.e., it does not allow the user to generate variants of specific fitness scores), and it can introduce bias towards overrepresented variants in the training libraries. The resulting nanobody library was not demonstrated to be better than traditional libraries for functional screening.

The Fit4Fxn libraries described herein enable multi-function selection. As Fit4Fxn variants are predefined, they can be synthesized and applied across diverse functional assays at different times. The output of these assays will enable accumulation of sequence-to-function mappings that will accelerate multifunction fit variant identification. By contrast, the knowledge accumulation provided by Fit4Fxn libraries is not feasible with NNN/NNK 7-mer libraries as each iteration comprises a different composition of variants with little sequence overlap between libraries.

The Fit4Fxn approach of using moderately sized, low-bias libraries to generate accurate maps of sequence-to-fitness and -function relationships can be applied to any protein and assay where a sequence-function relationship is maintained during the screening process (e.g., affinity maturation, environmental sensitivity, stability). In some embodiments, the proteins being altered may be present on viral vectors other than AAV vectors, such as, but not limited to, retroviral vectors and lentiviral vectors. In some embodiments, assays may include, e.g., phage-, antibody-, single chain variable fragment (ScFv) antibody-, yeast-, peptide-, and/or ribosome-display approaches. In some embodiments, AAV vectors or portions thereof are screened for use in gene therapy. In other embodiments, antibodies or nanobodies or portions thereof (e.g., variable regions or CDRs) are screened for use in therapeutics, diagnostics, or other research applications. The Fit4Fxn approach has the potential to be widely useful for enhancing the affinity and specificity of, e.g., AAV capsids, antibodies, or other binding proteins to an array of targets useful for basic science, therapeutics, and diagnostics.

Aspects of the disclosure relate to identifying protein variants with desired traits. In some embodiments, desired traits may include one or more of: enhanced binding to target cells, enhanced transduction of target cells, reduced off-target binding, and/or increased production fitness. Similarly, in some embodiments, the described methods can be broadly employed in protein engineering to alter or improve the functional characteristics of enzymes, biotherapeutics, protein ligands and/or receptors, and signal transducing proteins/receptors. As one of ordinary skill in the art would appreciate, any other trait that can be screened for with a high-throughput assay capable of generating reproducible data may also be compatible with methods disclosed herein.

Figure 2:
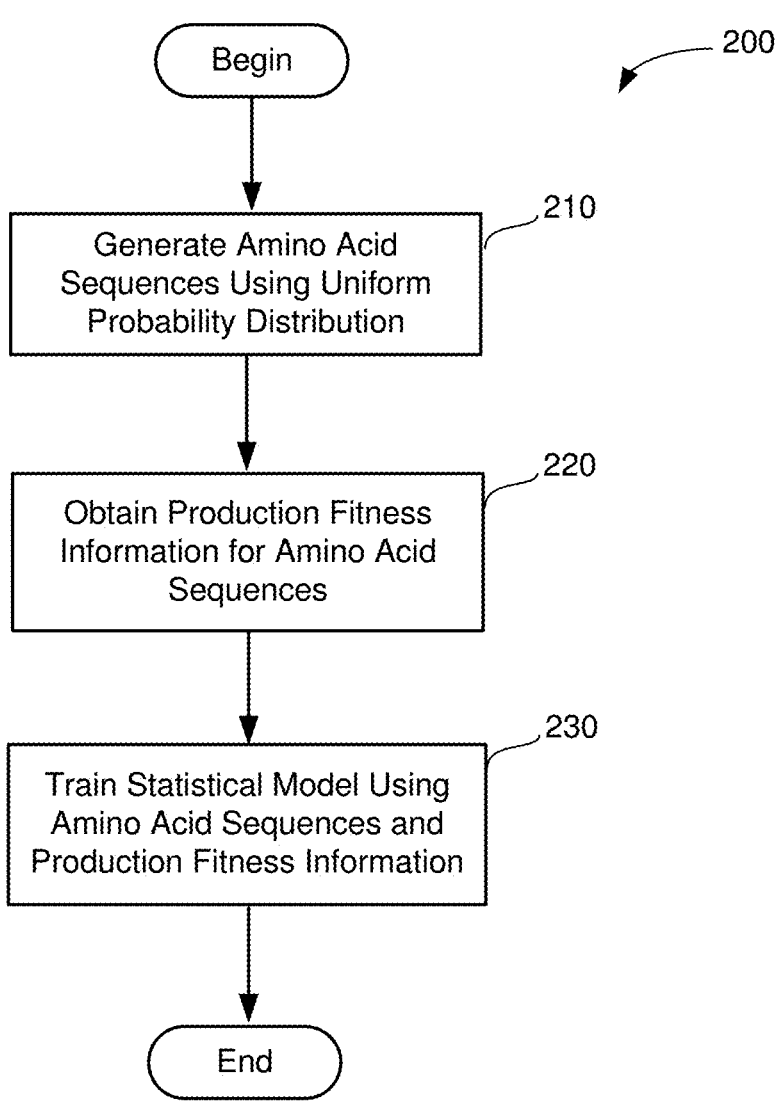
FIG. 2 is a flow chart of an illustrative process for training one or more statistical models to predict protein production fitness, using the technology described herein.

FIG. 2 is a flow chart of an illustrative process 200 for training one or more statistical models to predict protein production fitness, in accordance with some embodiments of the technology described herein. Process 200 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, training data 102 may be used as part of process 200 to train production fitness statistical model(s) 110.

Process 200 begins at act 210, where amino acid sequences are generated by using a uniform probability distribution over different types of amino acid sequences to randomly generate amino acid sequence variants of an initial amino acid sequence. In some embodiments, different types of amino acids occur in the amino acid sequences at approximately same proportions for at least some residue positions. In some embodiments, distributions of amino acid type across the amino acid sequences for at least some residue positions is substantially uniform. In some embodiments, each of at least some residue positions of the amino acid sequences have a substantially uniform distribution of amino acid type across the amino acid sequences.

In some embodiments, the training data includes at least 1,000, at least 2,000, at least 5,000, or at least 10,000 amino acid sequences. In some embodiments, the training data includes less than 20,000, less than 50,000, less than 100, 000, or less than 150,000 amino acid sequences. In some embodiments, the training data includes between 1,000 and 5,000, between 1,000 and 10,000, between 1,000 and 20,000, between 1,000 and 50,000, or between 1,000 and 150,000 amino acid sequences.

In some embodiments, the training data includes one or more nucleotide sequences encoding each of one or more of the amino acid sequences.

In some embodiments, each of the amino acid sequences comprises between 4-20 amino acids. In some embodiments, each of the amino acids comprises 7 amino acids.

In some embodiments, the initial amino acid sequence is a targeting peptide inserted into an adeno-associated virus (AAV) capsid). In some embodiments, the targeting peptide may confer cell binding and/or transduction activity to the AAV capsid. Further examples of AAV capsids and portions of AAV capsids are discussed in the "Adeno-associated virus (AAV) vectors" Section.

Next, process 200 proceeds to act 220, where production fitness information for the amino acid sequences are obtained. In some embodiments, obtaining the production fitness information involves screening the one or more protein variants for production fitness, and generating the production fitness information using results from screening the one or more protein variants for production fitness.

In some embodiments, the production fitness information includes production fitness measurements obtained for the amino acid sequences. In some embodiments, the production fitness information includes production fitness values having a multimodal distribution. The multimodal distribution may include a low production fitness component corresponding to amino acid sequences having low relative production fitness and a high production fitness component corresponding to amino acid sequences having high relative production fitness. In some embodiments, amino acid sequences associated with the high production fitness component have aspartic acid (D) occurring at a higher frequency than amino acid sequences associated with the low production fitness component. In some embodiments, amino acid sequences associated with the high production fitness component have glutamic acid (E) occurring at a higher frequency than amino acid sequences associated with the low production fitness component. In some embodiments, amino acid sequences associated with the high production fitness component have cysteine (C) occurring at a lower frequency than amino acid sequences associated with the low production fitness component. In some embodiments, amino acid sequences associated with the high production fitness component have tryptophan (W) occurring at a lower frequency than amino acid sequences associated with the low production fitness component.

Next process 200 proceeds to act 230, where the one or more statistical models are trained using the amino acid sequences and the production fitness information as training data. The one or more statistical models relates an input amino acid sequence to production fitness of a protein having the input amino acid sequence.

In some embodiments, the one or more statistical models comprise one or more regression models. In some embodiments, the one or more statistical models comprise one or more neural networks. In such embodiments, the one or more statistical models may have a recurrent neural network architecture. In some embodiments, the one or more statistical models may involve using a machine learning algorithm that implements a long short-term memory (LSTM) architecture. An example of a machine learning algorithm that implements a LSTM architecture is described in S. Hochreiter and J. Schmidhuber; Long Short-Term Memory, Neural Computation 9 (8): 1735-1780, 1997.

In some embodiments, process 200 further comprises storing the trained at least one statistical model on at least one computer-readable storage medium.

Figure 3:
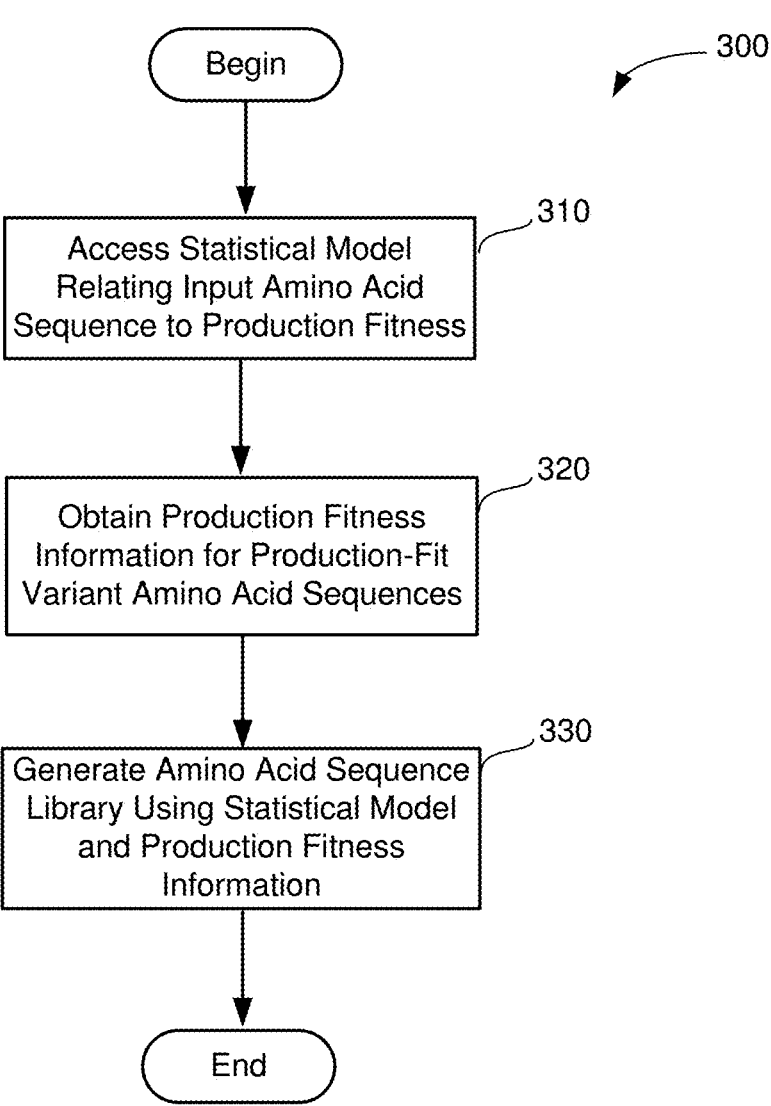
FIG. 3 is a flow chart of an illustrative process for generating a production-fit amino acid sequence library, using the technology described herein.

FIG. 3 is a flow chart of an illustrative process 300 for generating a production-fit amino acid sequence library, in accordance with the technology described herein. Process 300 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, production fitness statistical model(s) 110 may perform some or all of process 300 to generate a production-fit amino acid sequence library.

Process 300 begins at act 310, where one or more statistical models relating an input amino acid sequence to production fitness of a protein having the input amino acid sequence is accessed. In some embodiments, the one or more statistical models comprise one or more regression models. In some embodiments, the one or more statistical models comprise one or more neural networks. In such embodiments, the one or more statistical models may have a recurrent neural network architecture. In some embodiments, the one or more statistical models may involve using a machine learning algorithm that implements a long short-term memory (LSTM) architecture. An example of a machine learning algorithm that implements a LSTM architecture is described in S. Hochreiter and J. Schmidhuber; Long Short-Term Memory, Neural Computation 9 (8): 1735-1780, 1997.

Next, process 300 proceeds to act 320, where production fitness information for production-fit variant amino acid sequences for at least part of a protein is obtained. In some embodiments, the production fitness information corresponds to a mode of a distribution of production fitness data used to train the one or more statistical models. The production fitness information may correspond to a Gaussian distribution centered at the mode of the distribution for production fitness data used to train the at least one statistical model.

In some embodiments, the production fitness information corresponds to a high production fitness component of a distribution of production fitness values for amino acid sequences. The amino acid sequence library may have a range of production fitness values within the high production fitness component. The amino acid sequence library may have a distribution of production fitness values with a mean value equal to approximately a mean value of the high production fitness component. In some embodiments, each of the amino acid sequences of the amino acid sequence library has a value for production fitness above a threshold value.

Next, process 300 proceeds to act 330, where an amino acid sequence library having amino acid sequences with predicted production fitness in accordance with the production fitness information is generated using the one or more statistical models and the production fitness information. In some embodiments, generating the amino acid sequence library may include generating an initial set of amino acid sequence variants, using amino acid sequences in the initial set as input to the one or more statistical models to obtain values for production fitness, and selecting, based on the values for production fitness and the production fitness information, one or more of the amino acid sequences in the initial set to include in the amino acid sequence library. In some embodiments, the initial set of amino acid sequence variants comprises at least 50,000, at least 100,000, or at least 1,000,000 amino acid sequences. In some embodiments, the amino acid sequence library includes at least 10,000, at least 20,000, or at least 50,000 amino acid sequences.

In some embodiments, the one or more statistical models were trained using measured production fitness values having a multimodal distribution with modes, and the production fitness information corresponds to a mode of the multimodal distribution with highest value. In such embodiments, the amino acid sequences of the amino acid sequence library may have predicted production fitness values within a distribution centered at the mode of the multimodal distribution with highest value.

In some embodiments, each of the amino acid sequences of the amino acid sequence library includes between 4-20 amino acids. In some embodiments, each of the amino acid sequences of the amino acid sequence library includes 7 amino acids. In some embodiments, each of the amino acid sequences of the amino acid sequence library includes a number of amino acids and at least 60% of the amino acid sequences of the amino acid sequence library have a Hamming distance equal to the number of amino acids.

In some embodiments, the amino acid sequence is a targeting peptide inserted into an adeno-associated virus (AAV) capsid). In some embodiments, the targeting peptide may confer cell binding and/or transduction activity to the AAV capsid. Further examples of AAV capsids and portions of AAV capsids are discussed in the "Adeno-associated virus (AAV) vectors" Section.

In some embodiments, process 300 further includes manufacturing a protein having an amino acid sequence of the amino acid sequence library generated in act 330. Manufacturing the protein may include inserting a first polynucleotide encoding the targeting peptide into a second polynucleotide encoding the protein. In such embodiments, a portion of the second polynucleotide may be deleted. Manufacturing the protein may include substituting a first polynucleotide encoding the protein with a second polynucleotide encoding the targeting peptide. In such embodiments, a portion of the first polynucleotide may be deleted.

In some embodiments, process 300 further includes manufacturing, using an amino acid sequence of the amino acid sequence library generated in act 330, an adeno-associated virus (AAV) capsid having a targeting peptide sequence. Manufacturing the AAV capsid may include inserting a first polynucleotide encoding the targeting peptide into a second polynucleotide encoding the AAV capsid. In such embodiments, a portion of the second polynucleotide is deleted. Manufacturing the AAV capsid may include substituting a first polynucleotide encoding the AAV capsid with a second polynucleotide encoding the targeting peptide. In such embodiments, a portion of the first polynucleotide is deleted.

In some embodiments, process 300 further includes administering a therapy using an amino acid sequence of the amino acid sequence library generated in act 330. In some embodiments, process 300 further includes administering an adeno-associated virus (AAV) therapy where an AAV capsid of the AAV therapy includes an amino acid sequence of the amino acid sequence library.

In some embodiments, process 300 further includes accessing one or more second statistical model relating an input amino acid sequence to at least one characteristic of a protein other than protein production fitness having the input amino acid sequence, and selecting, using the amino acid sequence library and the one or more second statistical model, a subset of amino acid sequences from the amino acid sequence library. The one or more second statistical models may be trained using some or all of the amino acid sequences of the amino acid sequence library. In some embodiments, process 300 further includes training the one or more second statistical models using some or all the amino acid sequences of the amino acid sequence library as training data.

In some embodiments, process 300 further includes accessing one or more statistical models relating an input amino acid sequence to one or more protein characteristics other than protein production fitness having the input amino acid sequence, and determining, using the amino acid sequence library and the one or more statistical models, production-fit amino acid sequences having the one or more protein characteristics.

Figure 4A:
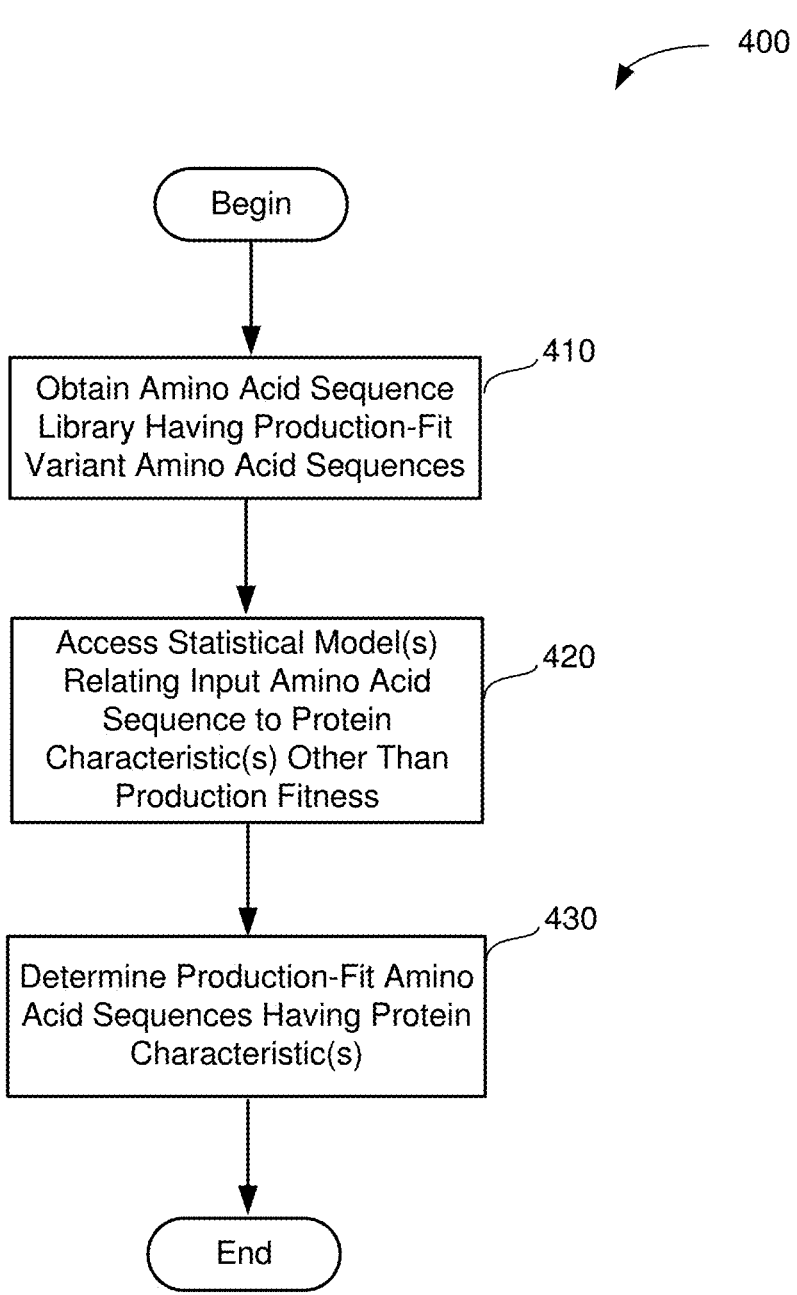
FIG. 4A is a flow chart of an illustrative process for identifying production-fit amino acid sequences with one or more other protein characteristics, using the technology described herein.

FIG. 4A is a flow chart of an illustrative process 400 for identifying production-fit amino acid sequences with one or more other protein characteristics, in accordance with some embodiments of the technology described herein. Process 400 may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, protein characteristic statistical model(s) 154 may perform some or all of process 400 to identify a multi-characteristic amino acid sequence library.

Process 400 begins at act 410, where an amino acid sequence library having production-fit variant amino acid sequences of at least a portion of a protein is obtained. The production-fit variant amino acid sequences may be obtained using process 300 shown in FIG. 3. In some embodiments, obtaining the production-fit variant amino acid sequences may include using a production fitness statistical model, such as statistical model 110, to obtain values for production fitness for an initial set of amino acid sequences. The initial set of amino acid sequences may be randomly generated using a uniform probability distribution. The production-fit variant amino acid sequences may be selected from the initial set of amino acid sequences based on the values for production fitness.

Next, process 400 proceeds to act 420, where one or more statistical models relating an input amino acid sequence to one or more protein characteristics other than protein production fitness for a protein having the input amino acid sequence is accessed. In some embodiments, the one or more statistical models includes a first statistical model for a first protein characteristic and a second statistical model for a second protein characteristic.

Examples of a protein characteristic include binding affinity to a target cell type, binding specificity to a target cell type, cell-type specific repulsion, biodistribution to one or more organs or tissues, and transduction of a target cell type. For these protein characteristics, examples of target cell type include liver cell, kidney cell, spleen cell, brain cell, spinal cord cell, heart cell, blood cell, and lung cell. Further examples of protein characteristics may be found in the "Targeting Peptides" Section, Example 4 in the "Examples" Section, and Example 5 in the "Examples" Section.

Next, process 400 proceeds to act 430, where production-fit amino acid sequences having the one or more protein characteristics are determined using the amino acid sequence library and the one or more statistical models. In some embodiments where the one or more statistical models includes a first statistical model for a first protein characteristic and a second statistical model for a second protein characteristic, determining the production-fit amino acid sequences having one or more protein characteristics may include using one or more amino acid sequences of the amino acid sequence library as input to the first statistical model to obtain one or more predicted values for the first protein characteristic and using one or more amino acid sequences of the amino acid sequence library as input to the second statistical model to obtain one or more predicted values for the second protein characteristic. A subset of amino acid sequences may be selected based on the one or more predicted values for the first protein characteristic and the one or more predicted values for the second protein characteristic. The subset of amino acid sequences may be included in a multi-characteristic amino acid sequence library, such as multi-characteristic amino acid sequences 156.

In some embodiments, each of the amino acid sequences of the production-fit amino acid sequences having the one or more protein characteristic includes between 4-20 amino acids. In some embodiments, each of the amino acid sequences includes 7 amino acids.

In some embodiments, determining the production-fit amino acid sequences having the at least one protein characteristic includes selecting, using the amino acid sequence library and the one or more statistical models, amino acid sequences from the amino acid sequence library.

In some embodiments, process 400 further involves screening one or more amino acid sequences of the amino acid sequence library for the one or more protein characteristic, and training the one or more statistical models based on results from the screening and the one or more amino acid sequences of the amino acid sequence library. This screening and training of the one or more statistical models may occur between acts 410 and 420 of process 400.

Determining the production-fit amino acid sequences at act 430 may involve selecting, using one or more second statistical models relating an input amino acid sequence to production fitness of a protein having the input amino acid sequence, a first set of amino acid sequences from among randomly generated amino acid sequences and selecting, using the one or more statistical models, a second set of amino acid sequences from among the first set of amino acid sequences. The second set of amino acid sequences may be included in a multi-characteristic amino acid sequence library, such as multi-characteristic amino acid sequences 156. In some embodiments, selecting the second set of amino acid sequences may involve determining values for one or more protein characteristics using the one or more statistical models and the first set of amino acid sequences, and selecting the second set of amino acid sequences based on the values for the one or more protein characteristics.

Examples of a protein characteristic include binding affinity to a target cell type, binding specificity to a target cell type, cell-type specific repulsion, biodistribution to one or more organs or tissues, and transduction of a target cell type. For these protein characteristics, examples of target cell type include liver cell, kidney cell, spleen cell, brain cell, spinal cord cell, heart cell, blood cell, and lung cell. Further examples of protein characteristics may be found in the "Targeting Peptides" Section, Example 4 in the "Examples" Section, and Example 5 in the "Examples" Section.

In some embodiments, the protein is an adeno-associated virus (AAV) capsid. Production-fit amino acid sequences having the one or more protein characteristics may correspond to targeting peptides within an AAV capsid. In some embodiments, the targeting peptide may confer cell binding and/or transduction activity to the AAV capsid. Further examples of AAV capsids and portions of AAV capsids are discussed in the "Adeno-associated virus (AAV) vectors" Section.

In some embodiments, process 400 further includes manufacturing a protein having an amino acid sequence of the production-fit amino acid sequences having the one or more protein characteristics. Manufacturing the protein may include inserting a first polynucleotide encoding a targeting peptide into a second polynucleotide encoding the protein. In such embodiments, a portion of the second polynucleotide may be deleted. Manufacturing the protein may include substituting a first polynucleotide encoding the protein with a second polynucleotide encoding a targeting peptide. In such embodiments, a portion of the first polynucleotide may be deleted.

In some embodiments, process 400 further includes manufacturing, using an amino acid sequence of the amino acid sequence library, an adeno-associated virus (AAV) capsid including the amino acid sequence. Manufacturing the AAV capsid may include inserting a first polynucleotide encoding a targeting peptide into a second polynucleotide encoding the AAV capsid. In such embodiments, a portion of the second polynucleotide is deleted. Manufacturing the AAV capsid may include substituting a first polynucleotide encoding the AAV capsid with a second polynucleotide encoding a targeting peptide. In such embodiments, a portion of the first polynucleotide is deleted.

In some embodiments, process 400 further includes administering a therapy using an amino acid sequence of the production-fit amino acid sequences having the one or more protein characteristics. In some embodiments, process 400 further includes administering an adeno-associated virus (AAV) therapy where an AAV capsid of the AAV therapy includes an amino acid sequence of the production-fit amino acid sequences having the one or more protein characteristics.

Figure 4B:
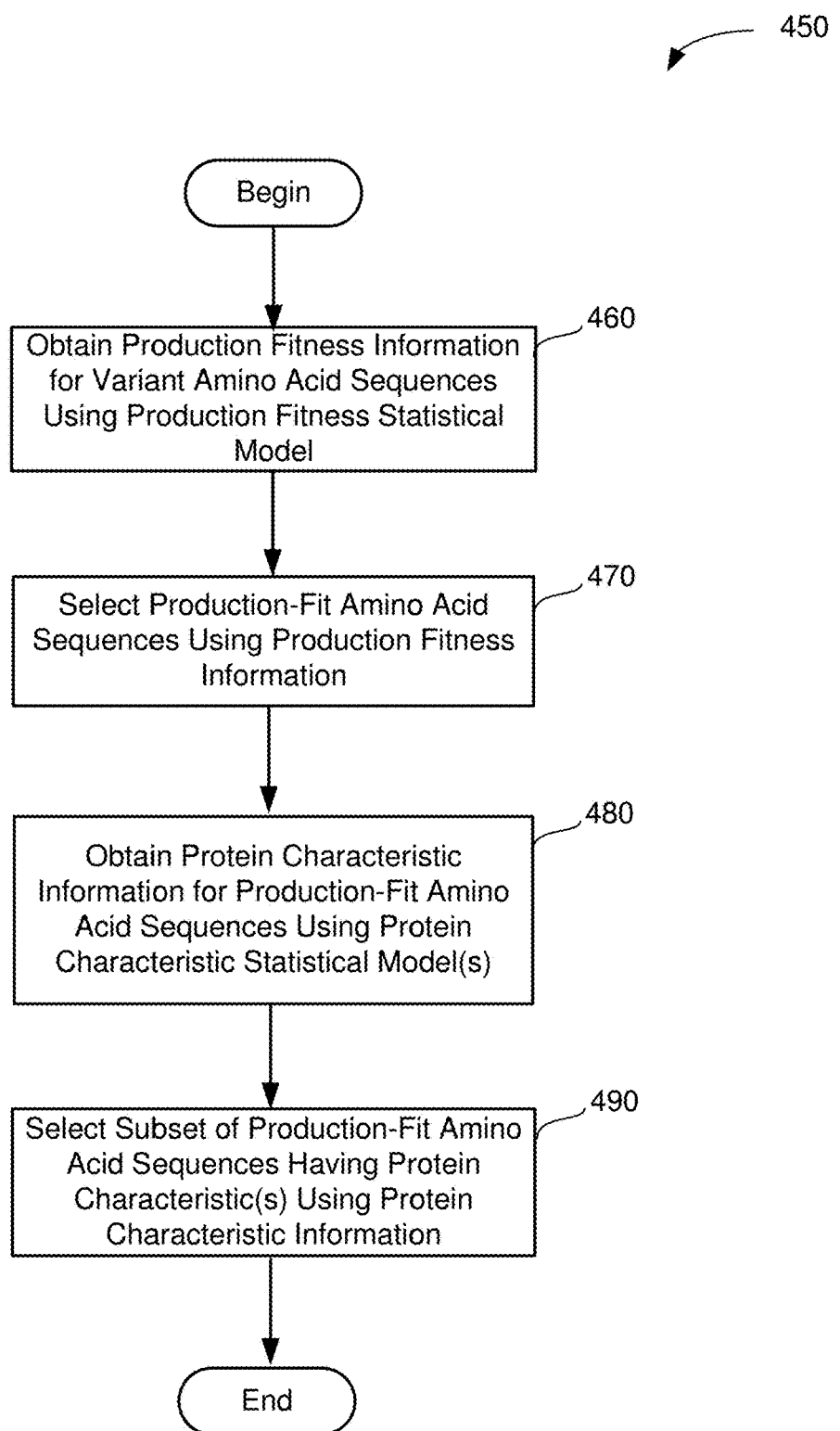
FIG. 4B is a flow chart of an illustrative process for identifying production-fit amino acid sequences with one or more other protein characteristics, using the technology described herein.

FIG. 4B is a flow chart of an illustrative process 450 for identifying production-fit amino acid sequences with one or more other protein characteristics, in accordance with some embodiments of the technology described herein. Process 450, may be performed on any suitable computing device(s) (e.g., a single computing device, multiple computing devices co-located in a single physical location or located in multiple physical locations remote from one another, one or more computing devices part of a cloud computing system, etc.), as aspects of the technology described herein are not limited in this respect. In some embodiments, production fitness statistical model(s) 110 and protein characteristic statistical model(s) 154 may perform some or all of process 450 to identify a multi-characteristic amino acid sequence library.

Process 400 begins at act 410, where production fitness information for variant amino acid sequences using a production fitness statistical model is obtained. For example, production fitness statistical model(s) 110 may be used to obtain production fitness information. The production fitness information may include values for the variant amino acid sequences. The production fitness statistical model may be trained using process 200 shown in FIG. 2. The values may be predicted values for production fitness output by the production fitness statistical model. In some embodiments, each of the variant amino acid sequences may a value obtained by using the variant amino acid sequence as input to the production statistical model. In some embodiments, the variant amino acid sequences may be randomly generated using a uniform probability distribution. In such embodiments, the variant amino acid sequences may have a substantially uniform distribution of amino acid type across the variant amino acid sequences.

Process 450 begins at act 460, where production fitness information for variant amino acid sequences using a production fitness statistical model is obtained. Next, process 450 proceeds to act 470, where production-fit amino acid sequences are selected from among the variant amino acid sequences using the production fitness information. In embodiments where the production fitness information includes values for the variant amino acid sequences, selecting amino acid sequences from among the variant amino acid sequences may be based on these values. For example, an amino acid sequence having a production fitness value above a threshold value may be identified as being a production-fit amino acid sequence and selected as part of act 470.

Next, process 450 proceeds to act 480, where protein characteristic information for the production-fit amino acid sequences is obtained using protein characteristic model(s). The protein characteristic information may include one or more protein characteristics other than production fitness for the production-fit amino acid sequences. Protein characteristic statistical model(s) 154 may be used to obtain protein characteristic information for the production-fit amino acid sequences. For example, a production-fit amino acid sequence may be used as an input to a protein characteristic model 154 to obtain a value for a protein characteristic of the production-fit amino acid sequence as an output.

Examples of a protein characteristic include binding affinity to a target cell type, binding specificity to a target cell type, cell-type specific repulsion, biodistribution to one or more organs or tissues, and transduction of a target cell type. For these protein characteristics, examples of target cell type include liver cell, kidney cell, spleen cell, brain cell, spinal cord cell, heart cell, blood cell, and lung cell. Further examples of protein characteristics may be found in the "Targeting Peptides" Section, Example 4 in the "Examples" Section, and Example 5 in the "Examples" Section.

Multiple protein characteristic statistical models may be used to obtain protein characteristic information for the production-fit amino acid sequences. In such embodiments, a first statistical model may be used for a first protein characteristic and a second statistical model may be used for a second protein characteristic. Protein characteristic information may include values for the first protein characteristic and the second protein characteristic for the production-fit amino acid sequences. In some embodiments, a value for the first characteristic and a value for the second characteristic may be obtained for each of the production-fit amino acid sequences. For example, a production-fit amino acid sequence may be input to the first statistical model to obtain a predicted value of the first protein characteristic for the amino acid sequence. Similarly, the production-fit amino acid sequence may be input to the second statistical model to obtain a predicted value of the second protein characteristic for the amino acid sequence.

Next, process 450 proceeds to act 490, where a subset of the production-fit amino acid sequences having one or more protein characteristics other than production fitness may be selected using the protein characteristic information obtained in act 480. The subset of amino acid sequences may be included in a multi-characteristic amino acid sequence library, such as multi-characteristic amino acid sequences 156. In embodiments where protein characteristic information includes values for multiple protein characteristics, selecting the subset of the production-fit amino acid sequences may be based on the values. As an example, it may be desired to include amino acid sequences in the subset that have a value for a first protein characteristic above a first threshold value and a value for a second protein characteristic below a second threshold value. Selecting the subset of production-fit amino acid sequences involves selecting amino acid sequences that have a value for the first protein characteristic above the first threshold value and a value for the second protein characteristic below the second threshold value.

In some embodiments, each of the amino acid sequences of the production-fit amino acid sequences includes between 4-20 amino acids. In some embodiments, each of the production-fit amino acid sequences includes 7 amino acids.

In some embodiments, the protein is an adeno-associated virus (AAV) capsid. Production-fit amino acid sequences having the one or more protein characteristics may corre-spond to targeting peptides within an AAV capsid. In some embodiments, the targeting peptide may confer cell binding and/or transduction activity to the AAV capsid. Further examples of AAV capsids and portions of AAV capsids are discussed in the "Adeno-associated virus (AAV) vectors" Section.

In some embodiments, process 450 further includes manufacturing a protein having an amino acid sequence of the subset selected in act 490. Manufacturing the protein may include inserting a first polynucleotide encoding a targeting peptide into a second polynucleotide encoding the protein. In such embodiments, a portion of the second polynucleotide may be deleted. Manufacturing the protein may include substituting a first polynucleotide encoding the protein with a second polynucleotide encoding a targeting peptide. In such embodiments, a portion of the first polynucleotide may be deleted.

In some embodiments, process 450 further includes administering a therapy using an amino acid sequence of the of the subset selected in act 490. In some embodiments, process 400 further includes administering an adeno-associated virus (AAV) therapy where an AAV capsid of the AAV therapy includes an amino acid sequence of the production-fit amino acid sequences having the one or more protein characteristics.

Figure 5:
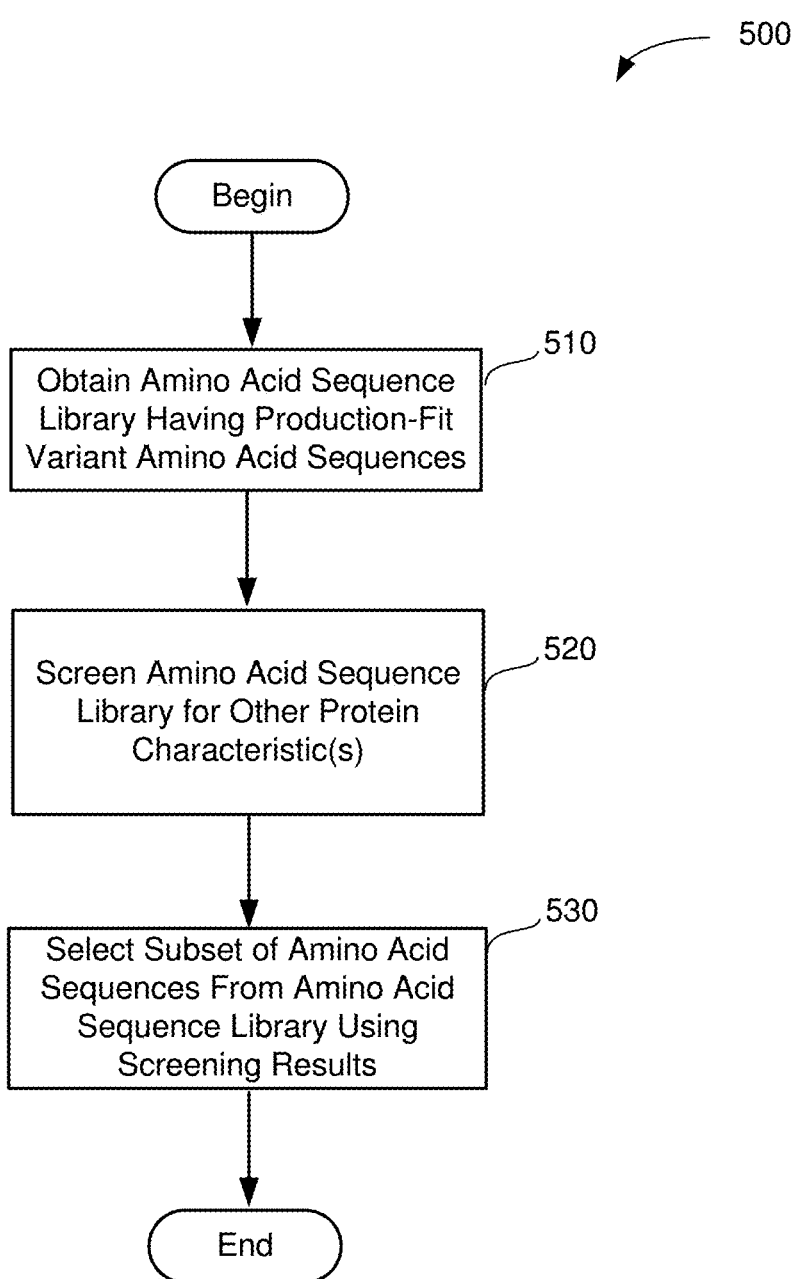
FIG. 5 is a flow chart of an illustrative process for identifying amino acid sequences having high production fitness and one or more other protein characteristics, using the technology described herein.

FIG. 5 is a flow chart of an illustrative process 500 for identifying amino acid sequences having high production fitness and one or more protein characteristics.

Process 500 begins at act 510, where an amino acid sequence library having production-fit variant amino acid sequences is obtained. In some embodiments, each of the amino acid sequences of the production-fit amino acid sequence library comprises between 4-20 amino acids. In some embodiments, each of the amino acid sequences comprises 7 amino acids. Further examples of generating proteins comprising variant targeting peptides may be found in section "Targeting Peptides" below.

Next, process 500 proceeds to act 520, where the amino acid sequence library is screened for other protein characteristics. In some embodiments, the one or more protein characteristics are selected from a group consisting of: binding affinity to a target cell type, binding specificity to a target cell type, cell-type specific repulsion, biodistribution to one or more organs or tissues, and transduction of a target cell type. In some embodiments, the one or more protein characteristics includes binding affinity to at least one cell type selected from a group consisting of: liver cell, kidney cell, spleen cell, brain cell, spinal cord cell, heart cell, blood cell, and lung cell. In some embodiments, the one or more protein characteristics includes binding specificity to at least one cell type selected from a group consisting of: liver cell, kidney cell, spleen cell, brain cell, spinal cord cell, heart cell, blood cell, and lung cell. In some embodiments, the one or more protein characteristics includes transduction of at least one cell type selected from a group consisting of: liver cell, kidney cell, spleen cell, brain cell, spinal cord cell, heart cell, blood cell, and lung cell. Further examples of protein characteristics may be found in section "Targeting Peptides," Example 4 in the examples, and Example 5 in the examples.

Next, process 500 proceeds to act 530, where a subset of amino acid sequences from the amino acid sequence library is selected using the results of act 520. In some embodiments, each of the amino acid sequences in the subset of amino acid sequences comprises between 4-20 amino acids. In some embodiments, each of the amino acid sequences in the subset of amino acid sequences comprises 7 amino acids.

In some embodiments, process 500 further comprises manufacturing, using an amino acid sequence in the subset of amino acid sequences selected in act 530, a protein having the amino acid sequence. Manufacturing the protein may include inserting a first polynucleotide encoding a targeting peptide into a second polynucleotide encoding the protein. In such embodiments, a portion of the second polynucleotide may be deleted. Manufacturing the protein may include substituting a first polynucleotide encoding the protein with a second polynucleotide encoding a targeting peptide. In such embodiments, a portion of the first polynucleotide may be deleted. Further examples of manufacturing may be found in section "Pharmaceutical Compositions" below.

In some embodiments, process 500 further comprises manufacturing, using an amino acid sequence in the subset of amino acid sequences, an adeno-associated virus (AAV) capsid having the amino acid sequence. Further examples of production and uses of AAV capsids may be found in section "Adeno-associated virus (AAV) vectors" below.

In some embodiments, process 500 further comprises administering a therapy using a protein having an amino acid sequence in the subset of amino acid sequences selected in act 530. Further examples of administering a therapy may be found in section "Gene Therapy Methods" below.

In some embodiments, process 500 further comprises administering an adeno-associated virus (AAV) therapy, wherein an AAV capsid of the AAV therapy includes an amino acid sequence in the subset of amino acid sequences selected in act 530.

Adeno-Associated Virus (AAV) Vectors

As demonstrated in the Examples section, the Fit4Fxn approach can be used to identify adeno-associated virus (AAV) vectors with enhanced features for use in gene therapy. AAV vectors described herein can be used to deliver a nucleic acid encoding a protein of interest to a subject, including, e.g., delivery to specific organs or to the central nervous system (CNS) of a subject. AAV vectors are described further in U.S. Pat. No. 9,585,971, US 2017/0166926, and WO2020/160337, which are incorporated by reference herein in their entireties.

AAV refers to a replication-deficient Dependoparvovirus within the Parvoviridae genus of viruses. AAV can be derived from a naturally occurring virus or can be recombinant. AAV can be packaged into capsids, which can be derived from naturally occurring capsid proteins or recombinant capsid proteins. The single-stranded DNA genome of AAV includes inverted terminal repeat (ITRs), which are involved in integrating the AAV DNA into the host cell genome. In some embodiments, AAV integrates into a host cell genome, while in other embodiments, AAV is non-integrating. AAV vectors can comprise: one or more ITRs, including, for example a 5' ITR and/or a 3' ITR; one or more promoters; one or more nucleic acid sequences encoding one or more proteins of interest; and/or additional posttranscriptional regulator elements. AAV vectors described herein can be prepared using standard molecular biology techniques known to one of ordinary skill in the art, as described, for example, in Sambrook el al. (Molecular Cloning: A Laboratory Manual. Cold Spring Harbor Laboratory Press, N.Y. (2012)).

AAV vectors described herein can include sequences from any known organism and can include synthetic sequences. AAV vector sequences can be modified in any way known to one of ordinary skill in the art, such as by incorporating insertions, deletions or substitutions, and/or through the use of posttranscriptional regulatory elements, such as promoters, enhancers, and transcription and translation terminators, such as polyadenylation signals. AAV vectors can also include sequences related to replication and integration. In some embodiments, AAV vectors include a shuttle element for replication and integration.

AAV vectors can include any known AAV serotype, including, for example, AAV1, AAV2, AAV3, AAV4, AAV5, AAV6, AAV7, AAV8, AAV9, AAV10, and AAV11. In some embodiments, the AAV serotype is AAV9. Clades of AAV viruses are described in, and incorporated by reference, from Gao et al. (2004) J. Virol. 78 (12): 6381-6388.

AAV vectors of the present disclosure may comprise or be derived from any natural or recombinant AAV serotype. In some embodiments, the AAV vector may utilize or be based on an AAV serotype described in WO 2017/201258A1, the contents of which are incorporated herein by reference in its entirety, such as, but not limited to, AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu. 12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AA Vhu.7, AAVhu.9, AAVhu.10, AAVhu. 11, AAVhu.13, AAVhu. 15, AAVhu. 16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AA Vhu.60, AAVhu.61, AAVhu.63, AAVhu.64, AAVhu.66, AAVhu.67, AAVhu. 14/9, AAVhu.t 19, AAVrh.2, AAVrh.2R, AAVrh.8, AAVrh.8R, AAVrh.10, AAVrh.12, AAVrh. 13, AAVrh. 13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AA Vrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AA VhEr2.16, AA VhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu. 19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-c5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAV-PHP.B (PHP.B), AAV-PHP.A (PHP.A), G2B-26, G2B-13, TH1.1-32 and/or TH1.1-35, and variants thereof.

AAV vectors can comprise targeting sequences (e.g., 7-mer sequences) capable of directing the AAV vectors to specific environments within a subject, including, in some embodiments, directing the AAV vectors across the blood-brain barrier in a subject. In some embodiments, the targeting sequence is inserted into the capsid protein of the AAV vector. The targeting sequence can be inserted into any region of the capsid protein. In some embodiments, methods disclosed herein are used to identify AAV targeting sequences with improved functionality.

Aspects of the disclosure relate to AAV capsid proteins. AAV capsid proteins described herein may have a sequence that is different from the corresponding wild type AAV capsid protein sequence or is different from a reference AAV capsid protein sequence. An AAV capsid protein can include an insertion, deletion, or substitution of one or more nucleotides or one or more amino acids relative to the corresponding wild type AAV capsid protein sequence or relative to a reference AAV capsid protein sequence. The insertion, deletion, or substitution of one or more nucleotides or one or more amino acids can be at the 5' end, the 3' end and/or internally within the capsid sequence.

The nucleotide sequence of an AAV capsid protein can be at least about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or more than 99%, inclusive of all ranges and subranges therebetween, identical to a wild type AAV capsid nucleotide sequence or a reference AAV capsid nucleotide sequence. The protein sequence of an AAV capsid protein can be at least about 50%, about 55%, about 60%, about 65%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or more than 99%, inclusive of all ranges and subranges there between, identical to a wild type AAV capsid protein sequence or a reference AAV capsid protein sequence.

Also disclosed herein are libraries of AAV capsid proteins, such as AAV9 capsid proteins. As used herein, a "library" of AAV capsid proteins refers to a collection of at least two AAV capsid proteins. In some embodiments, at least one of the AAV capsid proteins within the library includes an insertion of a targeting sequence (e.g., a 7-mer). In some embodiments, methods disclosed herein are used to identify AAV capsid protein targeting sequences with improved functionality.

Targeting sequences can, in some embodiments, increase biodistribution of an AAV to various organs and organ tissue in an animal, and/or increase transduction efficiency of an AAV across the blood-brain barrier in a subject relative to an AAV that does not contain the targeting sequence. In some embodiments, improved biodistribution to one or more of the following is improved using a targeting sequence: liver, kidney, spleen, serum, brain, spinal cord, heart, and/or lung.

For example, the inclusion of one or more targeting sequences in an AAV can result in an increase in biodistribution and transduction efficiency by at least 5%, 10%, 20%, 30%, 40%, 50%, 60%, 70%, 80%, 90%, 100%, 1.5-fold, 2-fold, 2.5-fold, 3-fold, 3.5-fold, 4-fold, 4.5-fold, 5-fold, 5.5-fold, 6-fold, 6.5-fold, 7-fold, 7.5-fold, 8-fold, 10-fold, 20-fold, 30-fold, 40-fold, 50-fold, 60-fold, 70-fold, 80-fold, 90-fold, 100-fold, or more than 100-fold, including all values in between, relative to an AAV that lacks the targeting sequence. In some embodiments, the transduction efficiency is increased for transducing AAV to the blood-brain barrier. In some embodiments, the transduction efficiency is increased for transducing AAV to the CNS. In some embodiments, the transduction efficiency is increased for transducing AAV to the PNS. In some embodiments, the transduction efficiency is increased for transducing AAV to the heart. In some embodiments, the transduction efficiency is increased for transducing AAV to cardiomyocytes, sensory neurons, dorsal root ganglia, visceral organs, or any combination thereof. In some embodiments, the transduction efficiency is increased for transducing AAV to any target environment suitable for the delivery of AAV vectors. In some embodiments, biodistribution is increased to one or more of: serum, liver, spleen, kidney, heart, lung, spinal cord, and/or brain.

In some embodiments, improved functionality includes enhanced cross-species hepatocyte tropism. In some embodiments, improved functionality includes both enhanced cross-species hepatocyte tropism and increased production fitness. Previous efforts to develop capsids with improved human hepatocyte transduction have led to enhancements that are selective for human cells, but not mouse cells (Lisowski et al., 2014; Paulk et al., 2018; Qian et al., 2021). There is a need for improved methods to find AAV capsids that work across species to facilitate more reliable preclinical efficacy and safety testing. As described in the Examples, methods described herein were applied to identify capsids with cross-species transduction enhancements by screening for binding and transduction of the human hepatocellular carcinoma cell line (HepG2), and liver-directed biodistribution in mice. Methods described herein were able to identify the intersection of variants that are optimized for all three traits as well as for high production fitness. Thus, methods described herein can predict rare capsid variants that exhibit high production fitness and cross species tropism enhancements (e.g., human cells versus mouse animal model).

In some embodiments, an AAV9 capsid protein, or a library of AAV9 capsid proteins, is provided in which the AAV9 genome contains the viral replication gene (rep) and capsid gene (cap) that have been modified so as to not prevent the replication of the virus under conditions in which it could normally replicate. In some embodiments, an AAV9 capsid protein, or a library of AAV9 capsid proteins, is provided in which the AAV9 genome contains an engineered cap gene. In some embodiments, an AAV9 capsid protein, or a library of AAV9 capsid proteins, is provided in which the AAV9 genome contains the rep cap genes are flanked by ITRs. In some embodiments, an AAV genome contains the cap gene and contains rep gene sequences that are involved in regulating expression and/or splicing of the cap gene. In some embodiments, a capsid gene recombinase recognition sequence is provided, optionally with flanking ITRs.

Libraries of AAV capsid proteins, such as AAV9 capsid proteins, described herein, can be used to select for AAV capsid proteins that exhibit, e.g.: enhanced targeting to specific cells or organs; evasion of immunity; enhancement of cross species tropism, increased production fitness, efficiency at homologous recombination; efficiency of conversion of the single stranded AAV genome to a double stranded DNA genome within a cell; and/or increased conversion of an AAV genome to a persistent, circularized form within the cell.

Targeting Peptides

Aspects of the disclosure relate to targeting peptides that can direct AAV, e.g., to a specific target environment. In some embodiments, the target environment is a cell (e.g., neuron). In some embodiments, the target environment is serum, liver, spleen, kidney, heart, lung, spinal cord, brain, neurons, astrocytes, cardiomyocytes, or a combination thereof. In some embodiments, the target environment is an organ (e.g., heart, brain). In some embodiments, the targeting peptide directs AAV to the central nervous system (CNS) of a subject. The CNS includes, e.g., brain tissue, nerves (e.g., optic nerves or cranial nerves), and fluid (e.g., cerebrospinal fluid). In some embodiments, the targeting peptide directs AAV to the peripheral nervous system (PNS) of a subject. Targeting peptides can be conjugated to other components, such as a nanoparticle or a viral capsid protein.

Targeting peptides, as described herein, may be various lengths. In some embodiments, the targeting peptide comprises 4 amino acids (e.g., 4-mer). In some embodiments, the targeting peptide comprises 5 amino acids (e.g., 5-mer). In some embodiments, the targeting peptide comprises 6 amino acids (e.g., 6-mer). In some embodiments, the targeting peptide comprises 7 amino acids (e.g., 7-mer). In some embodiments, the targeting peptide comprises 8 amino acids (e.g., 8-mer). In some embodiments, the targeting peptide comprises 9 amino acids (e.g., 9-mer). In some embodiments, the targeting peptide comprises 10 amino acids (e.g., 10-mer). In some embodiments, the targeting peptide comprises less than 4 or more than 10 amino acids. In some embodiments, the targeting peptide can be any length comprising any numbers of amino acids that are suitable for the incorporation into AAV vectors.

Targeting peptides, as described herein, may be charged or uncharged. In some embodiments, the targeting peptide is positively charged. In some embodiments, the targeting peptide is negatively charged. In some embodiments, the targeting peptide is neutrally charged. In some embodiments, the targeting peptide is uncharged.

Targeting peptides, as described herein, may comprise positively charged amino acids and negatively charged amino acids in various ratios. In some embodiments, the targeting peptide comprises positively charged amino acids and negatively charged amino acids in a 0:1 or 1:0 ratio. In some embodiments, the targeting peptide comprises positively charged amino acids and negatively charged amino acids in a 1:1, 2:1, 3:1, or 4:1 ratio. In some embodiments, the targeting peptide comprises positively charged amino acids and negatively charged amino acids in a 1:2, 1:3, or 1:4 ratio. In some embodiments, the targeting peptide comprises at least one negatively charged amino acids (e.g., arginine) and at least one hydrophobic amino acid residue (e.g., leucine). In some embodiments, the targeting peptide comprises two arginine residues and two leucine residues.

Targeting peptides can be fused to or inserted into longer peptides. In some embodiments, targeting peptides are isolated. In some embodiments, targeting peptides are not naturally occurring.

Targeting peptides are further described in WO2020/160337, which is incorporated by reference herein in its entirety.

In some embodiments, a targeting peptide does not comprise or consist of a sequence disclosed in WO2015/038958 or WO2017/100671, which are incorporated by reference herein in their entireties.

Methods provided herein, in some embodiments, are useful for identifying targeting peptides, or AAV capsid proteins harboring targeting peptides, that bind proteins of interest. In some embodiments, the protein of interest is ectopically expressed on cells. In some embodiments, the protein of interest is a recombinant protein. In some embodiments, the protein of interest is endogenously expressed in a cell. In some embodiments, methods provided herein are useful for identifying AAV capsids proteins that cross specific barriers (e.g., blood-brain barrier or gut epithelium). In some embodiments, methods provided herein are useful for identifying AAV9 capsids proteins.

Targeting peptides described herein can be identified by incubating a candidate targeting peptide (e.g., an AAV capsid protein containing a targeting peptide) with a protein; and selecting the targeting peptide if it binds to the protein. In some embodiments, the protein is expressed in a cell, such as on the surface of the cell, and binding of the targeting peptide (e.g., an AAV capsid protein containing a targeting peptide) to the cell that expresses the protein on the surface of the cell is detected. Such binding assays may be performed with purified protein or with cells naturally expressing or transfected to express a protein. Binding assays may be performed in various formats, including in vitro, or in cell culture, and including high-throughput formats. In some embodiments, a targeting peptide (e.g., an AAV capsid protein containing a targeting peptide) described herein can be further evaluated by monitoring its ability to mediate transcytosis across the blood-brain barrier.

In some embodiments, a targeting peptide (e.g., within an AAV capsid protein) specifically binds to a protein of interest. Methods to determine such specific binding are well known in the art. A targeting peptide is said to exhibit "specific binding" or to "specifically bind to a protein" if it reacts or associates more frequently, more rapidly, with greater duration and/or with greater affinity with a particular protein than it does with alternative proteins. A targeting peptide that specifically binds to a first protein may or may not specifically or preferentially bind to a second protein.

As such, "specific binding" or "preferential binding" does not necessarily require (although it can include) exclusive binding. Generally, but not necessarily, reference to binding means preferential binding.

An AAV capsid protein is said to exhibit "specific binding" or to "specifically bind" to a protein if it reacts or associates more frequently, more rapidly, with greater duration and/or with greater affinity with the protein than it does with alternative proteins of interest. An AAV capsid protein that specifically binds to a protein may or may not specifically or preferentially bind to the protein.

For example, methods disclosed herein can comprise providing an AAV capsid protein, incubating the AAV capsid protein with a cell that recombinantly expresses a protein of interest attached to the surface of the cell, and selecting the AAV capsid protein if it specifically binds to the protein of interest attached to the surface of the cell.

In some embodiments, methods disclosed herein can comprise providing an AAV capsid protein, incubating the AAV capsid protein with a protein of interest that was purified from cells expressing the protein of interest, and selecting the AAV capsid protein if it specifically binds to the protein of interest.

In some embodiments, methods comprise screening for an AAV capsid protein that can bind to a protein of interest, comprising providing a library of AAV capsid proteins, incubating the library of AAV capsid proteins with a cell that recombinantly expresses a protein of interest attached to the surface of the cell, isolating an AAV capsid protein that binds to the cells that recombinantly express the protein of interest on the cell surface, and identifying the sequence of the isolated AAV capsid protein.

In some embodiments, methods comprise screening for an AAV capsid protein that can bind to a protein of interest, comprising providing a library of AAV capsid proteins, incubating the library of AAV capsid proteins with a protein of interest (e.g., a recombinant protein of interest or a protein of interest purified from cells expressing the protein of interest), isolating an AAV capsid protein that binds to the protein of interest, and identifying the sequence of the isolated AAV capsid protein.

The sequence of the isolated AAV capsid proteins may be identified using any sequencing methods known in the art. In some embodiments, AAV capsid proteins are sequenced using short read sequencing technology. In some embodiments, AAV capsid proteins are sequenced using long read sequencing technology. In some embodiments, AAV capsid proteins are sequenced using next-generation sequencing (NGS) technology or whole genome sequencing (WGS) technology.

Methods provided herein may be performed using any type of cell. Examples of cells include, but are not limited to, mammalian cells, primate cells, human cells, rodent cells, yeast cells, and bacterial cells. Examples of mammalian cells include, but are not limited to, CHO (Chinese Hamster Ovary), VERO, HeLa, CVI, COS, COS-7, BHK (baby hamster kidney), MDCK, CI 27, PC 12, HEK-293, PER C6, NSO, WI38, R1610, BALBC/3T3, HAK, SP2/0, P3x63-Ag3.653, BFA-IcIBPT, RAJI, and 293 cells.

Methods provided herein may be performed using purified endogenous proteins, which may be tagged using any tag known in the art, such as AviTag, C-tag, Calmodulin-tag, E-tag, FLAG, HA, poly-HIS, MYC, NE, Rho1D4, S-tag, SBP, Softag, Spot-tag, T7-tag, TC, Ty, V5, VSV, Xpress, Isopeptag, SpyTag, SnoopTag, DogTag, SdyTag, BCCP, GST, GFP, Halo, SNAP, CLIP, Maltose binding protein (MBP), Nus-tag, Thioredoxin-tag, Fc-tag, CRDSAT, SUMO-tag, B2M-tag. The recombinant proteins can be purified from any cell type.

Gene Therapy Methods

Methods provided herein, in some embodiments, are useful for delivering a nucleic acid (or another biologic, such as an antibody) to a target environment (e.g., serum, liver, spleen, kidney, heart, lung, spinal cord, brain, neurons, astrocytes, cardiomyocytes, or a combination thereof) of a subject in need. In some embodiments, methods for delivering a nucleic acid (or another biologic, such as an antibody) to a target environment comprise delivering the nucleic acid (or another biologic, such as an antibody) to the heart, the nervous system, or a combination thereof. In some embodiments, methods for delivering a nucleic acid (or another biologic, such as an antibody) to a target environment comprise delivering the nucleic acid (or another biologic, such as an antibody) to neurons, astrocytes, cardiomyocytes, or a combination thereof. In some embodiments, methods for delivering a nucleic acid (or another biologic, such as an antibody) to a target environment comprise delivering the nucleic acid (or another biologic, such as an antibody) to a hematopoietic lineage, such as an immune cell. Methods of use of AAV vectors are described further in U.S. Pat. No. 9,585,971, US 2017/0166926, and WO2020/160337, which are incorporated by reference herein in their entireties.

In some embodiments, methods for delivering a nucleic acid to a target environment of a subject in need comprise providing a composition comprising an AAV as described herein, and administering the composition to the subject. In some embodiments, methods for delivering a nucleic acid to a target environment of a subject in need thereof comprise providing a composition comprising an AAV comprising (i) a capsid protein, and (ii) a nucleic acid (or another biologic, such as an antibody) to be delivered to the target environment of the subject, and administering the composition to the subject.

Methods provided herein, in some embodiments, are useful for treating a disorder or defect in a subject. In some embodiments, the methods as described herein comprise delivering a protein, RNA, or DNA to a target environment of the subject. In some embodiments, the methods as described herein comprise administering an adeno-associated virus (AAV) vector to a target environment of the subject. In some embodiments, the AAV vector comprises a nucleic acid molecule that encodes a therapeutic protein or therapeutic RNA effective in treating the disorder or defect.

In some embodiments, the protein, RNA, or DNA is delivered to the subject via intravenous administration or systemic administration. In some embodiments, the protein, RNA, or DNA is delivered in trans. In some embodiments, the protein, RNA, or DNA is delivered to the subject via a nanoparticle. In some embodiments, the RNA is delivered to the subject via a viral vector. In some embodiments, the RNA is delivered to the subject via any carriers suitable for delivering nucleic acid materials. In some embodiments, the protein is a purified protein.

In some embodiments, the protein or RNA is delivered prior to the administration of the AAV vector. The protein or RNA, or an ectopic receptor, can be expressed in the target environment transiently. In some embodiments, the AAV vector can be administered to the subjects 12 hours, 1 day, 2 days, 3 days, 4 days, 5 days, 6 days, 7 days, 8 days, 9 days, 10 days, inclusive of all ranges and subranges therebetween, after the protein or RNA is delivered to the target environment. In some embodiments, the AAV vector can then specifically interact with the ectopic receptor during the timeframe of expression of the delivered ectopic receptor. "Transiently," "transient expression," or "transient gene expression" as described herein refers to the temporary expression of proteins or genes that are expressed for a short time after a protein or a nucleic acid (e.g., plasmid DNA encoding an expression cassette), has been introduced into the target environment.

In some embodiments, the protein or RNA can be delivered to the target environment simultaneously with the AAV vector. In some embodiments, the protein or RNA can be delivered to the target environment with the AAV vector in any order or timeframe that is suitable for treating a disorder or defect in the subject as described herein. For example, the AAV vector can be administered a few minutes after the delivery of the protein or RNA.

Any nucleic acid may be delivered to a target environment of a subject according to methods described herein. In some embodiments, a nucleic acid to be delivered to a target environment of a subject comprises one or more sequences that would be of some use of benefit to the subject. In some embodiments, the nucleic acid is delivered to dorsal root ganglia, visceral organs, astrocytes, neurons, or a combination thereof of the subject.

In a non-limiting example, the nucleic acid or nucleic acid molecule to be delivered can comprise one or more of (a) a nucleic acid sequence encoding a trophic factor, a growth factor, or a soluble protein; (b) a cDNA that restores protein function to humans or animals harboring a genetic mutation (s) in that gene; (c) a cDNA that encodes a protein that can be used to control or alter the activity or state of a cell; (d) a cDNA that encodes a protein or a nucleic acid used for assessing the state of a cell; (e) a cDNA and/or associated guide RNA for performing genomic engineering; (f) a sequence for genome editing via homologous recombination; (g) a DNA sequence encoding a therapeutic RNA; (h) a shRNA or an artificial miRNA delivery system; and (i) a DNA sequence that influences the splicing of an endogenous gene.

Any subject in need may be administered a composition comprising an AAV according to methods described herein. In some embodiments, a subject in need or a subject having a disorder or defect is a subject suffering from or at a risk to develop one or more diseases. In some embodiments, the subject in need is a subject suffering from or at a risk to develop one or more of chronic pain, cardiac failure, cardiac arrhythmias, Friedreich's ataxia, Huntington's disease (HD), Alzheimer's disease (AD), Parkinson's disease (PD), Amyotrophic lateral sclerosis (ALS), spinal muscular atrophy types I and II (SMA I and II), Friedreich's Ataxia (FA), Spinocerebellar ataxia, lysosomal storage disorders that involve cells within the CNS.

Any suitable method may be used for administering a composition comprising an AAV described herein. In some embodiments, the composition comprising the AAV is administered to the subject via intravenous administration. In some embodiments, the composition comprising the AAV is administered to the subject via or systemic administration.

Pharmaceutical Compositions

Aspects of the present disclosure provide, in some embodiments, a pharmaceutical composition comprising an AAV vector as described herein and a pharmaceutically acceptable carrier. Suitable carriers may be readily selected by one of skill in the art in view of the indication for which the AAV vector is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present disclosure. Pharmaceutical compositions comprising AAV vectors are described further in U.S. Pat. No. 9,585,971 and US 2017/0166926, which are incorporated by reference herein in their entireties.

In some embodiments, the pharmaceutical composition comprising an AAV vector comprises other pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

Methods described herein comprise administering AAV vector in sufficient amounts to transfect the cells of a desired tissue (e.g., heart, brain) and to provide sufficient levels of gene transfer and expression without undue adverse effects. Examples of pharmaceutically acceptable routes of administration include, but are not limited to, direct delivery to the selected organ, oral, inhalation, intraocular, intravenous, intramuscular, intrathecal, intracranial, subcutaneous, intradermal, intratumoral, and other parental routes of administration. Routes of administration may be combined, if desired.

The dose of AAV required to achieve a particular "therapeutic effect," e.g., the units of dose in genome copies/per kilogram of body weight (GC/kg), will vary based on several factors including, but not limited to: the route of AAV administration, the level of gene or RNA expression required to achieve a therapeutic effect, the specific disease or disorder being treated, and the stability of the gene or RNA product. One of skill in the art can readily determine a AAV dose range to treat a patient having a particular disease or disorder based on the aforementioned factors, as well as other factors.

An effective amount of AAV vector is an amount sufficient to infect an animal or target a desired tissue. The effective amount will depend primarily on factors such as the species, age, weight, health of the subject, and the tissue to be targeted, and may thus vary among animal and tissue. For example, an effective amount of AAV is generally in the range of from about 1 ml to about 100 ml of solution containing from about 109 to 1016 genome copies. In some cases, a dosage between about 1011 to 1013 AAV genome copies is appropriate. In some embodiments, an effective amount is produced by multiple doses of AAV.

In some embodiments, a dose of AAV is administered to a subject no more than once per calendar day (e.g., a 24-hour period). In some embodiments, a dose of AAV is administered to a subject no more than once per 2, 3, 4, 5, 6, or 7 calendar days. In some embodiments, a dose of AAV is administered to a subject no more than once per calendar week (e.g., 7 calendar days). In some embodiments, a dose of AAV is administered to a subject no more than bi-weekly (e.g., once in a two calendar week period). In some embodiments, a dose of AAV is administered to a subject no more than once per calendar month (e.g., once in 30 calendar days). In some embodiments, a dose of AAV is administered to a subject no more than once per six calendar months. In some embodiments, a dose of AAV is administered to a subject no more than once per calendar year (e.g., 365 days or 366 days in a leap year). In some embodiments, a dose of rAAV is administered to a subject no more than once per two calendar years (e.g., 730 days or 731 days in a leap year). In some embodiments, a dose of AAV is administered to a subject no more than once per three calendar years (e.g., 1095 days or 1096 days in a leap year).

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active compound or more, although the percentage of the active ingredient(s) may, of course, be varied and may conveniently be between about 1 or 2% and about 70% or 80% or more of the weight or volume of the total formulation. Naturally, the amount of active compound in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The AAV vector compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. The phrase "pharmaceutically-acceptable" refers to molecular entities and compositions that do not produce an allergic or similar untoward reaction when administered to a host.

Delivery vehicles such as liposomes, nanocapsules, microparticles, microspheres, lipid particles, vesicles, and the like, may be used for the introduction of the compositions of the present disclosure into suitable host cells. In particular, the AAV vector delivered transgenes may be formulated for delivery either encapsulated in a lipid particle, a liposome, a vesicle, a nanosphere, or a nanoparticle or the like.

Such formulations may be preferred for the introduction of pharmaceutically acceptable formulations of the nucleic acids or the AAV constructs disclosed herein. The formation and use of liposomes is generally known to those of skill in the art. Recently, liposomes were developed with improved serum stability and circulation half-times (U.S. Pat. No. 5,741,516). Further, various methods of liposome and liposome like preparations as potential drug carriers have been described (U.S. Pat. Nos. 5,567,434; 5,552,157; 5,565,213; 5,738,868 and 5,795,587).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Alternatively, nanocapsule formulations of the AAV vector may be used. Nanocapsules can generally entrap substances in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use.

Some aspects of the technology described herein may be understood further based on the non-limiting illustrative embodiments described in the below Examples section. Any limitations of the embodiments described in the below Examples section are limitations only of the embodiments described in the below Examples section, and are not limitations of any other embodiments described herein.

EXAMPLES

In order that the invention described in the present disclosure may be more fully understood, the following examples are set forth. The examples described in this application are offered to illustrate the systems and methods provided in the present disclosure and are not to be construed in any way as limiting their scope.

Example 1: Mapping Production Fitness Distribution with Synthetic Libraries

Conventional combinatorial site saturation libraries built using NNN or NNK codons (K denotes a glycine [G] or threonine [T]) randomly sample the nucleotide sequence space. This method is inherently biased towards amino acids that are encoded by a greater number of codons. In addition, the theoretical diversity of these libraries often exceed the practical diversity that can be generated or quantitatively and reproducibly screened. These biases and lack of reproducibility make it challenging to generate data suitable for training machine learning (ML) models to accurately map sequence-to-fitness and sequence-to-function maps.

Figures 6A, 6B, 6C, 6D:
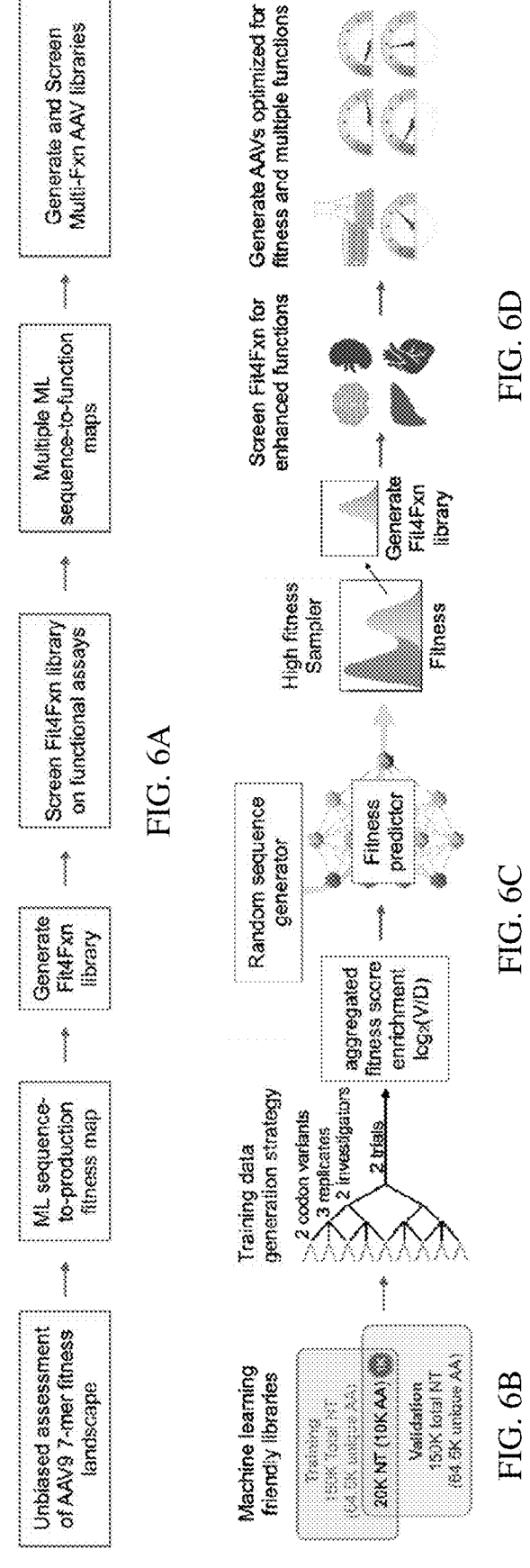
FIGS. 6A-6D depict design of the training libraries, replication strategy, and machine learning framework.
Figure 7A:
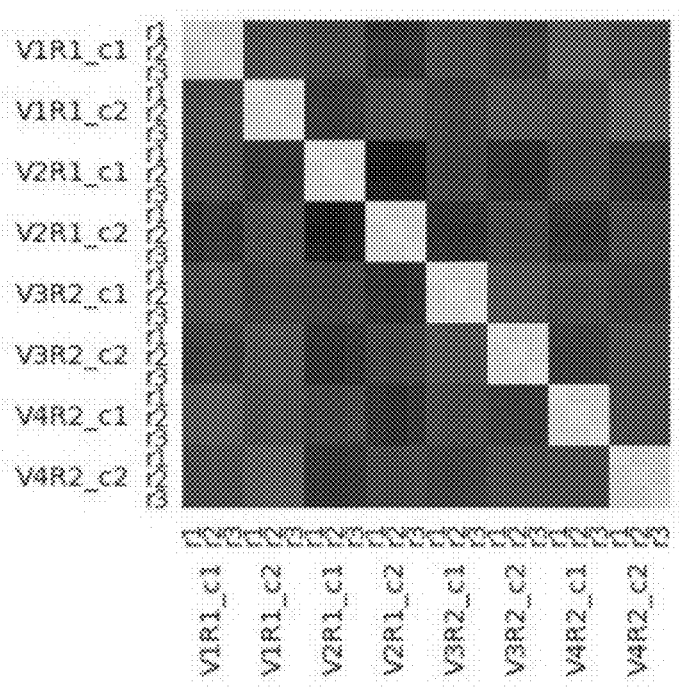
FIGS. 7A-7E provide graphs showing that fitness scores replication quality improves upon hierarchical aggregation of replicates.
Figure 7B:
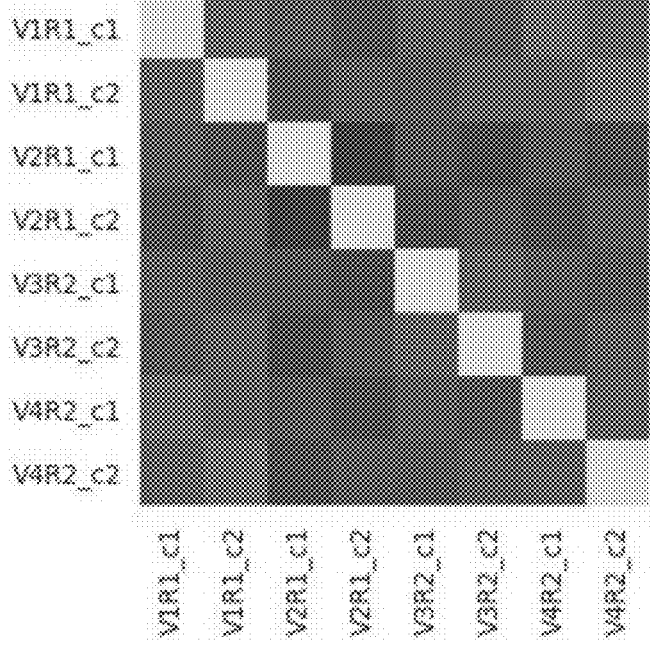
Figure 7C:
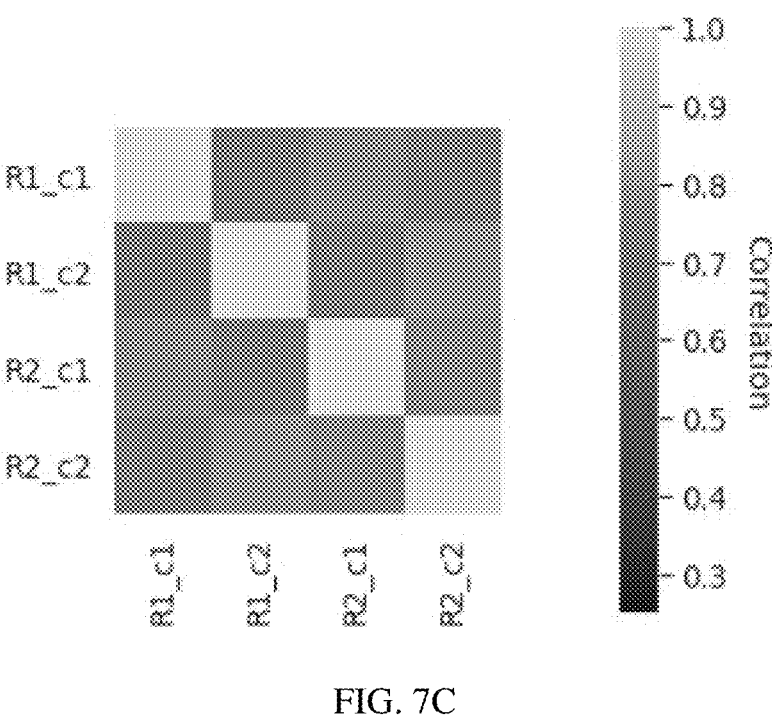
Figure 7D:
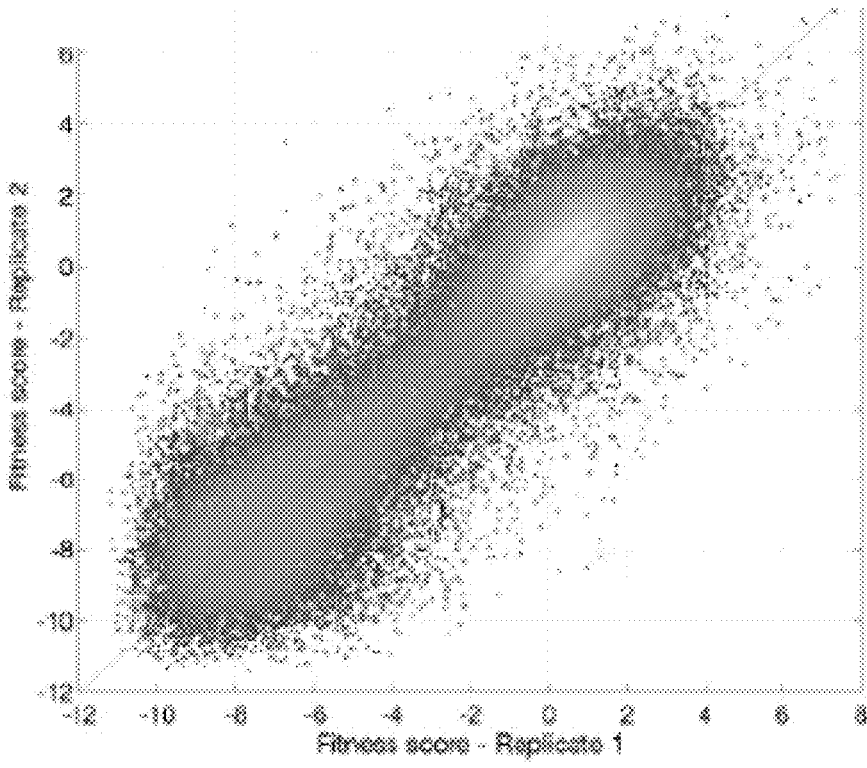
Figure 7E:
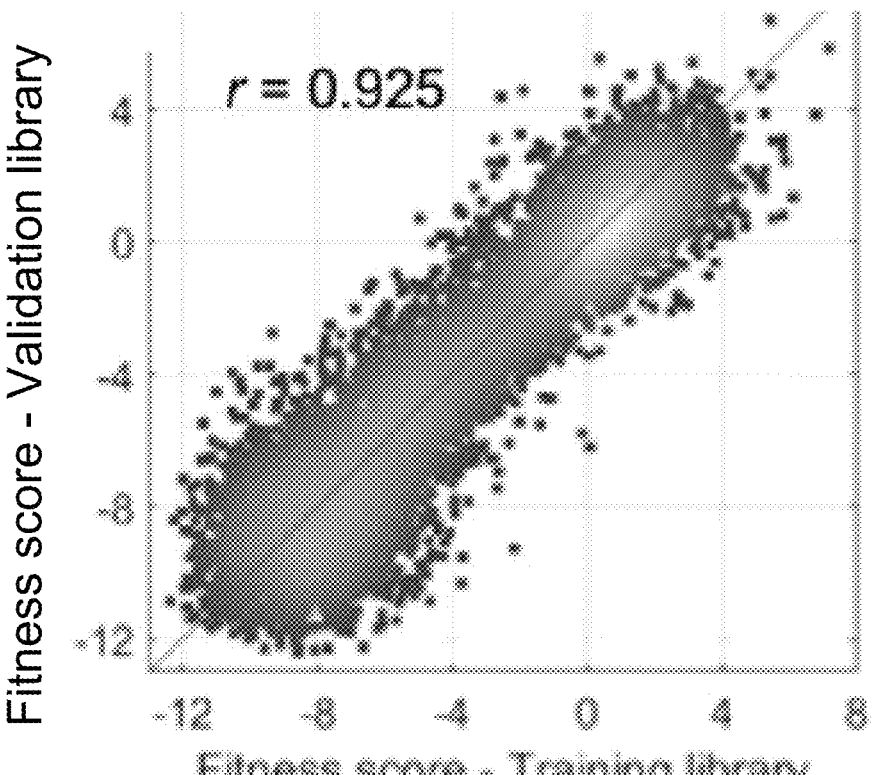

To derive highly accurate and generalizable ML models (FIG. 6A-6D), synthetic libraries of AAV9 capsids modified through the insertion of 7 amino acids (7-mer) between residues 588-589 in VP1 were created, which sampled the vast 7-mer production fit landscape with as little bias as possible (FIG. 6A). These libraries were used to train and validate a ML model to predict the 7-mer modified AAV capsid production fitness. Specifically, two libraries with defined variants were synthesized: a "Training" library for training and validating the ML model, and a "Validation" library for assessing the reproducibility of the fitness scores and the model's generalizability, i.e., how well the model predicts the fitness of variants in other libraries. Each library contains 150K nucleotide sequences, coding for 64.5K amino acid variants that are unique to each library and 20K nucleotide sequences, coding for 10K amino acid variants common to both libraries. The design of the libraries (FIG.

6B) incorporated these considerations: (1) They uniformly sample the amino acid sequence space by sampling each amino acid with an equal probability at each position. (2) They assess whether codon usage impacts production fitness by representing each variant with two nucleotide sequences chosen to maximize the difference in codons between each pair. (3) The training and validation libraries share a control set of 10K amino acid variants with each other to facilitate assessments of reproducibility across libraries with different sets of defined variants. (4) They contain 1K amino acid variants with nonsense mutations as a quality control measure to detect excessive cross packaging.

Figure 9:
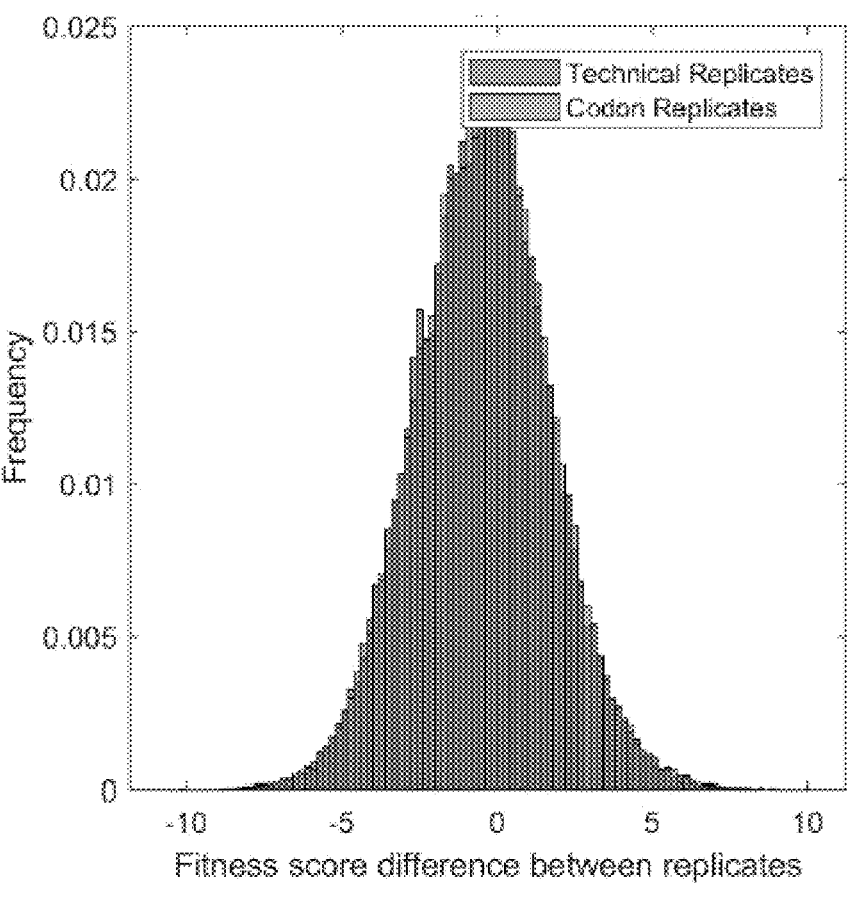
FIG. 9. provides a graph showing that the distribution of the difference in fitness scores measured between codon replicates and between technical replicates were similar (Kullback-Leibler divergence=0.006±0.007). Codon usage was found to minimally affect 7-mer insertion capsid fitness FIGS. 10A-10E provide schematics and graphs showing that the fitness predictor enables the generation of Fit4Fxn, libraries that exclusively and evenly sample the high fitness space.

High-quality data for training and validating the ML predictors were generated by producing each of the two AAV libraries in triplicate, in two separate runs, by two different researchers (FIG. 6C). The production fitness of each variant was scored by the enrichment of its abundance in the virus sample after purification and nuclease treatment relative to its abundance in the initial plasmid pool (production fitness score=enrichment, log 2 virus reads per million (RPM)/plasmid RPM). The fitness scores were consistent and reproducible, and the quality of replication improved as replicates were aggregated (FIG. 7A-7E). Codon usage did not appear to impact production fitness, as there was a high degree of correlation between the fitness scores of codon replicates (r=0.891, FIG. 8A), and the distribution of measured differences did not exceed those observed between technical replicates (Kullback-Liebler divergence=0.006±0.007, FIG. 9). Of the 13,217 codon replicates that were unmatched (20.5% of the total 64,500 unique AA variants), where only one of the two codon sequences were detected, nearly all (>99%) had fitness scores on the low end of the bimodal distribution (FIG. 8A). These data indicate that production fitness can be mapped at the amino acid level rather than the nucleotide level, reducing the interrogated sequence space by more than three orders of magnitude, from 617 (317 for NNK) nucleotide sequences to 207 amino acid variants. Therefore, all subsequent training and analysis was performed on the fitness scores aggregated from the two codon replicates for each amino acid variant.

The production fitness landscape of the training library can be modeled by a mixture of two Gaussian distributions: a "low fit" distribution and a "high fit" distribution (FIG. 8B). The variants in the high fit distribution exhibit distinguishing amino acid sequence characteristics, such as a general enrichment of negatively charged residues (D, E) and depletion of cysteine (C) and tryptophan (W) (FIG. 8C). Sampling evenly across the amino acid space within the high fit distribution reduces amino acid biases that are typically observed in the top 150K most abundant sequences in conventional NNK libraries (FIG. 8C). This library design effectively reduces bias against amino acids such as tryptophan (W), a potentially important residue for driving protein-protein interactions (Bogan and Thorn 1998; Traxlmayr et al. 2016). Importantly, the production fitness scores for the 10K amino acid variants present in both libraries were consistent across libraries, indicating that they are not greatly impacted by the other member variants in each library (FIG. 8D). This supports the idea that generalizable ML models can be developed to predict the production fitness scores of variants independent of the library composition.

Example 2: Building Accurate and Reproducible Production Fitness Predictors

Prior studies have applied classification models to predict AAV capsid fitness (Bryant et al. 2021; Marques et al. 2021).

In the present disclosure, a regression model was used because of the large spread of relative fitness scores (+5-fold) within the high fit and low fit distributions (FIG. 8B). A regression model can capture this intra-distribution variance and inform decisions about trade-offs between variant production fitness and, as discussed below, variant function. A ML framework was built for 7-mer sequence-to-function mapping composed of a regression model with learning control strategies to avoid model overfitting and hence improve model prediction generalization. The ML model consists of a two-layer long short-term memory (LSTM) recurrent neural network (RNN) with input (variants) one hot-encoded and the target/output as the relative production fitness score. An LSTM architecture was chosen for its ability to more efficiently learn intra-sequence relationships (Hochreiter and Schmidhuber 1997), which here correspond to epistatic interactions and dependencies among the residues of the 7-mer sequences.

Figure 8F:
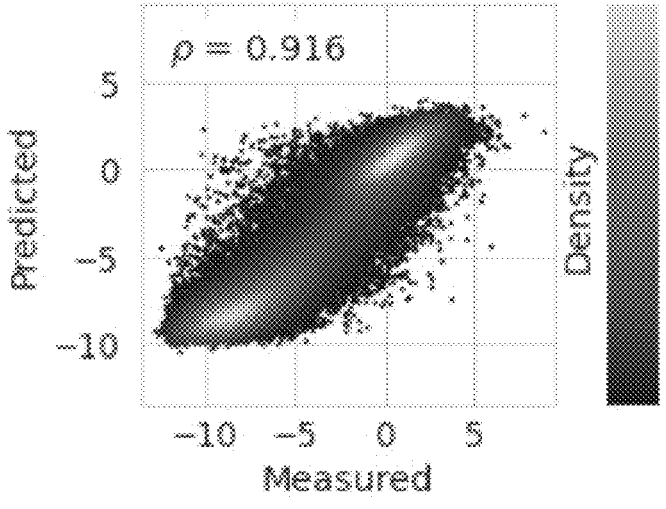

To develop a fitness predictor, an ML framework was trained using the training library, which was further split into a training subset of 24K amino acid variants and a testing subset of 25.6K variants; the 10K variants that overlap between the training library and the validation library were entirely excluded from this process. The fitness predictor was trained using the training subset from the training library, and achieved high accuracy on the testing subset (r=0.919, FIG. 8E), as well as on the independent validation library (r=0.916, FIG. 8F). As anticipated, nearly all of the variants that were not detected (i.e., not measured) in the virus library, despite being detected in the DNA library used for virus production, were projected by the model into the low-fitness distribution (FIG. 8E); this applied to undetected virus variants in either the training or testing subset of the training library. These results demonstrate that the ML framework is not biased by the training data, and is generalizable across libraries and to unseen variants.

Figure 8G:
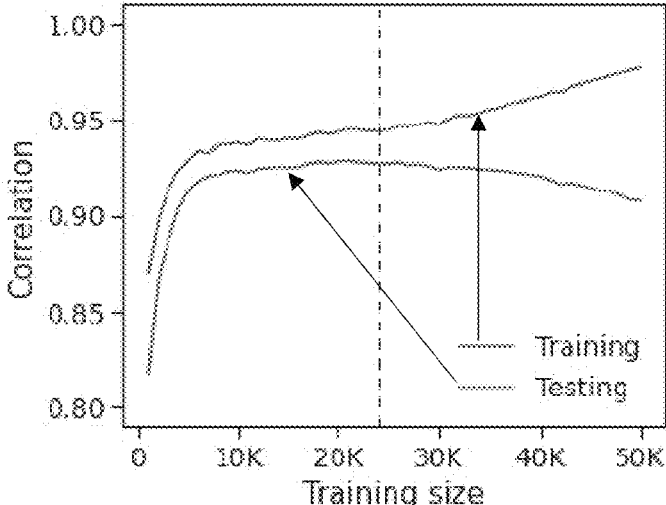
Figure 8H:
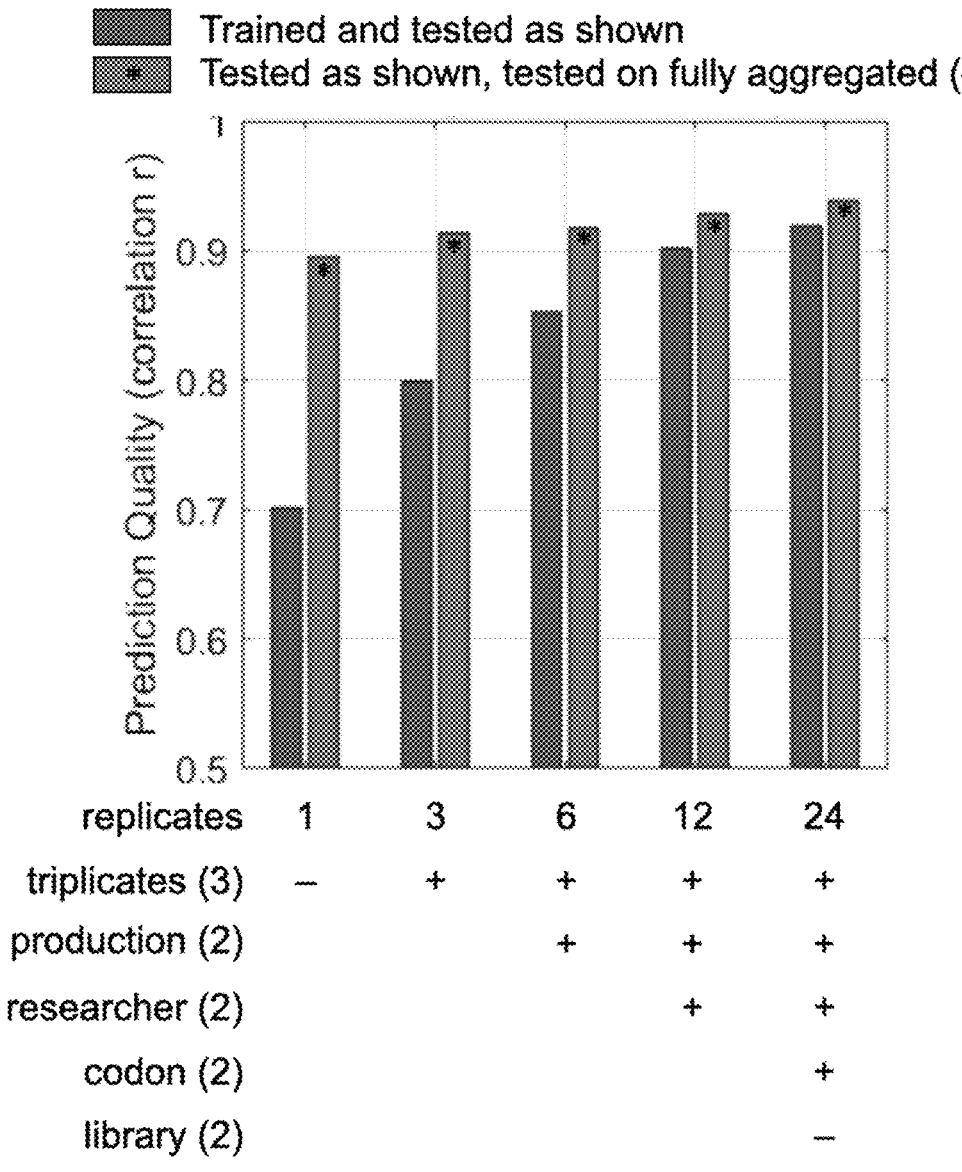

It was observed that the production fitness predictor did not require large amounts of training data to obtain high accuracy: Reducing the training from 24K to 5K variants yielded only a slightly lower performance (r=0.91, FIG. 8G). To further explore the data requirements, independent instances of the framework were trained on data sets constructed from a different number of measurements (1, 3, 6, or 12 replicates; 24 replicates had been used to train the original fitness predictor). The resulting models were tested on a disjoint subset with the same respective number of replicates OR against the fully aggregated data of the 10K amino acid variant control set shared between the training and validation libraries (48 replicates in total per variant), which was used as an approximation of the true fitness scores. Surprisingly, even when learning from a single measurement per variant, the model achieved accuracy very close to the model trained on the more extensively aggregated data (FIG. 8H). This suggests that the model learns the signal from lower quality (non-aggregated) data, and that the apparent accuracy is likely capped by the measured accuracy (replication quality). The true accuracy can therefore be much higher when validated on high replication quality data; a similar observation was reported for deep learning-based classification (Rolnick et al. 2017).

Example 3: Fit4Fxn Libraries Evenly Sample the Production Fit Landscape

Figure 11A:
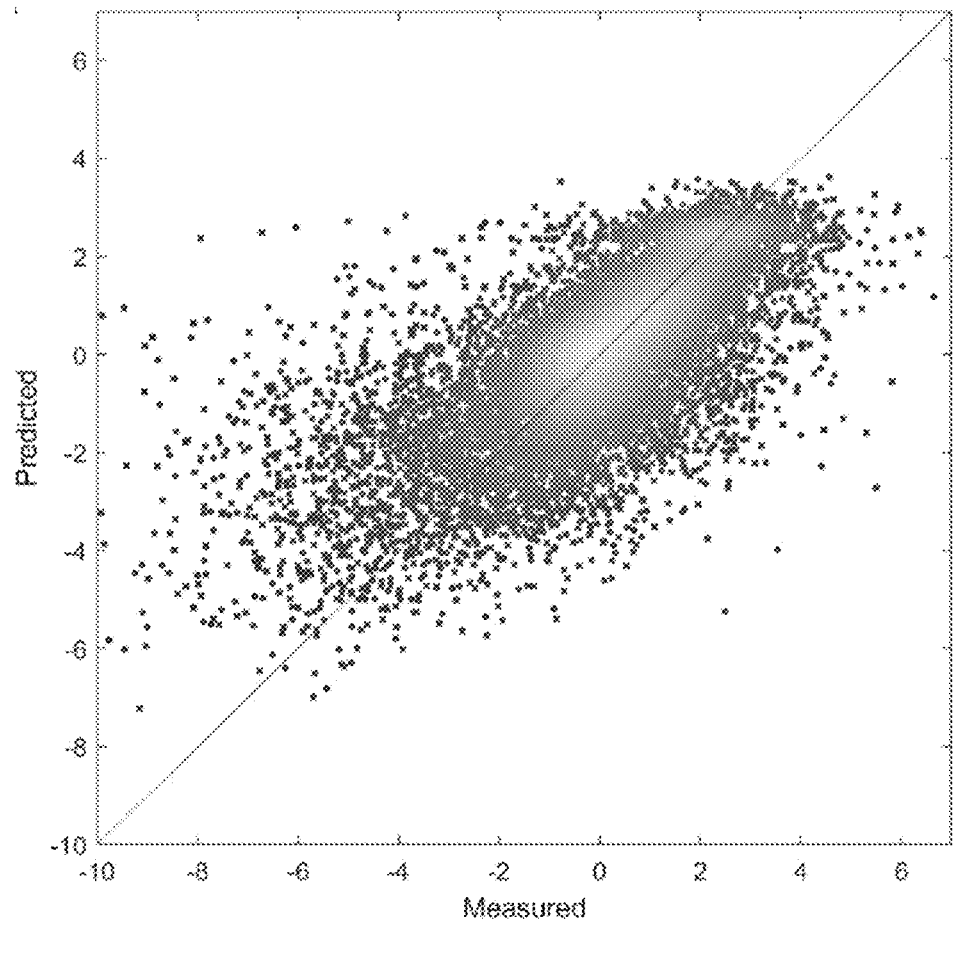
FIGS. 11A-11B provide graphs showing pre-synthesis validation of Fit4Fxn library sampling scheme quality.
Figure 11B:
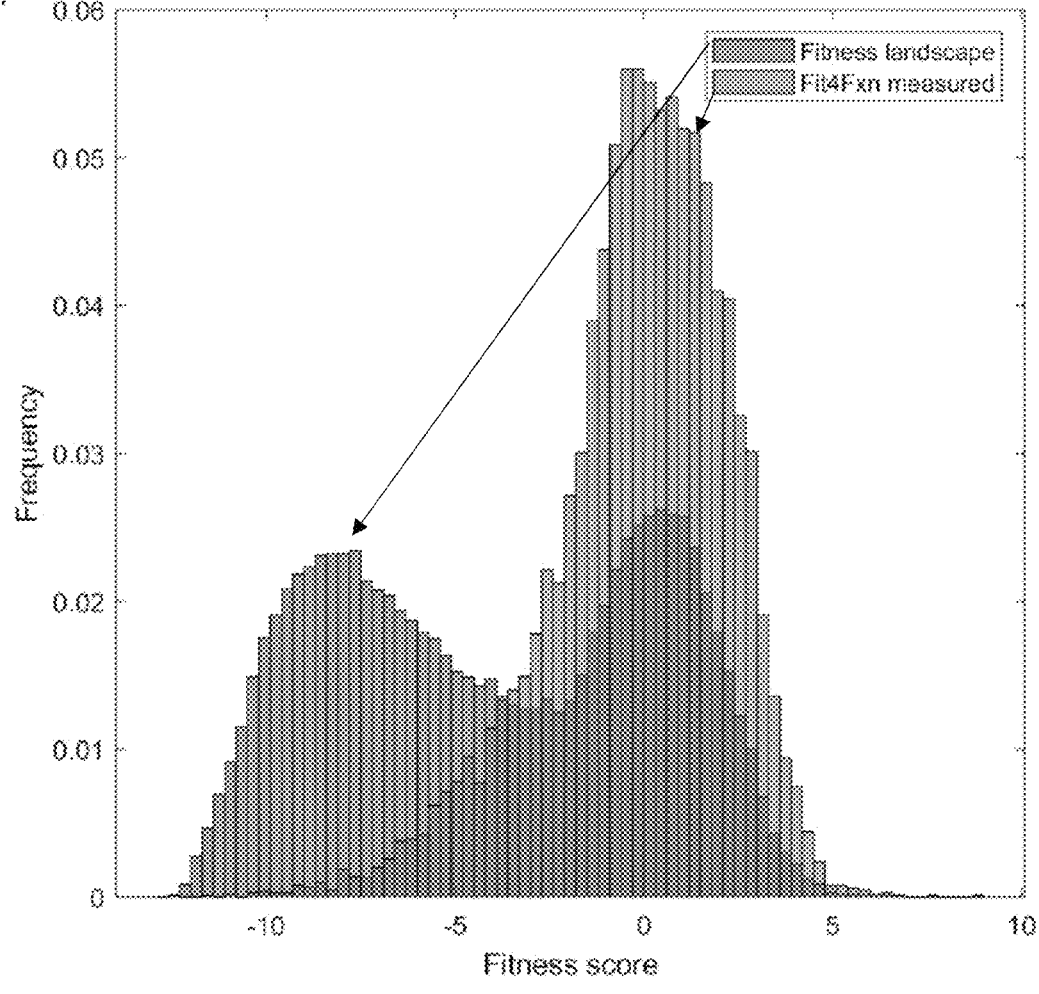
Figures 12A, 12B, 12C:
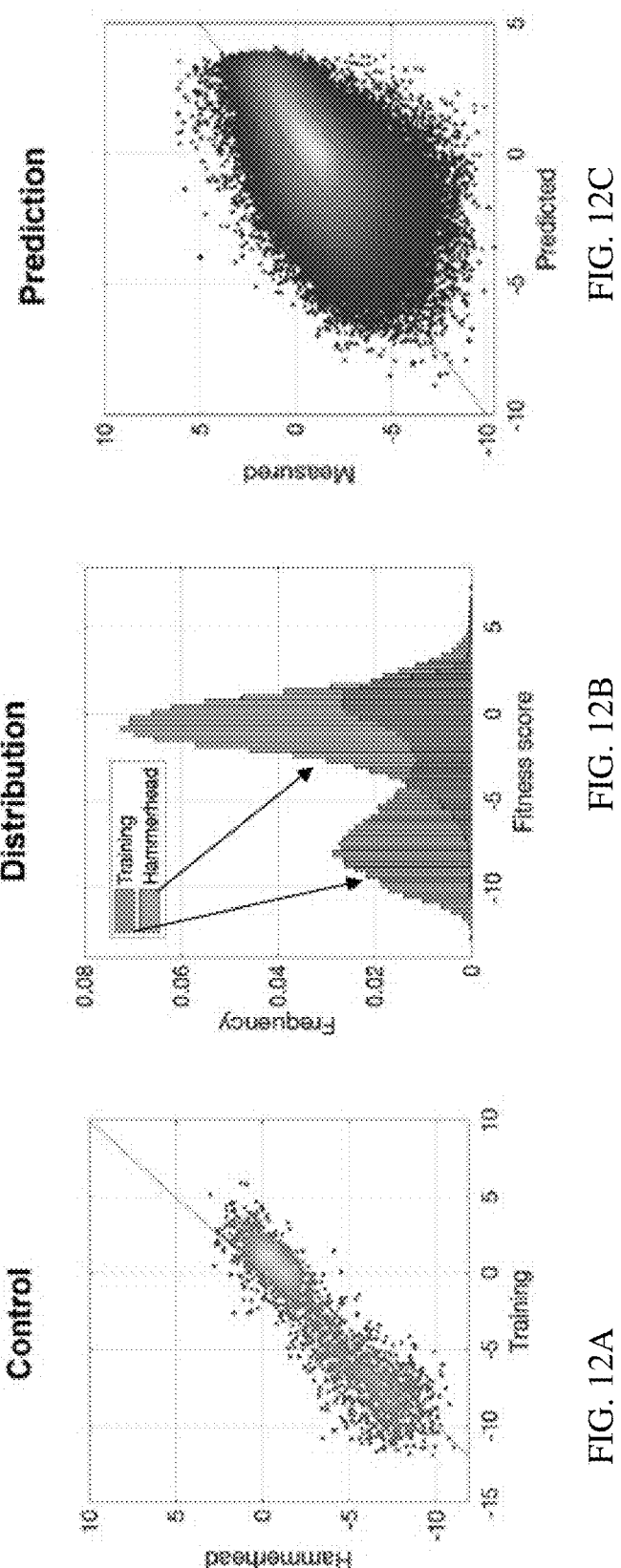
FIGS. 12A-12F provide graphs showing fitness score calibration across libraries with different fitness landscapes. Calibration is intended only to show expectation matching but does not affect subsequent usage of the library; i.e. calibration is intended to make the two libraries comparable. Hammerhead fitness=1.18*Training fitness+0.765.
Figures 12D, 12E, 12F:
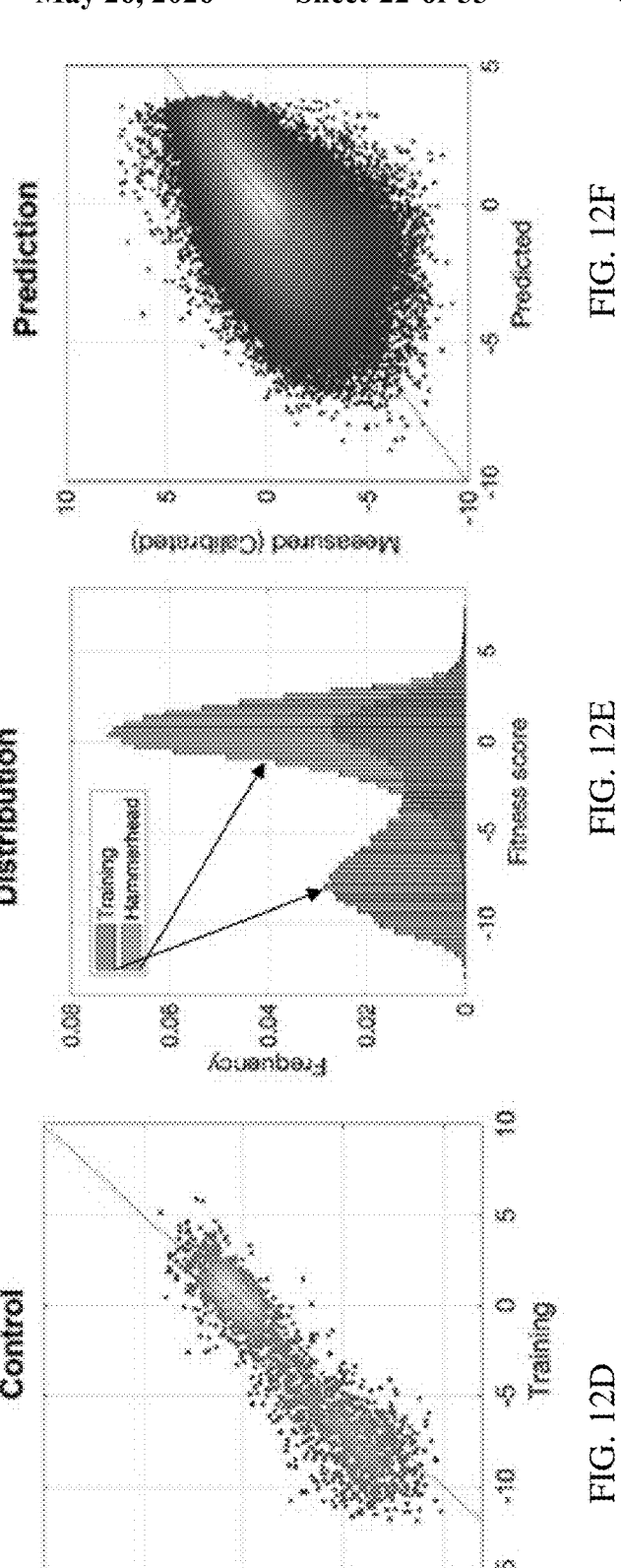

Using the production fitness predictor, a 240K amino acid variant Fit4Fxn library was designed and synthesized (termed "Hammerhead") that evenly samples the production fit landscape (FIG. 6C and FIG. 10A). To populate this library, 24M variants were randomly generated, the fitness of each generated variant was predicted using the production fitness model, and 240K variants were sampled from the high-fit Gaussian component. The production fitness scores of the resulting Fit4Fxn library were estimated and determined to closely match the high-fit distribution by simulating the sampling process on the measurements of the validation library (r=0.69, FIG. 10B and FIG. 11A). In addition to the 240K high-fit variants, 3K variants uniformly sampling from the control set shared by the training and validation libraries for calibrating the measured relative fitness scores and 1K stop-codon containing variants as cross packaging controls were added.

The measured production fitness distribution of the synthesized Fit4Fxn library was characterized. Remarkably, after calibration, the measured fitness scores for the variants mapped to a single, near Gaussian distribution that closely follows the high fit distribution component of the fitness landscape (FIG. 10B and FIG. 12A-12F). The calibrated measured fitness scores showed a high degree of correlation with the predicted fitness scores (r=0.66, FIG. 10C).

To assess the diversity of the library, the pairwise Hamming distance was computed between all sequences and 67% of the sequences were found to have a distance of 7 (all positions). In comparison, 57.8% of the sequences in the top 240K most abundant sequences detected in a random (NNK) 7-mer peptide-modified library differ at all seven positions (Hamming distance=7; FIG. 10D). Furthermore, the distribution of amino acids in the Hammerhead library is similar to that of the high-fit distribution (from the training library) and deviates less from an even amino acid representation than the top 240K variants found in an NNK library (FIG. 10E).

Example 4: Fit4Fxn Libraries Improve Data Reproducibility and Enable Multi-Function Learning To identify variants that possess multiple traits of interest using conventional NNN/NNK libraries, two strategies are used: sequential optimization or parallel screening. In the sequential optimization strategy, a library is screened to identify variants harboring the function of greatest priority; then, lead candidates are synthesized, with or without additional mutagenesis, and subjected to additional screening for secondary functions of interest. The parallel approach, where a library is simultaneously screened across multiple assays, can be confounded by sparse sampling as well as by false positives. Unlike an NNK library, the Fit4Fxn library has the potential to overcome the sparse sampling and false positive limitations because its membership is defined and it samples uniformly from the high production fit space. With a quantifiable, defined membership library, negatives (sequences not recovered after screening) can be confidently labeled as negative values. In this manner, Fit4Fxn libraries enable the generation of high quality negative and high quality positive data for ML training. In comparison, the negative data produced using NNK libraries are typically not of sufficient quality for ML.

Figure 13A:
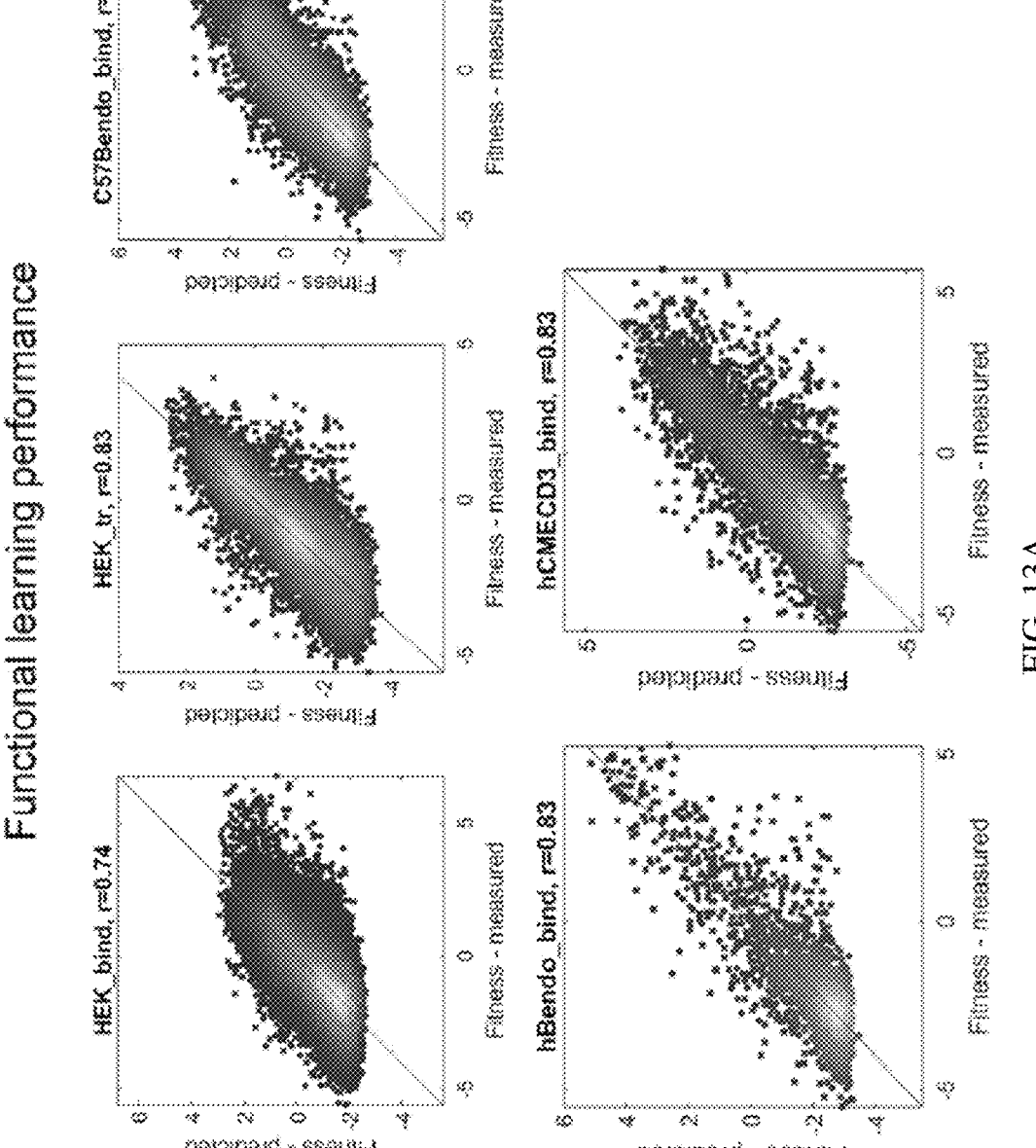
FIGS. 13A-13C provide graphs showing that Fit4Fxn enables accurate functional screening and prediction.
Figure 13B:
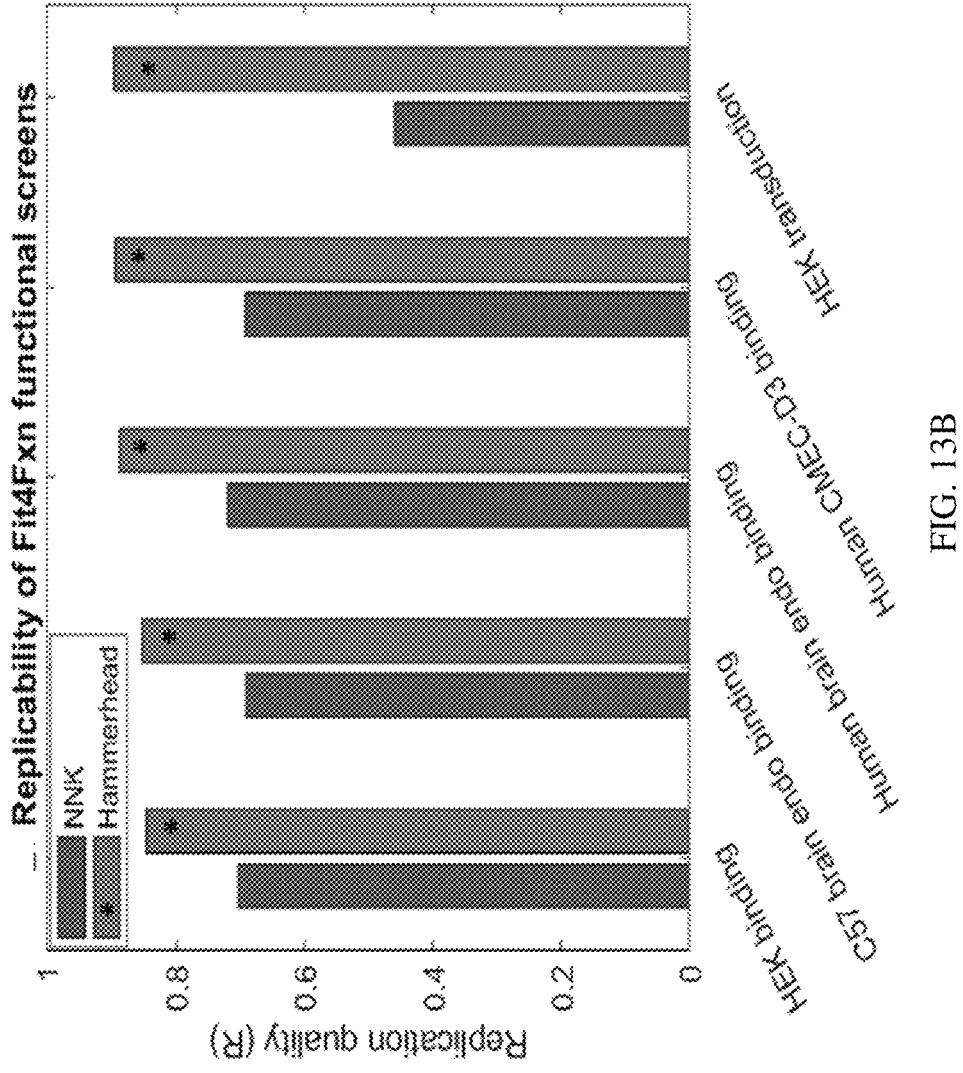

Given the defined membership, reduced fitness bias, and reduced amino acid bias, it was predicted that the Hammerhead library would enable the generation of more reproducible functional screening data. To test this, the Hammerhead library and an NNK library were screened across five functional assays: HEK293 cell binding, primary mouse brain microvascular endothelial cell (BMVEC) binding, primary human BMVEC binding, human brain endothelial cell line (hCMEC/D3) binding, and HEK293 transduction (FIG. 13A). Binding and transduction screens were measured by reading out the capsid variant sequence at the DNA and mRNA level, respectively (see Methods). For all assays, the Hammerhead library, as compared to the NNK library, consistently yielded higher replication quality data, measured by the average replication (correlation r) across pairs among the three replicates (FIG. 13B).

Figure 13C:
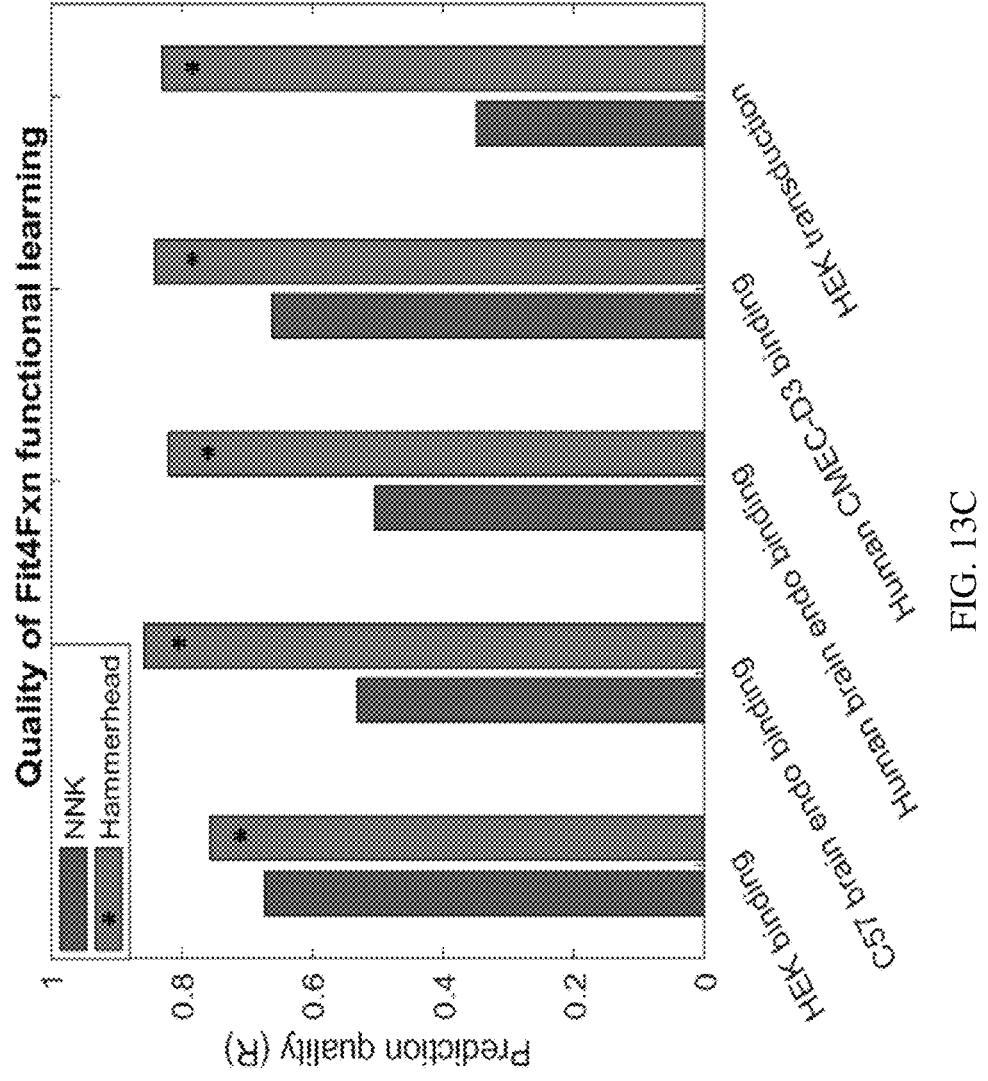

To predict variants that possess multiple traits of interest, sequence-to-function mappings were learned for each of the in vitro and in vivo functions screened with the Hammerhead library. To interrogate the unsampled sequence space, another ML stage/step was devised to first learn sequence-to-function mappings for individual functions independently and to then utilize these models to predict variants that simultaneously possess multiple traits of interest. The data obtained from the Hammerhead library screens were split into model building (90K variants) and multifunction test subsets (150K variants). For the 7-mer sequence-to-function mapping, the same ML framework designed for production fitness prediction was used. Because the ML framework generalized well to variants screened in independent libraries during production fitness learning, a single library for the testing and validation of the function prediction models was used. For each of the five functions, the resulting sequence-to-function models achieved high accuracy prediction quality (r=0.74 to 0.84, FIG. 13C). The reduction in accuracy for the functional learning (r=0.74 to 0.84) compared to the production fitness learning (r>0.9) can be attributed to the smaller number of replicates performed for each functional assay compared to production fitness measurements (3 versus 24 replicates, respectively) as demonstrated for learning from low-replicate data on production fitness (FIG. 8E). For comparison, the ML framework was trained on NNK library data from the same five functional assays using the most abundant 240K variants recovered, generating independent ML models for each function. Each model was trained on 50K variants (determined by optimizing the training size for each model independently) and tested on 40% of the detected variant measurements from the corresponding assay. In each case, the ML framework trained on the Hammerhead library outperformed that trained on NNK (FIG. 13C). Thus, the sequence-to-function ML framework has demonstrated generalizability in production fitness prediction.

Figure 14A:
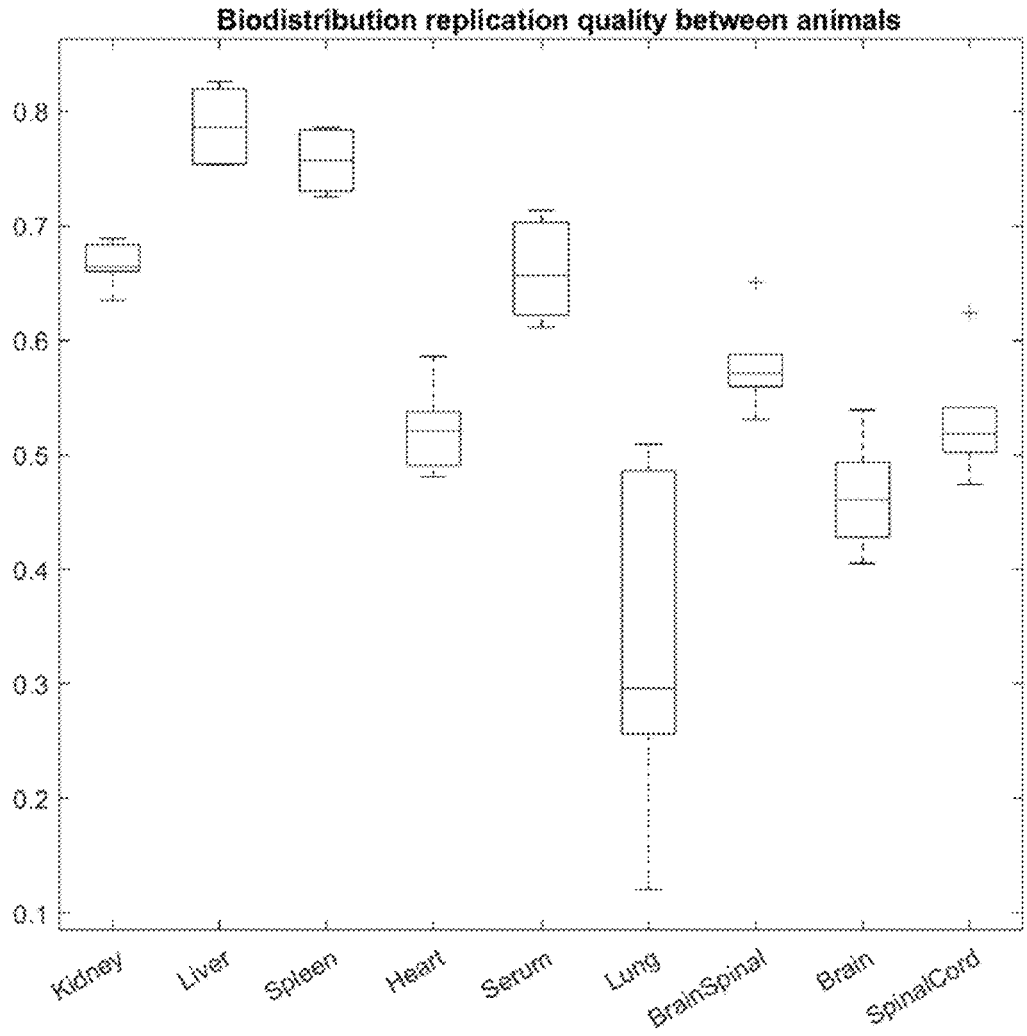
FIGS. 14A-14C provide graphs showing in vivo biodistribution.
Figure 14B:
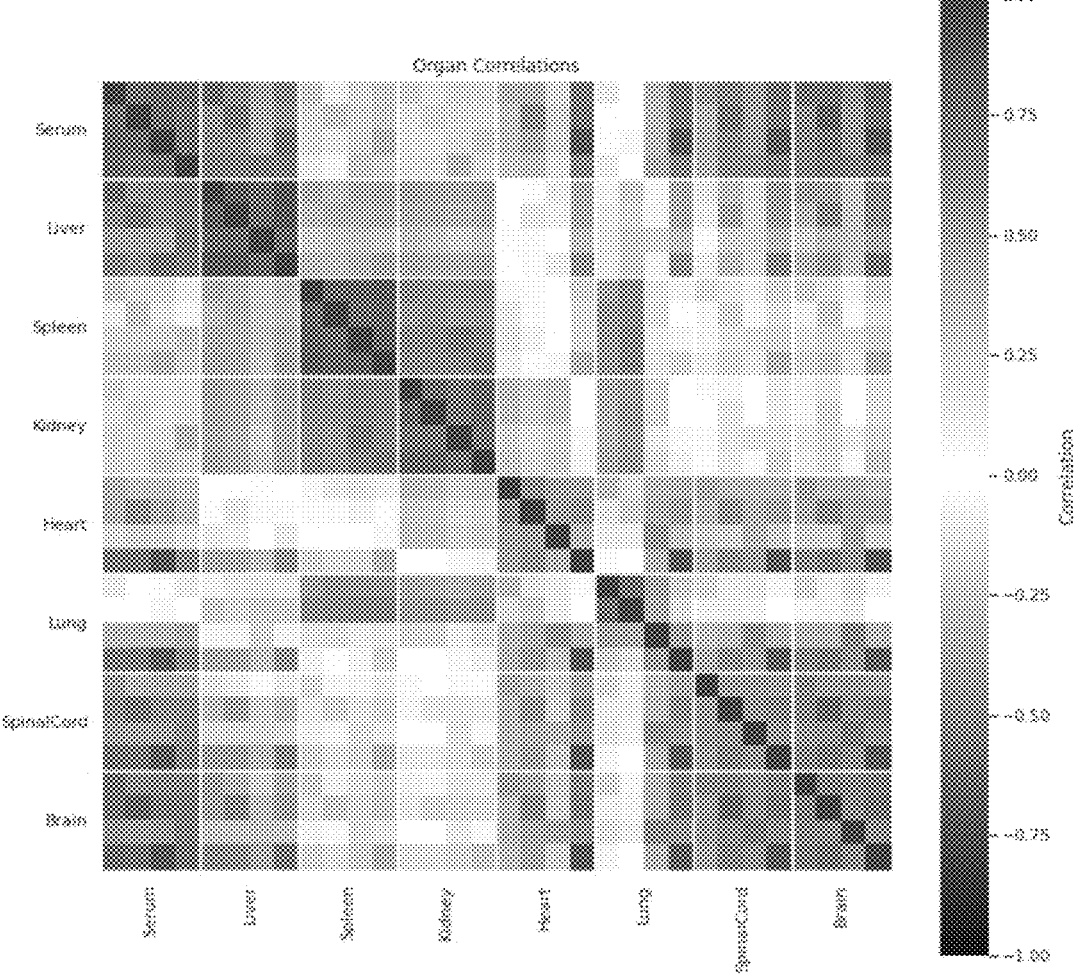
Figure 14C:
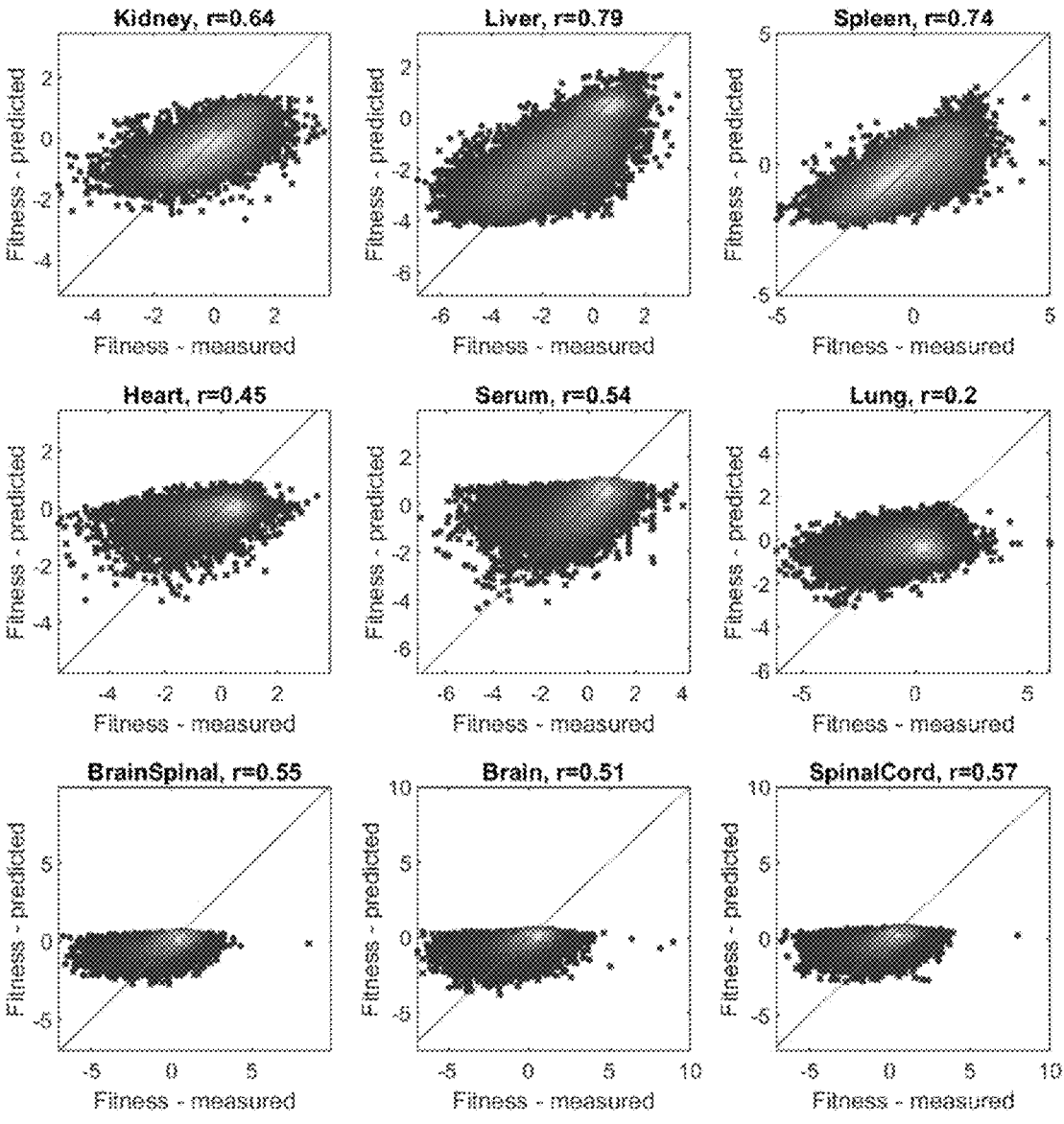
Figures 15A, 15B:
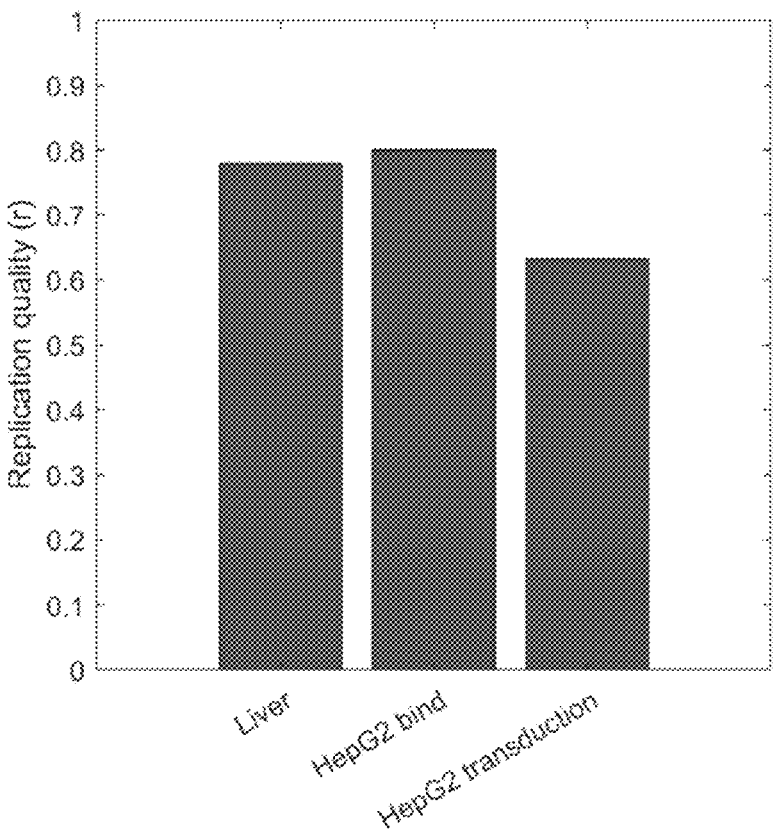
FIGS. 15A-15E provide graphs showing that multi-function learning enables discovery of variants with cross-species tropism enhancements.

Next, the Hammerhead library was used to train the ML framework to predict in vivo biodistribution after systemic administration in adult C57BL/6J mice. The replication quality was excellent in liver, kidney, spleen and serum, good in the brain, spinal cord, and heart, and was lower in the lung (FIG. 14A and FIG. 15B). Independent ML models based on the 7-mer ML framework were trained on optimized numbers of variants for each organ (Methods) to predict the enrichment of variants targeting that organ. The training data measurements were aggregated from three animals; the data from the fourth animal was held out for testing. The model performance was assessed by testing each model on a disjoint test set of variants from the remaining 90K variants after excluding the training examples, 5K training control examples, and the variants not detected for that organ. The test measurements were recovered from an independent animal. The models performed considerably well when trained on assays with higher reproducibility (FIG. 14C), demonstrating the applicability of this approach to in vivo data.

Figure 15C:
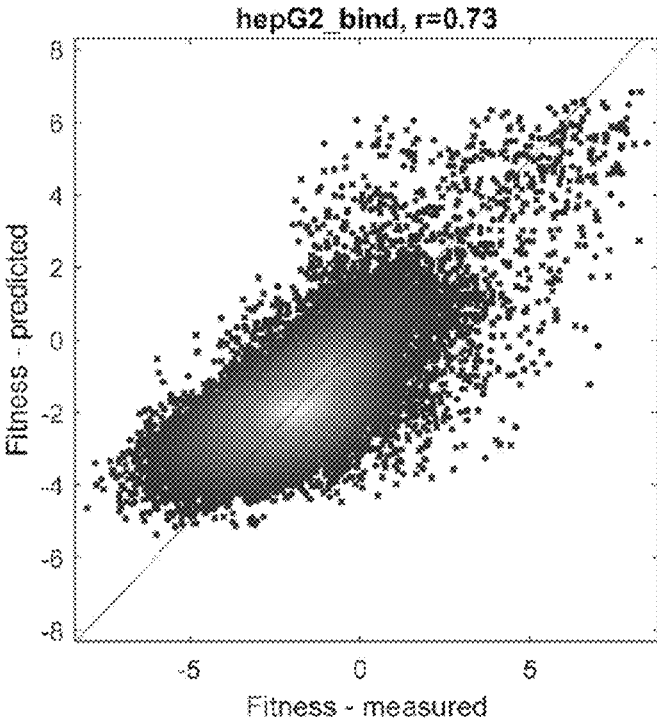
Figure 15D:
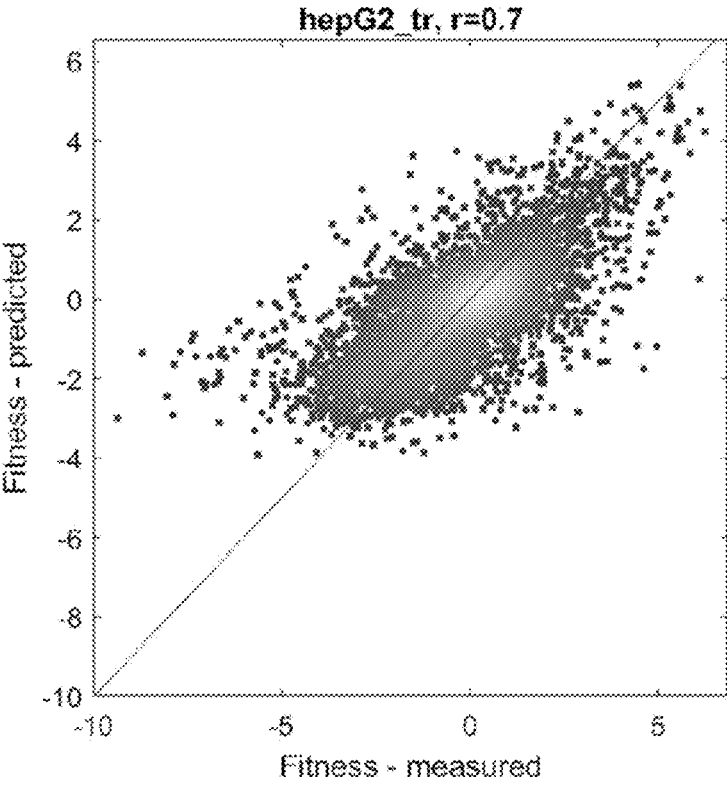
Figure 15E:
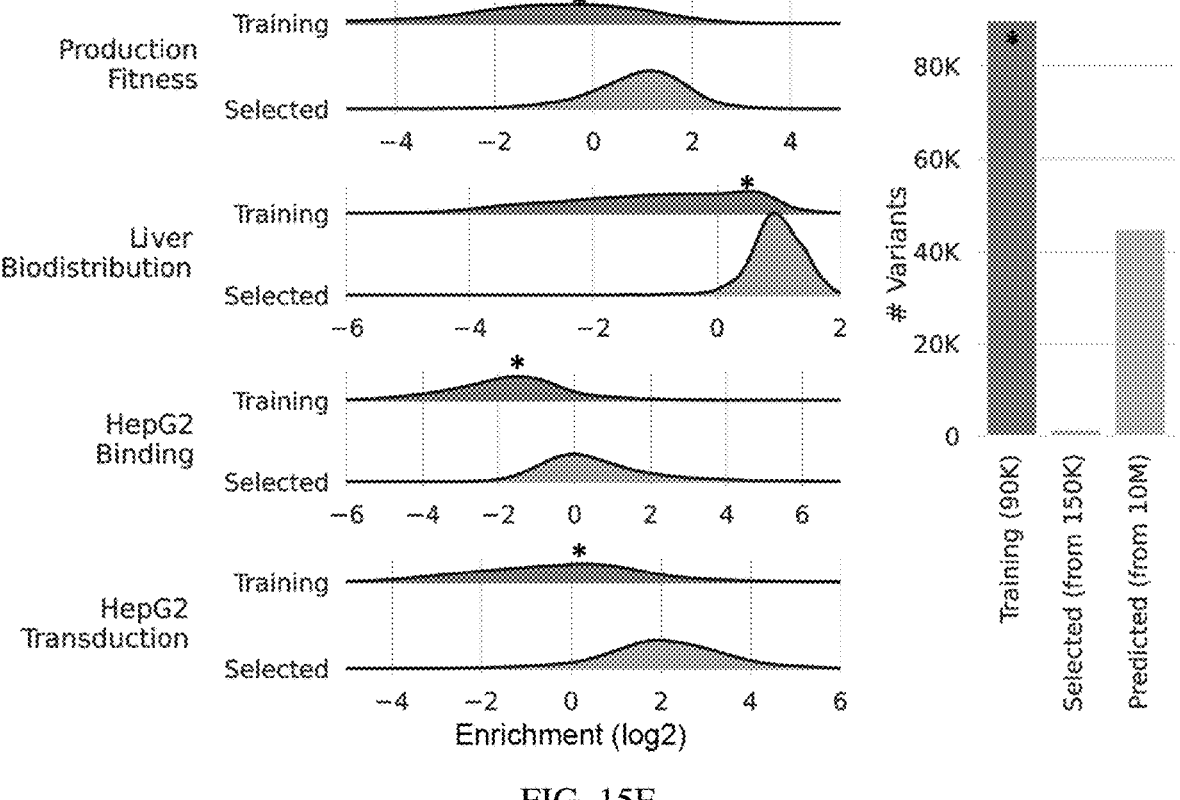

Example 5: The MultiFxn Approach can Predict Rare Variants that are Likely to Possess a Combination of Desired Functional Phenotypes The multiple functional models were leveraged to search the 7-mer sequence space for variants that exhibit enhanced cross-species hepatocyte tropism and high production fitness. Previous efforts to develop capsids with improved human hepatocyte transduction have led to enhancements that are selective for human cells, but not mouse cells (Lisowski et al. 2014; Paulk et al. 2018; Qian et al. 2021). While such vectors have important translational potential, there is a need for improved methods to find AAV capsids that work across species to facilitate more reliable preclinical efficacy and safety testing. To identify capsids with cross-species transduction enhancements, the Hammerhead library was screened for binding and transduction of the human hepatocellular carcinoma cell line (HepG2) and liver-directed biodistribution in mice. These screens generated data that was highly reproducible in each assay (FIG. 15A). The ML functional models were used to predict the enrichment scores of these three functions on the 150K validation subset (FIG. 15B-15D). The intersection subset of variants (N=1,491) that are optimized for the three traits (positive enrichment) as well as for high production fitness were identified (FIG. 15E). FIG. 15E is a graph (right) that shows the number of variants used for training the ML functional models, the number of variants from a 150K library that meets the selection criteria, and the number of sequences predicted to meet the selection criteria in a set of 10M sequences that passed through the fitness predictor followed by scoring for the characteristics identified (left). These results indicate that a large number of untested variants (10M) can be randomly sampled in silico, pass through the fitness predictor and multiple statistical models that map sequences to protein characteristics, and then generate a large number of variants (45K) that are predicted to have multiple desirable functions. The 45K library could then be screened using the same and/or additional assays of interest to identify top performers out of the 45K sequences. The prediction precision was high (0.83) indicating that the MultiFxn approach can predict rare capsid variants that exhibit high production fitness and cross species tropism enhancements (human cells versus mouse animal model).

Figure 16:
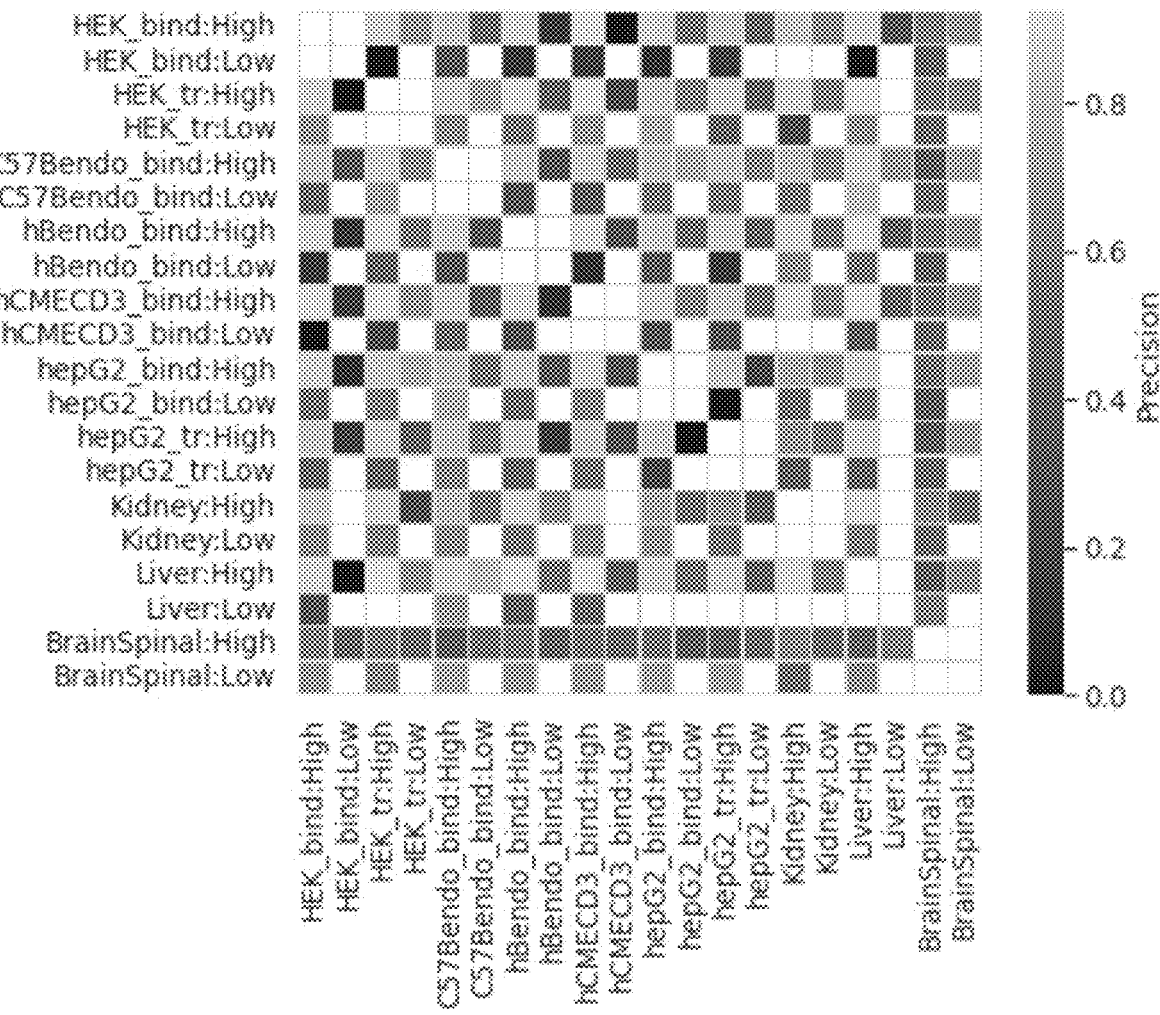
FIG. 16. provides a graph showing multifunction optimization validation.

For a systematic assessment of the MultiFxn approach, all-versus-all dual function optimizations were constructed, with the positively and negatively enrichment optimized independently (4 condition combinations X 45 pairwise function assay combinations=180 cases). The selection was performed on the 150K validation subset. Consistently, high precision was observed in most cases (FIG. 16). This further demonstrates the applicability of the MultiFxn approach.

Example 6: Materials and Methods for Examples 1-5

Training and Validation Library Design

The training and validation libraries used to learn the production fitness distribution were designed to contain a total of 150K nucleotide sequences ordered as an oligonucleotide library (Agilent). The two libraries were composed of 64.5K unique and 10K overlapping amino acid sequences generated by uniformly sampling all 20 amino acids at each position. A by-product of the uniform sampling is that the summation of the inter-variant Hamming distance is maximized (how many amino acids differ between each pair of variants at each position). Ten times the required number of variants were sampled in each library, then duplications inside and across the libraries were removed before randomly subsampling the required number for each library. The reason to generate the data with uniform sampling is to provide a non-biased scan of the sequence space so that the ML models would generalize well to the entire sequence space, in contrast to what is expected when the ML models learn on biased spaces. In addition, 1K sequences containing nonsense codons (stop codons) were included to highlight potential problems with cross packaging.

Capsid Library Synthesis

Lyophilized DNA oligonucleotide libraries (Agilent, G 7223A) were spun down at 8000 RCF for 1 min, resuspended in 10 μL μtraPure DNase/RNase-Free Distilled Water (ThermoFisher Scientific, 10977015), and incubated at 37° C. for 20 minutes. To amplify the oligonucleotide libraries and incorporate them into an AAV9 (K449R) template, 2 μL of the resuspended oligonucleotide library were used as an initial reverse primer along with 0.5 μM AAV9_K449R_Forward (Table 1) as the forward primer in a 25 μL PCR amplification reaction using Q5 Hot Start High-Fidelity 2X Master Mix (NEB, M0494S). As a PCR template, 50 ng of a plasmid containing only AAV9 VP1 amino acids 347-586 was used. The amplification conditions followed the manufacturer's protocol with an annealing temperature of 65° C. for 20 seconds and an extension time of 1.5 minutes. After 6 PCR cycles, 0.5 μM AAV9_K449R_Reverse (Table 1) was spiked into the reaction as a reverse primer to amplify only sequences containing the oligonucleotide library for an additional 25 cycles. To remove the PCR template, 1 μL of DpnI (NEB, R0176S) was added directly into the PCR reaction and incubated at 37° C. for 1 hour. Afterwards, the PCR products were cleaned up using AMPure XP beads (Beckman, A63881) following the manufacturer's protocol.

To produce NNK inserts, the AAV9_K449R_Forward and AAV9_K449R_NNK_Reverse primers were used to PCR amplify a AAV9 (K449R) template using Q5 Hot Start High-Fidelity 2X Master Mix (NEB, M0494S) following the manufacturer's protocol with an annealing temperature of 65° C. for 20 seconds and an extension time of 1.5 minutes for 30 cycles. Similar steps to the synthetic library inserts were taken to remove the PCR template and purify the PCR product.

The PCR insert was assembled into 1600 ng of a linearized mRNA selection vector (AAV9-CMV-Express) with NEBuilder HiFi DNA Assembly Master Mix (NEB, E2621L) at a 3:1 Molar ratio of insert: vector in an 80 μL reaction volume incubated at 50° C. for one hour, followed by incubation at 72° C. for 5 minutes. Afterwards, 4 μL of Quick CIP (NEB, M0508S) was spiked into the reaction and incubated at 37° C. for 30 minutes to dephosphorylate unincorporated dNTPs that may inhibit downstream processes. Finally, 4 μL of T5 Exonuclease (NEB M0663S) was added to the reaction mixture and incubated at 37° C. for 30 minutes to remove unassembled products. The final assembled products were cleaned up using AMPure XP beads (Beckman, A63881) following the manufacturer's protocol and their concentrations were quantified with a Qubit dsDNA HS Assay Kit (ThermoFisher Scientific, Q32851) and a Qubit fluorometer.

TABLE 1

| Library assembly primers | | |
|---|---|---|
| Name | Sequence | SEQ ID NO: |
| AAV9_K449R_ Forward | CGGACTCAGAC TATCAGCTCCC | 24 |
| AAV9_K449R_ Reverse | GTATTCCTTGG TTTTGAACCCA ACCG | 25 |
| AAV9_K449R_ NNK_Reverse | GTATTCCTTGGT TTTGAACCCAAC CGGTCTGCGCCT GTGCMNNMNNMN NMNNMNNMNNMN NTTGGGCACTCT GGTGG TTTGTG | 26 | mRNA Selection Vector

The mRNA selection vector (AAV9-CMV-Express) was designed to allow for selective recovery of functional AAV capsid sequences by recovering capsid mRNA from transduced cells. AAV9-CMV-Express uses a ubiquitous CMV enhancer and AAV5 p41 gene regulatory elements to drive AAV9 Cap expression. The AAV9-Express plasmid was constructed by cloning the following elements into an AAV genome plasmid in the following order: a cytomegalovirus (CMV) enhancer-promoter, a synthetic intron containing a consensus donor motif (CAGGTAAGT), consensus splice motif (TTTTTTTCTACAGGT) (SEQ ID NO: 3) and branch point sequence, downstream of the artificial intron, the AAV5 P41 promoter along with the 3' end of the AAV2 Rep gene, which includes the splice donor sequences for the capsid RNA. The capsid gene splice donor sequence in AAV2 Rep was modified from a non consensus donor sequence CAGGTACCA to a consensus donor sequence CAGGTAAGT. The wildtype adeno-associated virus serotype 9 (AAV9) capsid gene sequence was synthesized with nucleotide changes at S448 (TCA to TCT, silent mutation), K449R (AAG to AGA), and G594 (GGC to GGT, silent mutation) to introduce restriction enzyme recognition sites for oligonucleotide library fragment cloning. The AAV2 polyadenylation sequence was replaced with a simian virus (SV40) late polyadenylation signal to terminate the capsid RNA transcript.

Virus Production

Recombinant AAV libraries were generated by triple transfection of HEK293T cells using polyethylenimine (PEI) and purified by ultracentrifugation over iodixanol gradients as previously described (Deverman et al. 2016). AAV library titers were assessed with droplet digital PCR.

Titering

To determine AAV titers or assess production fitness by nuclease resistant genome recovery, 5 μL of each purified virus library were incubated with 100 μL of an endonuclease cocktail consisting of 1000 U/mL Turbonuclease (Sigma T4330-50KU) with 1X DNase I reaction buffer (NEB B0303S) in μtraPure DNase/RNase-Free distilled water at 37° C. for one hour. Next, the endonuclease solution was inactivated by adding 5 μL of 0.5M, pH8.0 EDTA (ThermoFisher Scientific, 15575020) and incubated at room temperature for 5 minutes and then at 70° C. for 10 minutes. To release encapsidated AAV genomes, 120 μL of a Proteinase K cocktail consisting of 1M NaCl, 1% N-lauroylsarcosine, 100 μg/mL Proteinase K (Qiagen, 19131) in μtraPure DNase/RNase-Free distilled water was added to the mixture and incubated at 56° C. for 2 to 16 hours. The Proteinase K treated samples were then heat inactivated at 95° C. for 10 minutes. The released AAV genomes were then serial diluted between 460-460,000× in dilution buffer consisting of 1X PCR Buffer (ThermoScientific, N8080129), 2 g/mL sheared salmon sperm DNA (ThermoScientific, AM9680), and 0.05% Pluronic F68 (ThermoScientific, 24040032) in μtraPure Water (ThermoScientific). Following sample dilution, 2 μL of the diluted samples were used as input in a ddPCR supermix for probes (Bio-Rad, 1863023) with 900 nM ITR2_Forward and ITR2_Reverse (Table 2) and 250 nM ITR2_Probe (Table 2). Droplets were generated using a QX100 Droplet Generator following the manufacturer's protocol. The droplets were then transferred to a thermocycler and cycled according to the manufacturer's protocol with an annealing/extension of 58° C. for 1 minute. Finally, droplets were read on a QX100 Droplet Digital System to determine titers.

TABLE 2

| Virus titering ddPCR primers and probe (Aurnhammeret al. 2012) | | |
|---|---|---|
| Name | Sequence | SEQ ID NO: |
| ITR2_Forward | GGAACCCCTAGTGATGGAGTT | 4 |
| ITR2_Reverse | CGGCCTCAGTGAGCGA | 5 |
| ITR2_Probe | 5'-HEX-CACTCCCTC-ZEN-TCTGCGCGCTCG-IABkFQ-3' | 6 |

Assessing Production Fitness by Nuclease Resistant Genome Recovery

To recover only encapsidated AAV genomes for downstream analysis, 1011 viral genomes were extracted using the endonuclease and Proteinase K steps outlined in the tittering section. After Proteinase K treatment, samples were column purified using a DNA Clean and Concentrator Kit (Zymo Research, D4033) and eluted in 25 μL elution buffer for NGS preparation.

NGS Sample Preparation

To prepare AAV libraries for sequencing, qPCR was performed on extracted AAV genomes or transcripts to determine the cycle thresholds for each sample type in order to prevent overamplification. Once cycle thresholds were determined, a first round PCR amplification using equal primer pairs (1-8) (Table 3) were used to attach Illumina Read 1 and Read 2 sequences using Q5 Hot Start High-Fidelity 2X Master Mix with an annealing temperature of 65° C. for 20 seconds and an extension time of 1 minute. Round 1 PCR products were purified using AMPure XP beads following the manufacturer's protocol and eluted in 25 μL μtraPure Water (ThermoScientific) and then 2 μL was used as input in a second round PCR to attach on Illumina adaptors and dual index primers (NEB, E7600S) for 5 PCR cycles using Q5 HotStart-High-Fidelity 2X Master Mix with an annealing temperature of 65° C. for 20 seconds and an extension time of 1 minute. The second round PCR products were purified using AMPure XP beads following the manufacturer's protocol and eluted in 25 μL μtraPure DNase/RNase-Free distilled water (ThermoScientific).

To quantify the amount of second round PCR product for NGS an Agilent High Sensitivity DNA Kit (Agilent, 5067-

4626) was used with an Agilent 2100 Bioanalyzer system. Second round PCR products were then pooled and diluted to 2-4 nM in 10 mM Tris-HCl, pH 8.5 and sequenced on an Illumina NextSeq 550 following the manufacturer's instructions using a NextSeq 500/550 Mid or High Output Kit (Illumina, 20024904 or 20024907). Reads were allocated as follows: I1: 8, I2:8, R1: 150, R2: 0.

TABLE 3

| | | PCR1 primers | |
|---|---|---|---|
| ame | 5' Handle | | Sequence |
| eq1_F | Read 1 | | CTTTCCCTACACGACGCTCTTC CGATCTNNNNNNNNCCAACGAA GAAGAAATTAAAACTACTAACC CG (SEQ ID NO: 7) |
| eq2_F | Read 1 | | CTTTCCCTACACGACGCTCTTC CGATCTNNNNNNNCCAACGAAG AAGAAATTAAAACTACTAACC CG (SEQ ID NO: 8) |
| eq3_F | Read 1 | | CTTTCCCTACACGACGCTCTTC CGATCTNNNNNNCCAACGAAGA AGAAATTAAAACTACTAACCC G (SEQ ID NO: 9) |
| eq4_F | Read 1 | | CTTTCCCTACACGACGCTCTTC CGATCTNNNNNCCAACGAAGAA GAAATTAAAACTACTAACCCG (SEQ ID NO: 10) |
| eq5_F | Read 1 | | CTTTCCCTACACGACGCTCTTC CGATCTNNNNCCAACGAAGAAG AAATTAAAACTACTAACCCG (SEQ ID NO: 11) |
| eq6_F | Read 1 | | CTTTCCCTACACGACGCTCTTC CGATCTNNNCCAACGAAGAAGA AATTAAAACTACTAACCCG (SEQ ID NO: 12) |
| eq7_F | Read 1 | | CTTTCCCTACACGACGCTCTTC CGATCTNNCCAACGAAGAAGAA ATTAAAACTACTAACCCG (SEQ ID NO: 13) |
| eq8_F | Read 1 | | CTTTCCCTACACGACGCTCTTC CGATCTNCCAACGAAGAAGAAA TTAAAACTACTAACCCG (SEQ ID NO: 14) |
| eq1_R | Read 2 | | GGAGTTCAGACGTGTGCTCTTC CGATCTCATCTCTGTCCTGCCA AACCATACC (SEQ ID NO: 15) |
| eq2_R | Read 2 | | GGAGTTCAGACGTGTGCTCTTC CGATCTNCATCTCTGTCCTGCC AAACCATACC (SEQ ID NO: 16) |
| eq3_R | Read 2 | | GGAGTTCAGACGTGTGCTCTTC CGATCTNNCATCTCTGTCCTGC CAAACCATACC (SEQ ID NO: 17) |
| eq4_R | Read 2 | | GGAGTTCAGACGTGTGCTCTTC CGATCTNNNCATCTCTGTCCTG CCAAACCATACC (SEQ ID NO: 18) |

TABLE 3-continued

PCR1 primers

| ame | 5' Handle | Sequence |
|---|---|---|
| eq5_R | Read 2 | GGAGTTCAGACGTGTGCTCTTC CGATCTNNNNNCATCTCTGTCCT GCCAAACCATACC (SEQ ID NO: 19) |
| eq6_R | Read 2 | GGAGTTCAGACGTGTGCTCTTC CGATCTNNNNNCATCTCTGTCC TGCCAAACCATACC (SEQ ID NO: 20) |
| eq7_R | Read 2 | GGAGTTCAGACGTGTGCTCTTC CGATCTNNNNNNCATCTCTGTC CTGCCAAACCATACC (SEQ ID NO: 21) |
| eq8_R | Read 2 | GGAGTTCAGACGTGTGCTCTTC CGATCTNNNNNNNCATCTCTGT CCTGCCAAACCATACC (SEQ ID NO: 22) |

NGS Data Processing

Sequencing data was demultiplexed with bcl2fastq (version v2.20.0.422) using the default parameters. The Read 1 sequence (excluding Illumina barcodes) was aligned to a short reference sequence of AAV9:

(SEQ ID NO: 23)
CCAACGAAGAAGAAATTAAAACTACTAACCCGGTAGCAAC

GGAGTCCTATGGACAAGTGGCCACAAACCACCAGAGTGCC

CAANNNNNNNNNNNNNNNNNNNNNNNNGCACAGGCGCAGACCG

GTTGGGTTCAAAACCAAGGAATACTTCCG

Alignment was performed with bowtie2 (version 2.4.1) (Langmead and Salzberg 2012) with the following parameters:

--end-to-end--very-sensitive--np 0--n-ceil L,21,0.5-- xeq-N 1--reorder--score-min L,-0.6,-0.6-58-3 8

Resulting SAM files from bowtie2 were sorted by read and compressed to BAM files with samtools (version 1.11-2-g26d7c73, htslib version 1.11-9-g2264113) (Danecek et al. 2021; Li et al. 2009).

Python (version 3.8.3) scripts and pysam (version 0.15.4) were used to flexibly extract the 21 nucleotide insertion from each amplicon read. Each read was assigned to one of the following bins: Failed, Invalid, or Valid. Failed reads were defined as reads that did not align to the reference sequence, or that had an in/del in the insertion region (i.e., 20 bases instead of 21 bases). Invalid reads were defined as reads whose 21 bases were successfully extracted, but matched any of the following conditions: 1) Any one base of the 21 bases had a quality score (AKA Phred score, QScore) below 20, i.e., error probability >1/100, 2) Any one base was undetermined, i.e., "N", 3) The 21 base sequence was not from the synthetic library (this case does not apply to NNK library), and 4) The 21 base sequence did not match a pattern, i.e., NNK (this case does not apply to the synthetic libraries). Valid reads were defined as reads that did not fit into either the Failed or Invalid bins. The Failed and Invalid reads were collected and analyzed for quality control purposes, and all subsequent analyses were performed on the Valid reads.

Count data for valid reads were aggregated per sequence per sample, and were stored in a pivot table format, with nucleotide sequences on the rows, and samples (Illumina barcodes) on the columns. Sequences not detected in samples were assigned a count of 0. Count data were read-per-million (RPM) normalized to the sequencing depth of each sample (Illumina barcode). As each biological sample was run in triplicate, data were aggregated for each sample by taking the mean of the RPMs. Log2 production enrichment for each variant was defined as log 2 of the ratio of its average abundance in RPM after virus production divided by RPM in the DNA library used for virus production for production fitness and for functional enrichment was defined as post-assay RPM divided by RPM in the virus library. For NNK libraries, to avoid dividing by zero when the variant is not detected, a pseudo-number equal to the RPM abundance of the least abundant variant was added, i.e., counts of 0 across all 3 replicates for the normalization sample was corrected to a count of 1 across all 3 replicates.

Data Normalization

Count data were read-per-million (RPM) normalized to the sequencing depth of each sample (Illumina barcode) with:

$$r_{i,j} = \frac{k_{i,j}}{\sum_{l=1}^{n} k_{l,j}} \times 1{,}000{,}000$$

Where "r" is the RPM-normalized count, "k" is the raw count, "i" is i=1 . . . n sequences, and "j" is j=1 . . . m samples.

As each biological sample was run in triplicate, data were aggregated for each sample by calculating the mean of the RPMs:

$$\mu_{i,s} = \frac{\sum_{l=1}^{p} r_{i,l}}{p}$$

across "p" replicates of sample "s". Normalized variance was estimated across replicates by taking the coefficient of variance (CV):

$$CV_{i,s} = \frac{\mu_{i,s}}{\sigma_{i,s}}$$

where "$\sigma_{i,s}$" is the standard deviation for variant "i" in sample "s" over "p" replicates.

Log2 enrichment for each sequence was defined as:

$$e_{i,s} = \log_2\left(\frac{\mu_{i,s}}{\mu_{corrected,i,t}}\right)$$

Where "e" is the log 2 enrichment, "u" is the mean of the replicate RPMs, and "t" is the normalization sample. For production fitness, the sample "s" is the variant abundance after virus production, and the normalization sample "t" is the variant abundance in the plasmid pool. For functional screens, the sample "s" is the variant abundance of the screen, and the normalization factor "t" is the variant abundance after virus production. To avoid dividing by 0 in "e", "$\mu_{corrected,i,t}$" is defined as:

$$\mu_{corrected,i,t} = \begin{cases} \mu_{i,t}, & \text{for } \mu_{i,t} > 0 \\ 1/\sum_{l=1}^{n} k_{l,t}, & \text{for } \mu_{i,t} = 0 \end{cases}$$

that is, counts of 0 across all 3 replicates for the normalization sample were corrected to a count of 1 across all 3 replicates.

Production Fitness Training and Validation

A robust ML framework was designed and used for the production fitness and Fit4Fxn functional predictions. The framework was composed of the ML model structure and applied techniques to control the training process to avoid overfitting of the models to training data so that they would generalize well to independent data. An LSTM regression model with two hidden layers (140 nodes then 20 nodes) was implemented in Keras. The input layer was 7-mer amino acid sequences hot encoded into a 20×7 matrix. Loss was optimized by mean-squared-error with the Adam optimizer. The batch size was set to 500 observations. Model training was controlled by a custom early stopping procedure where the training process was terminated if the ratio between training error and validation error exceeded 0.85.

For production fitness learning, the training size was optimized by training the framework on increments of 1K variants. Variants that were not detected (N=5,380) after virus production were filtered out from training. Model validation performance was reported at each training size, and a size of 24K variants was determined to be the optimal training size. The training library core variants (N=60K after removing the non-detected) were then randomly divided into training (24K), validation (12K) and testing subsets (25.6K). The model was trained on the training set, validated during the training process on the validation set, and tested on the held-out testing set. The model was further tested on the 10K shared variants from the validation library (FIG. 6A) to assess its generalization.

Sampling and Pre-Synthesis Validation of Fit4Fxn Library Sampling

The Fit4Fxn libraries were intended to be sampled from the high-production fitness space of the entire sequence space. For the Hammerhead library, 7-mer amino acid sequences were uniformly sampled 100 times the required library size (240K Hammerhead variants*100=24M variants), by uniformly sampling each amino acid at each of the 7 positions. Duplicates were removed, and remaining sequences were scored using the production fitness predictor. Then, the 240K Hammerhead library variants were probabilistically sampled from the parametrized high-fit distribution (FIG. 8B).

A simulation was devised to evaluate this Fit4Fxn sampling approach on measured data before synthesizing the library. The sequence of the 64.5K variants of the validation library were scored using the production fitness predictor, and these scores were projected into the fitness landscape of the training library. Then, N=10K variants were sampled from the high-fit distribution (FIG. 8B) to constitute the simulated Fit4Fxn library. Predicted versus measured production fitness was assessed using correlation, and agreement between the high-fit distributions of the training and simulated sets was assessed using Kullback-Liebler (KL) divergence. For the Hammerhead library, in addition to the 240K high-fit variants, 1K stop-codon containing variants were added, and 3K variants from the 10K shared variants between the training and validation libraries were added as a control set.

Validating Hammerhead

The purpose of the 3K variants in the control set of the Fit4Fxn libraries was to calibrate its production fitness scores to those in the training libraries. To calibrate the Hammerhead library production fitness, the control set was used to fit an ordinary linear regression model of the measured production fitness scores, between the Hammerhead library and the training library. These regression parameters were applied to the Hammerhead library's production fitness scores to obtain calibrated production fitness scores. After synthesizing the Hammerhead, the fitness scores predicted for its variants before synthesis were compared to their measured fitness by assessing their correlation.

AAV Functional Assays

Purified virus libraries were injected at a dose of 1012 to 7-8 week old C57BL/6J (Jax, 000664) mice. Two hours post injection serum was collected and animal organs were harvested using disposable 3 mm biopsy punches (Integra, 33-32-P/25) with a new biopsy punch used per organ per replicate. Harvested tissues were immediately frozen in dry ice. AAV genomes were recovered using a DNeasy kit (Qiagen, 69504) following the manufacturer's protocol and samples were eluted in 200 μL elution buffer for NGS preparation.

In Vitro Binding and Transduction Assays

HEK293T/17 (ATCC® CRL-11268™), HepG2 (ATCC® HB-8065™), hCMEC/D3 (Millipore, SCC066), and human and mouse BMVECs (Cell Biologics, H-6023 and C57-H6023) were grown in 100 mm dishes and exposed to the Fit4Fxn or (NNK) 7-mer library (MOI 1E4 for HEK293T/17, MOI3E4 for hCMEC/D3, MOI 6E4 for primary human and mouse BMVECs and MOI5E3 for HepG2) diluted in 10 mL of growth media at 4° C. with gentle rocking for 2 hours. After that, cells were washed 3 times with DPBS, and total DNA was extracted with DNeasy kit (Qiagen) according to the manufacturer instructions. Half of the recovered DNA was used in PCR amplification for viral genome sequences recovery.

Transduction assays were performed as described above with the following exceptions. The cells were cultured in growth media containing virus for 60 hours and then total RNA was extracted with the Rneasy kit (Qiagen). 5 μg of RNA was converted to cDNA using Maxima H Minus Reverse Transcriptase according to manufacturer instructions.

Functional Assay Screening with Hammerhead

Functional scores were quantified as the log 2 of the fold-change enrichment of the variant reads-per-million (RPM) after the screen relative to its RPM in the virus library, i.e. log 2 (Assay RPM/Virus RPM). Fit4Fxn models utilized the same two-layer LSTM design as the production fitness predictor and used the same early stopping methodology in that ML framework. Out of the 240K variants in the Hammerhead library, 90K were allocated for training and testing Fit4Fxn models and 150K variants were held-out for validating the MultiFxn approach. Out of the 90K variants used for Fit4Fxn training, 5K were set aside for model validation during training, and the rest used for model training and testing. The training size for each Fit4Fxn model was optimized independently. As with the production fitness model, the function models were assessed by correlation between the predicted and measured functional scores.

MultiFxn Library Designs

Two-function optimizations were constructed as a group of four combinations: high-high, high-low, low-high, low-low. These two-function optimizations were performed over 45 pairs of functions (10 functions) for a total of 190 conditions (FIG. 16). As a proof of concept, the high and low functions were defined arbitrarily as above the 67th percentile and below the 33rd percentile measured from the model construction subset (90K), respectively. To reduce the false positive rate, the high function thresholds were shifted by 5% of the range (max-min) of functional scores. The selection pool of 150K variants for the dual function optimizations had production fitness optimized high by default.

The Hammerhead library was split into two subsets: 90K variants for constructing the function learning ML models (training and validating), and 150K variants for validating the MultiFxn approach. For each variant in the 150K validation pool, function scores were predicted for all 10 functions. Then, for each of the 190 two-function optimization cases, two sets were built: 1) predicted positive, i.e., variants whose predicted scores satisfied the two-function optimization, and 2) true positive, i.e., variants whose measured scores satisfied the two-function optimization. The quality of identification of the intersections is assessed in terms of precision (intersection of true and predicted positives/predicted positives).

The cross-species validation was performed in a similar manner but four functions were optimized simultaneously: binding and transduction of the HepG2 cells and liver directed biodistribution in mice. The thresholds were selected in the same manner as in the two-selection validation (above the 67th percentile). Production fitness was optimized at above the 67th percentile of the high production fitness space as measured in the 90K model building set.

REFERENCES

1. Albright, B., Storey, C., Murlidharan, G., Rivera, R. C., and Asokan, A. (2017). Discovery of a Neurotropic Footprint That Enables AAV Transport Across the Blood-Brain Barrier. In MOLECULAR THERAPY, (CELL PRESS 50 HAMPSHIRE ST, FLOOR 5, CAMBRIDGE, MA 02139 USA), pp. 230-231.
2. Aurnhammer, C., Haase, M., Muether, N., Hausl, M., Rauschhuber, C., Huber, I., Nitschko, H., Busch, U., Sing, A., Ehrhardt, A., et al. (2012). Universal real-time PCR for the detection and quantification of adeno-associated virus serotype 2-derived inverted terminal repeat sequences. Hum. Gene Ther. Methods 23, 18-28.
3. Bedbrook, C. N., Yang, K. K., Robinson, J. E., Mackey, E. D., Gradinaru, V., and Arnold, F. H. (2019). Machine learning-guided channelrhodopsin engineering enables minimally invasive optogenetics. Nat. Methods 16, 1176-1184.
4. Bogan, A. A., and Thorn, K. S. (1998). Anatomy of hot spots in protein interfaces. J. Mol. Biol. 280, 1-9.
5. Bryant, D. H., Bashir, A., Sinai, S., Jain, N. K., Ogden, P. J., Riley, P. F., Church, G. M., Colwell, L. J., and Kelsic, E. D. (2021). Deep diversification of an AAV capsid protein by machine learning. Nat. Biotechnol.
6. Chan, K. Y., Jang, M. J., Yoo, B. B., Greenbaum, A., Ravi, N., Wu, W.-L., Sánchez-Guardado, L., Lois, C., Mazmanian, S. K., Deverman, B. E., et al. (2017). Engineered AAVs for efficient noninvasive gene delivery to the central and peripheral nervous systems. Nat. Neurosci. 20, 1172-1179.
7. Chao, G., Lau, W. L., Hackel, B. J., Sazinsky, S. L., Lippow, S. M., and Wittrup, K. D. (2006). Isolating and engineering human antibodies using yeast surface display. Nat. Protoc. 1, 755-768.
8. Dalkara, D., Byrne, L. C., Klimczak, R. R., Visel, M., Yin, L., Merigan, W. H., Flannery, J. G., and Schaffer, D. V. (2013). In vivo-directed evolution of a new adeno-associated virus for therapeutic outer retinal gene delivery from the vitreous. Sci. Transl. Med. 5, 189ra76.
9. Danecek, P., Bonfield, J. K., Liddle, J., Marshall, J., Ohan, V., Pollard, M. O., Whitwham, A., Keane, T., McCarthy, S. A., Davies, R. M., et al. (2021). Twelve years of SAMtools and BCFtools. Gigascience 10.
10. Deverman, B. E., Pravdo, P. L., Simpson, B. P., Kumar, S. R., Chan, K. Y., Banerjee, A., Wu, W.-L., Yang, B., Huber, N., Pasca, S. P., et al. (2016). Cre-dependent selection yields AAV variants for widespread gene transfer to the adult brain. Nat. Biotechnol. 34, 204-209.
11. Flytzanis, N.C., Goeden, N., Goertsen, D., Cummins, A., Pickel, J., and Gradinaru, V. (2020). Broad gene expression throughout the mouse and marmoset brain after intravenous delivery of engineered AAV capsids.
12. Hanlon, K. S., Meltzer, J. C., Buzhdygan, T., Cheng, M. J., Sena-Esteves, M., Bennett, R. E., Sullivan, T. P., Razmpour, R., Gong, Y., Ng, C., et al. (2019). Selection of an Efficient AAV Vector for Robust CNS Transgene Expression. Molecular Therapy-Methods & Clinical Development 15, 320-332.
13. Hochreiter, S., and Schmidhuber, J. (1997). Long short-term memory. Neural Comput. 9, 1735-1780.
14. Huang, Q., Chan, K. Y., Tobey, I. G., Chan, Y. A., Poterba, T., Boutros, C. L., Balazs, A. B., Daneman, R., Bloom, J. M., Seed, C., et al. (2019). Delivering genes across the blood-brain barrier: LY6A, a novel cellular receptor for AAV-PHP.B capsids. PLOS One 14, e0225206.
15. Kariolis, M. S., Wells, R. C., Getz, J. A., Kwan, W., Mahon, C. S., Tong, R., Kim, D. J., Srivastava, A., Bedard, C., Henne, K. R., et al. (2020). Brain delivery of therapeutic proteins using an Fc fragment blood-brain barrier transport vehicle in mice and monkeys. Sci. Transl. Med. 12.
16. Körbelin, J., Dogbevia, G., Michelfelder, S., Ridder, D. A., Hunger, A., Wenzel, J., Seismann, H., Lampe, M., Bannach, J., Pasparakis, M., et al. (2016). A brain microvasculature endothelial cell-specific viral vector with the potential to treat neurovascular and neurological diseases. EMBO Mol. Med. 8, 609-625.
17. Kumar, S. R., Miles, T. F., Chen, X., Brown, D., Dobreva, T., Huang, Q., Ding, X., Luo, Y., Einarsson, P. H., Greenbaum, A., et al. (2020). Multiplexed Cre-dependent selection yields systemic AAVs for targeting distinct brain cell types. Nat. Methods 17, 541-550.
18. Langmead, B., and Salzberg, S. L. (2012). Fast gapped-read alignment with Bowtie 2. Nat. Methods 9, 357-359.
19. Li, H., Handsaker, B., Wysoker, A., Fennell, T., Ruan, J., Homer, N., Marth, G., Abecasis, G., Durbin, R., and 1000 Genome Project Data Processing Subgroup (2009). The Sequence Alignment/Map format and SAMtools. Bioinformatics 25, 2078-2079.
20. Lisowski, L., Dane, A. P., Chu, K., Zhang, Y., Cunningham, S. C., Wilson, E. M., Nygaard, S., Grompe, M., Alexander, I. E., and Kay, M. A. (2014). Selection and evaluation of clinically relevant AAV variants in a xenograft liver model. Nature 506, 382-386.
21. Marques, A. D., Kummer, M., Kondratov, O., Banerjee, A., Moskalenko, O., and Zolotukhin, S. (2021). Applying machine learning to predict viral assembly for adeno-associated virus capsid libraries. Mol Ther Methods Clin Dev 20, 276-286.

22. Mason, D. M., Friedensohn, S., Weber, C. R., Jordi, C., Wagner, B., Meng, S., Gainza, P., Correia, B. E., and Reddy, S. T. (2019). Deep learning enables therapeutic antibody optimization in mammalian cells by deciphering high-dimensional protein sequence space.

23. Matochko, W. L., Chu, K., Jin, B., Lee, S. W., Whitesides, G. M., and Derda, R. (2012). Deep sequencing analysis of phage libraries using Illumina platform. Methods 58, 47-55.

24. Mattheakis, L. C., Bhatt, R. R., and Dower, W. J. (1994). An in vitro polysome display system for identifying ligands from very large peptide libraries. Proc. Natl. Acad. Sci. U.S.A 91, 9022-9026.

25. McCafferty, J., Griffiths, A. D., Winter, G., and Chiswell, D. J. (1990). Phage antibodies: filamentous phage displaying antibody variable domains. Nature 348, 552-554.

26. Müller, O. J., Kaul, F., Weitzman, M. D., Pasqualini, R., Arap, W., Kleinschmidt, J. A., and Trepel, M. (2003). Random peptide libraries displayed on adeno-associated virus to select for targeted gene therapy vectors. Nat. Biotechnol. 21, 1040-1046.

27. Nonnenmacher, M., Wang, W., Child, M. A., Ren, X.-Q., Huang, C., Ren, A. Z., Tocci, J., Chen, Q., Bittner, K., Tyson, K., et al. (2021). Rapid evolution of blood-brain-barrier-penetrating AAV capsids by RNA-driven biopanning. Mol Ther Methods Clin Dev 20, 366-378.

28. Paulk, N. K., Pekrun, K., Charville, G. W., Maguire-Nguyen, K., Wosczyna, M. N., Xu, J., Zhang, Y., Lisowski, L., Yoo, B., Vilches-Moure, J. G., et al. (2018). Bioengineered Viral Platform for Intramuscular Passive Vaccine Delivery to Human Skeletal Muscle. Mol Ther Methods Clin Dev 10, 144-155.

29. Pulicherla, N., Shen, S., Yadav, S., Debbink, K., Govindasamy, L., Agbandje-McKenna, M., and Asokan, A. (2011). Engineering liver-detargeted AAV9 vectors for cardiac and musculoskeletal gene transfer. Mol. Ther. 19, 1070-1078.

30. Qian, R., Xiao, B., Li, J., and Xiao, X. (2021). Directed Evolution of AAV Serotype 5 for Increased Hepatocyte Transduction and Retained Low Humoral Seroreactivity. Mol Ther Methods Clin Dev 20, 122-132.

31. Ravindra Kumar, S., Miles, T. F., Chen, X., Brown, D., Dobreva, T., Huang, Q., Ding, X., Luo, Y., Einarsson, P. H., Greenbaum, A., et al. (2020). Multiplexed Cre-dependent selection yields systemic AAVs for targeting distinct brain cell types. Nat. Methods 17, 541-550.

32. Ravn, U., Gueneau, F., Baerlocher, L., Osteras, M., Desmurs, M., Malinge, P., Magistrelli, G., Farinelli, L., Kosco-Vilbois, M. H., and Fischer, N. (2010). By-passing in vitro screening-next generation sequencing technologies applied to antibody display and in silico candidate selection. Nucleic Acids Res. 38, e193-e193.

33. Riesselman, A., Shin, J.-E., Kollasch, A., McMahon, C., Simon, E., Sander, C., Manglik, A., Kruse, A., and Marks, D. (2019). Accelerating Protein Design Using Autoregressive Generative Models.

34. Rolnick, D., Veit, A., Belongie, S., and Shavit, N. (2017). Deep Learning is Robust to Massive Label Noise.

35. Smith, G. P. (1985). Filamentous fusion phage: novel expression vectors that display cloned antigens on the virion surface. Science 228, 1315-1317.

36. Traxlmayr, M. W., Kiefer, J. D., Srinivas, R. R., Lobner, E., Tisdale, A. W., Mehta, N. K., Yang, N.J., Tidor, B., and Wittrup, K. D. (2016). Strong Enrichment of Aromatic Residues in Binding Sites from a Charge-neutralized Hyperthermostable Sso7d Scaffold Library. J. Biol. Chem. 291, 22496-22508.

37. Tse, L. V., Klinc, K. A., Madigan, V. J., Castellanos Rivera, R. M., Wells, L. F., Havlik, L. P., Smith, J. K., Agbandje-McKenna, M., and Asokan, A. (2017). Structure-guided evolution of antigenically distinct adeno-associated virus variants for immune evasion. Proc. Natl. Acad. Sci. U.S. A. 114, E4812-E4821.

38. Weinmann, J., Weis, S., Sippel, J., Tulalamba, W., Remes, A., El Andari, J., Herrmann, A.-K., Pham, Q. H., Borowski, C., Hille, S., et al. (2020). Identification of a myotropic AAV by massively parallel in vivo evaluation of barcoded capsid variants. Nat. Commun. 11, 1-12.

39. Whitehead, T. A., Chevalier, A., Song, Y., Dreyfus, C., Fleishman, S. J., De Mattos, C., Myers, C. A., Kamisetty, H., Blair, P., Wilson, I. A., et al. (2012). Optimization of affinity, specificity and function of designed influenza inhibitors using deep sequencing. Nat. Biotechnol. 30, 543-548.

Figure 17:
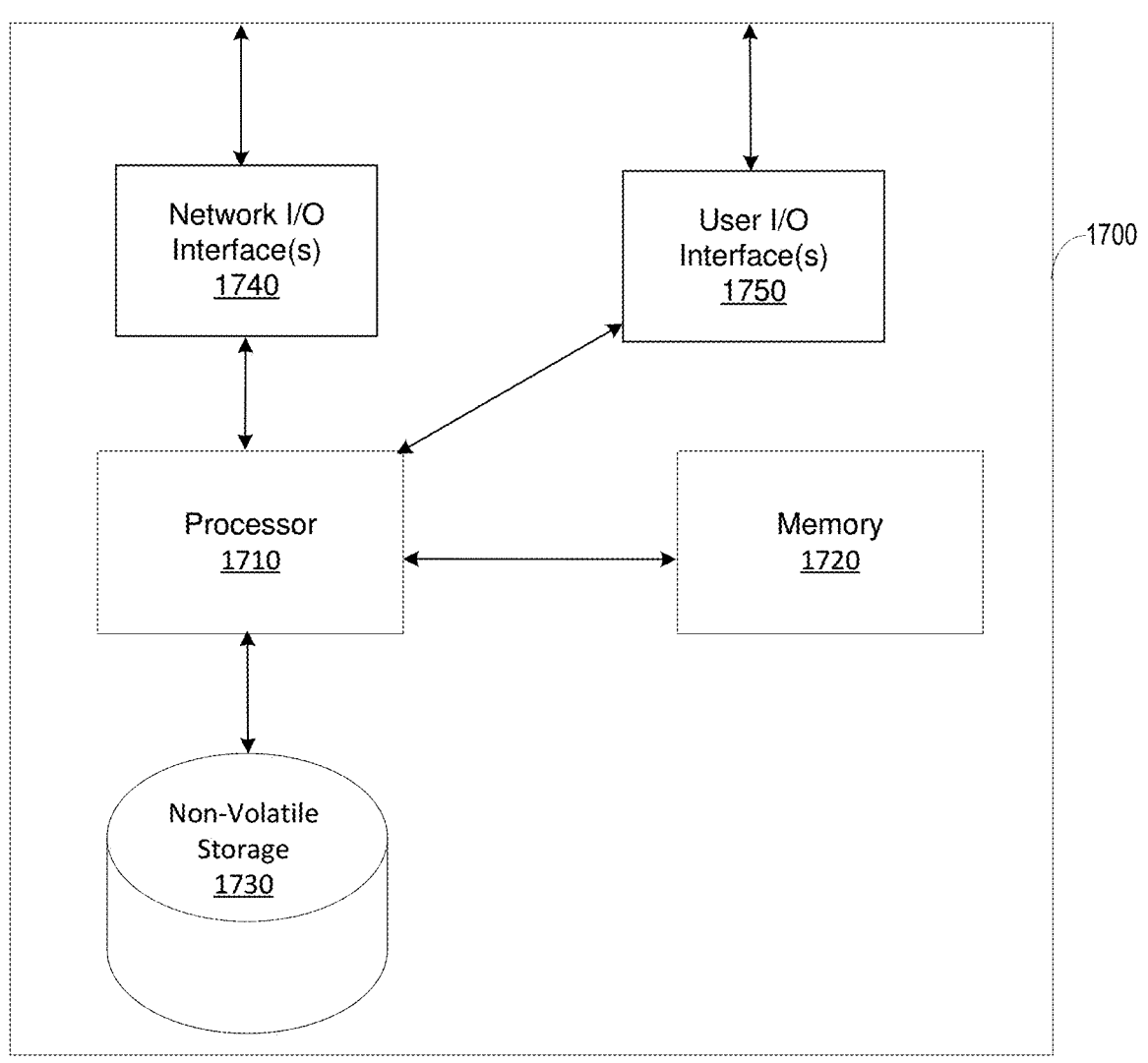
FIG. 17 is a block diagram of an illustrative computer system that may be used in implementing some of the technology described herein.

An illustrative implementation of a computer system 1700 that may be used in connection with any of the embodiments of the technology described herein is shown in FIG. 17. The computer system 1700 includes one or more processors 1710 and one or more articles of manufacture that comprise non-transitory computer-readable storage media (e.g., memory 1720 and one or more non-volatile storage media 1730). The processor 1710 may control writing data to and reading data from the memory 1720 and the non-volatile storage device 1730 in any suitable manner, as the aspects of the technology described herein are not limited in this respect. To perform any of the functionality described herein, the processor 1710 may execute one or more processor-executable instructions stored in one or more non-transitory computer-readable storage media (e.g., the memory 1720), which may serve as non-transitory computer-readable storage media storing processor-executable instructions for execution by the processor 1710.

Computing device 1700 may also include a network input/output (I/O) interface 1740 via which the computing device may communicate with other computing devices (e.g., over a network), and may also include one or more user I/O interfaces 1750, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

EQUIVALENTS

Those skilled in the art will recognize or be able to ascertain using no more than routine experimentation, many equivalents to the specific embodiments of the invention described here. Such equivalents are intended to be encompassed by the following claims.

All references, including patent documents, are incorporated by reference in their entirety.

What is claimed is:

1. A method comprising:

synthesizing a library of uniformly distributed amino acid sequences;

screening the library of uniformly distributed amino acid sequences for production fitness and assigning to each amino acid sequence of the library of uniformly distributed amino acid sequences production fitness information;

training a first statistical model, using the library of uniformly distributed amino acid sequences and the production fitness information, to predict a production-fit amino acid sequence;

producing, using the first statistical model and the production fitness information, an amino acid sequence library having amino acid sequences with predicted production fitness in accordance with the production fitness information;

accessing a second statistical model relating at least one amino acid sequence of the library having amino acid sequences with predicted production fitness to at least one protein characteristic other than production fitness;

determining, using the library having amino acid sequences with predicted production fitness and the second statistical model, production-fit amino acid sequences having the at least one protein characteristic;

synthesizing a peptide having an amino acid sequence selected from among the production-fit amino acid sequences having the at least one protein characteristic; and inserting the synthesized peptide into an adeno-associated virus (AAV) capsid.

2. The method of claim 1, wherein the production fitness information corresponds to a mode of a distribution of production fitness data used to train the first statistical model.

3. The method of claim 1, wherein the first statistical model is trained using measured production fitness values having a multimodal distribution with modes, and the production fitness information corresponds to a mode of the multimodal distribution with highest value.

4. The method of claim 1, wherein the first and/or second statistical model comprises at least one neural network.

5. The method of claim 1, wherein each of the amino acid sequences of the library having amino acid sequences with predicted production fitness comprises between 4-20 amino acids.

6. The method of claim 1, wherein each of the amino acid sequences of the library having amino acid sequences with predicted production fitness comprises a number of amino acids and at least 60% of the amino acid sequences of the amino acid sequence library have a Hamming distance equal to the number of amino acids.

7. The method of claim 1, wherein the amino acid sequences of the library having amino acid sequences with predicted production fitness are targeting peptides that are inserted into the AAV capsid.

8. The method of claim 1, wherein the at least one protein characteristic includes at least one selected from the group consisting of: binding affinity to a target cell type, binding specificity to a target cell type, cell-type specific repulsion, biodistribution to one or more organs or tissues, and transduction of a target cell type.

* * * * *